(12) United States Patent
Green et al.

(10) Patent No.: US 9,029,367 B2
(45) Date of Patent: May 12, 2015

(54) BACE INHIBITORS

(71) Applicant: Eli Lilly and Company, Indianapolis, IN (US)

(72) Inventors: Steven James Green, Indianapolis, IN (US); Erik James Hembre, Indianapolis, IN (US); Dustin James Mergott, Zionsville, IN (US); Yuan Shi, Carmel, IN (US); Brian Morgan Watson, Carmel, IN (US); Leonard Larry Winneroski, Jr., Greenwood, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/301,358

(22) Filed: Jun. 11, 2014

(65) Prior Publication Data

US 2014/0371212 A1 Dec. 18, 2014

Related U.S. Application Data

(60) Provisional application No. 61/877,373, filed on Sep. 13, 2013, provisional application No. 61/836,175, filed on Jun. 18, 2013.

(51) Int. Cl.
*C07D 513/04* (2006.01)
*C07D 498/04* (2006.01)
*A61K 31/5365* (2006.01)
*A61K 31/5415* (2006.01)

(52) U.S. Cl.
CPC ............ *C07D 513/04* (2013.01); *C07D 498/04* (2013.01); *A61K 31/5365* (2013.01); *A61K 31/5415* (2013.01)

(58) Field of Classification Search
USPC .......................................... 544/91; 514/230.5
See application file for complete search history.

(56) References Cited

U.S. PATENT DOCUMENTS

| | | | |
|---|---|---|---|
| 7,868,000 B2 | 1/2011 | Zhu et al. |
| 8,158,620 B2 | 4/2012 | Suzuki et al. |
| 8,168,630 B2 | 5/2012 | Tamura et al. |
| 8,173,642 B2 | 5/2012 | Kobayashi et al. |
| 8,198,269 B2 | 6/2012 | Motoki et al. |
| 8,278,441 B2 | 10/2012 | Mergott et al. |
| 8,338,407 B2 | 12/2012 | Hall et al. |
| 8,389,513 B2 | 3/2013 | Banner et al. |
| 8,598,161 B2 | 12/2013 | Wu |
| 8,637,504 B2 | 1/2014 | Hori et al. |
| 8,653,067 B2 | 2/2014 | Kobayashi et al. |
| 2009/0209755 A1 | 8/2009 | Suzuki et al. |
| 2012/0190848 A1 | 7/2012 | Mitasev et al. |
| 2012/0202804 A1 | 8/2012 | Ellard et al. |
| 2012/0245154 A1 | 9/2012 | Anan et al. |

(Continued)

FOREIGN PATENT DOCUMENTS

| WO | 2011009898 A1 | 1/2011 |
|---|---|---|
| WO | 2012093148 A1 | 7/2012 |

(Continued)

OTHER PUBLICATIONS

International Search Report, PCT/US2014/041825, Jul. 30, 2014.
Purser, Sophie et al., "Fluorine in medicinal chemistry", Chemical Society Reviews, 2008, 37, 320-330.

(Continued)

*Primary Examiner* — Kahsay Habte
(74) *Attorney, Agent, or Firm* — Nelsen L. Lentz

(57) ABSTRACT

The present invention provides a compound of Formula III:

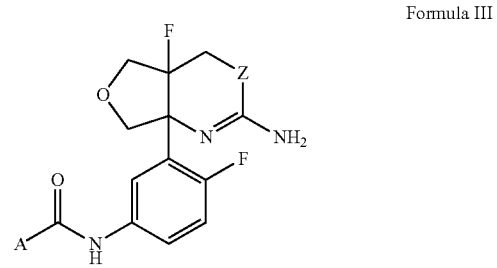

Formula III
wherein A is:

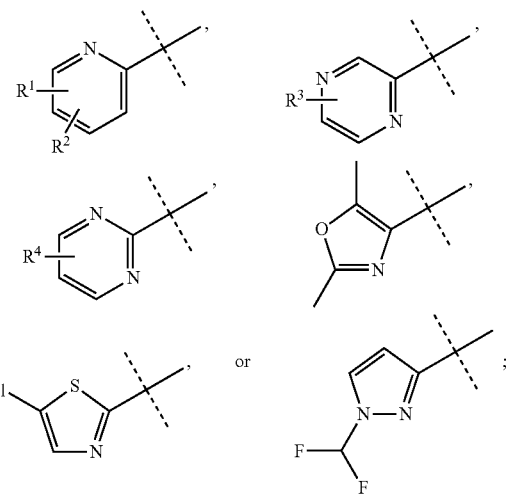

and Z, $R^1$, $R^2$, $R^3$, and $R^4$ are as defined herein, or a pharmaceutically acceptable salt thereof, which is useful for treating Alzheimer's disease.

15 Claims, No Drawings

(56) References Cited

U.S. PATENT DOCUMENTS

| | | |
|---|---|---|
| 2012/0245155 A1 | 9/2012 | Yoshida et al. |
| 2012/0245157 A1 | 9/2012 | Masui et al. |
| 2012/0258962 A1 | 10/2012 | Hilpert et al. |
| 2012/0295900 A1 | 11/2012 | Hilpert et al. |
| 2013/0053373 A1 | 2/2013 | Brodney et al. |
| 2013/0172331 A1 | 7/2013 | Lueoend et al. |
| 2013/0296308 A1 | 11/2013 | Brodney et al. |
| 2014/0023667 A1 | 1/2014 | Stamford et al. |

FOREIGN PATENT DOCUMENTS

| | | |
|---|---|---|
| WO | 2012098461 A1 | 7/2012 |
| WO | 2012168175 A1 | 12/2012 |
| WO | 2013162065 A1 | 10/2013 |
| WO | 2014/015125 A1 | 1/2014 |
| WO | 2014013076 A1 | 1/2014 |

OTHER PUBLICATIONS

Patrick C. May. et al., Robust Central Reduction of Amyloid-beta Humans with an Orally Available, Non-Peptidic Beta-Secretase Inhibitor, J. of Neuroscience, Nov. 16, 2011, 31(46), pp. 16507-16516.

Hans Hilpert et al., Beta-Secretase (BACE1) Inhibitors with High in Vivo Efficacy Suitable for Clinical Evaluation in Alzheimer's Disease, J Med. Chem., 2013, 56, pp. 3980-3995.

Written Opinion of the International Searching Authority, PCT/US2014/041825, Aug. 7, 2014.

BACE INHIBITORS

The present invention relates to novel BACE inhibitors, to pharmaceutical compositions comprising the compounds, to methods of using the compounds to treat physiological disorders, and to intermediates and processes useful in the synthesis of the compounds.

The present invention is in the field of treatment of Alzheimer's disease and other diseases and disorders involving amyloid β (Abeta) peptide, a neurotoxic and highly aggregatory peptide segment of the amyloid precursor protein (APP). Alzheimer's disease is a devastating neurodegenerative disorder that affects millions of patients worldwide. In view of the currently approved agents on the market which afford only transient, symptomatic benefits to the patient, there is a significant unmet need in the treatment of Alzheimer's disease.

Alzheimer's disease is characterized by the generation, aggregation, and deposition of Abeta in the brain. Complete or partial inhibition of β-secretase (β-site amyloid precursor protein-cleaving enzyme; BACE) has been shown to have a significant effect on plaque-related and plaque-dependent pathologies in mouse models suggesting that even small reductions in Abeta peptide levels might result in a long-term significant reduction in plaque burden and synaptic deficits, thus providing significant therapeutic benefits, particularly in the treatment of Alzheimer's disease.

US 2012/0202804 discloses fused aminodihydro-oxazine derivatives which possess BACE inhibitory activity and are further disclosed as useful therapeutic agents for a neurodegenerative disease caused by Abeta peptide, such as Alzheimer's type dementia. U.S. Pat. No. 8,158,620 discloses fused aminodihydrothiazine derivatives which possess BACE inhibitory activity and are further disclosed as useful therapeutic agents for a neurodegenerative disease caused by Abeta peptide, such as Alzheimer's type dementia. US 2012/0245155 discloses fused heterocyclic compounds which also possess BACE inhibitory activity and are further disclosed as being useful for treating Alzheimer's disease.

BACE inhibitors with central nervous system (CNS) penetration are desired to provide treatments for Abeta peptide-mediated disorders, such as Alzheimer's disease. The present invention provides certain novel compounds that are inhibitors of BACE. In addition, the present invention provides certain novel compounds which penetrate the CNS. The present invention also provides certain novel compounds which have the potential for an improved side-effect profile.

Accordingly, the present invention provides a compound of Formula I:

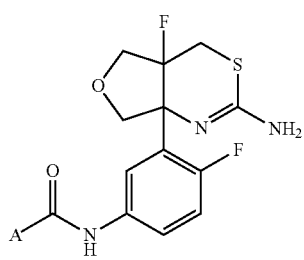

Formula I

Formula I wherein A is:

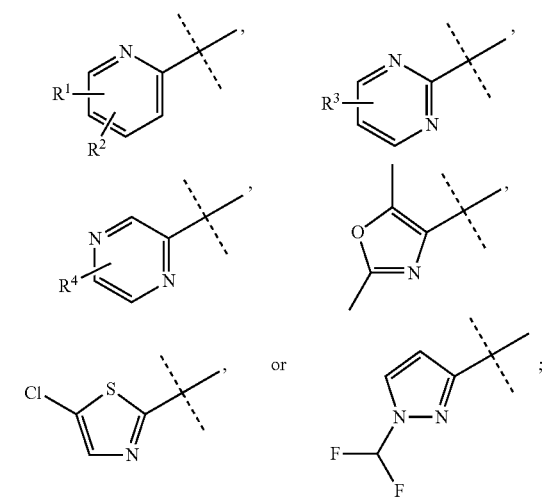

$R^1$ is H, F, Cl, CN, $OCH_2CF_3$, or $OCH_2CF_2CHF_2$;
$R^2$ is H, $CH_3$, F, or Cl;
$R^3$ is H, F, or Cl; and
$R^4$ is H, F, Cl, $CH_3$, $OCH_3$, $CF_3$, $OCH_2CF_3$,

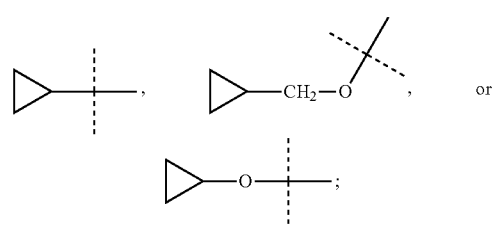

or a pharmaceutically acceptable salt thereof.

The present invention further provides a compound of Formula II:

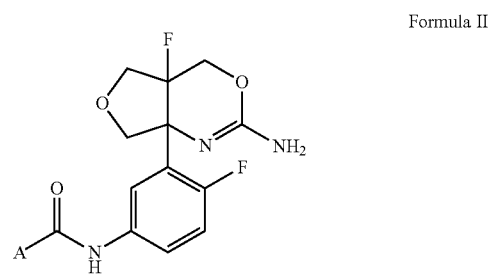

Formula II

Formula II wherein A is:

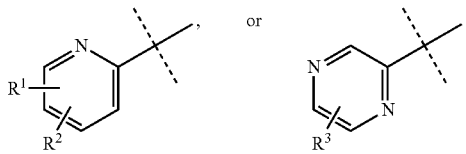

$R^1$ is H, F, Cl, CN, or $OCH_2CF_3$;
$R^2$ is H, F, Cl, or $CH_3$; and
$R^3$ is H, $OCH_3$, or $OCH_2CF_3$;
or a pharmaceutically acceptable salt thereof.

The present invention further provides a compound of Formula III:

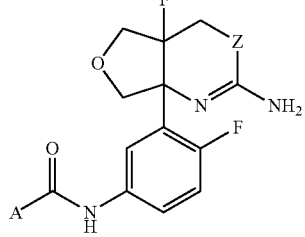

Formula III

Formula III
wherein A is:

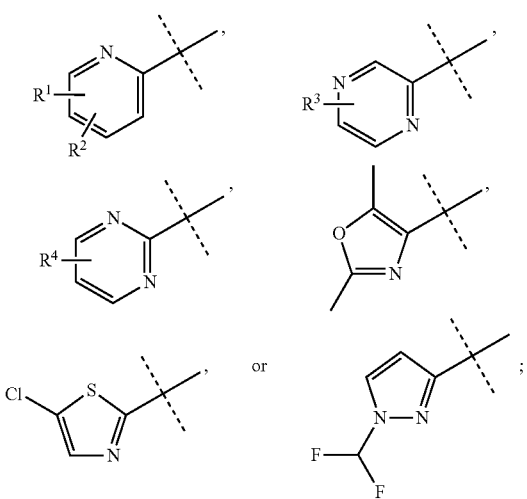

Z is O or S;
$R^1$ is H, F, Cl, CN, $OCH_3$, $OCH_2CH_2OCH_3$,

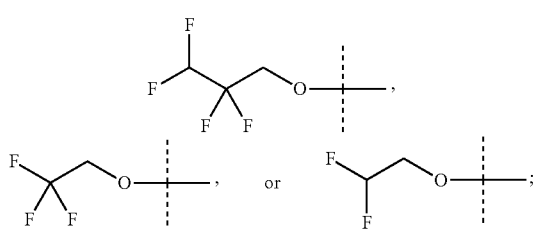

$R^2$ is H, F, Cl, or $CH_3$;
$R^3$ is H, F, Cl, $CH_3$, $CF_3$, C1-C3 alkoxy, $OCH_2CH_2OCH_3$,

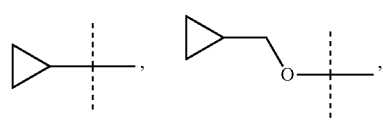

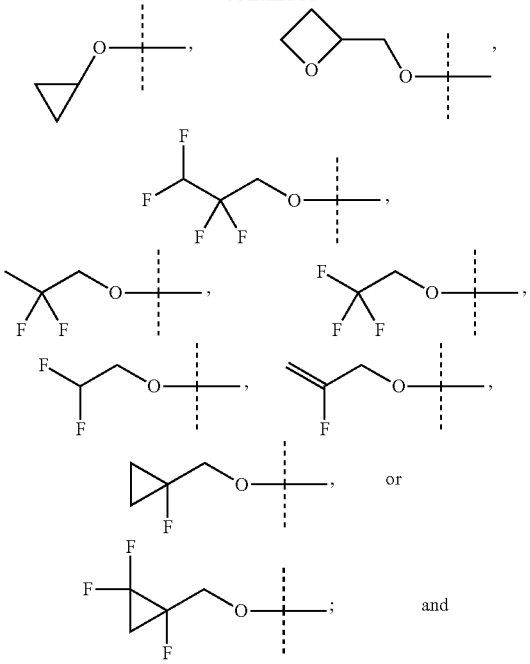

$R^4$ is H, F, Cl, or $OCH_3$;
or a pharmaceutically acceptable salt thereof.

The present invention also provides a method of treating Alzheimer's disease in a patient, comprising administering to a patient in need of such treatment an effective amount of a compound of Formulas I, II, or III, or a pharmaceutically acceptable salt thereof.

The present invention further provides a method of preventing the progression of mild cognitive impairment to Alzheimer's disease in a patient, comprising administering to a patient in need of such treatment an effective amount of a compound of Formulas I, II, or III, or a pharmaceutically acceptable salt thereof. The present invention also provides a method of inhibiting BACE in a patient, comprising administering to a patient in need of such treatment an effective amount of a compound of Formulas I, II, or III, or a pharmaceutically acceptable salt thereof. The present invention also provides a method for inhibiting BACE-mediated cleavage of amyloid precursor protein, comprising administering to a patient in need of such treatment an effective amount of a compound of Formulas I, II, or III, or a pharmaceutically acceptable salt thereof. The invention further provides a method for the inhibition of production of Abeta peptide, comprising administering to a patient in need of such treatment an effective amount of a compound of Formulas I, II, or III, or a pharmaceutically acceptable salt thereof.

Furthermore, this invention provides a compound of Formulas I, II, or III, or a pharmaceutically acceptable salt thereof for use in therapy, in particular for the treatment of Alzheimer's disease or for the prevention of the progression of mild cognitive impairment to Alzheimer's disease. Even furthermore, this invention provides the use of a compound of Formulas I, II, or III, or a pharmaceutically acceptable salt thereof, for the manufacture of a medicament for the treatment of Alzheimer's disease.

The invention further provides a pharmaceutical composition, comprising a compound of Formulas I, II, or III, or a pharmaceutically acceptable salt thereof, with one or more pharmaceutically acceptable carriers, diluents, or excipients.

In a particular embodiment, the composition further comprises one or more other therapeutic agents. This invention also encompasses novel intermediates and processes for the synthesis of the compounds of Formulas I, II, or III.

Mild cognitive impairment has been defined as a potential prodromal phase of dementia associated with Alzheimer's disease based on clinical presentation and on progression of patients exhibiting mild cognitive impairment to Alzheimer's dementia over time. (Morris, et al., *Arch. Neurol.*, 58, 397-405 (2001); Petersen, et al., *Arch. Neurol.*, 56, 303-308 (1999)). The term "prevention of the progression of mild cognitive impairment to Alzheimer's disease" includes slowing, arresting, or reversing the progression of mild cognitive impairment to Alzheimer's disease in a patient.

As used herein, the terms "treating" or "to treat" includes restraining, slowing, stopping, or reversing the progression or severity of an existing symptom or disorder.

As used herein, the term "patient" refers to a human.

As used herein, the term "C1-C3 alkoxy" refers to methoxy, ethoxy, n-propoxy, and isopropoxy groups.

The term "inhibition of production of Abeta peptide" is taken to mean decreasing of in vivo levels of Abeta peptide in a patient.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of patient; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The compounds of the present invention are generally effective over a wide dosage range. For example, dosages per day normally fall within the range of about 0.01 to about 20 mg/kg of body weight. In some instances dosage levels below the lower limit of the aforesaid range may be more than adequate, while in other cases still larger doses may be employed with acceptable side effects, and therefore the above dosage range is not intended to limit the scope of the invention in any way.

The compounds of the present invention are preferably formulated as pharmaceutical compositions administered by any route which makes the compound bioavailable, including oral and parenteral routes. Most preferably, such compositions are for oral administration. Such pharmaceutical compositions and processes for preparing same are well known in the art. (See, e.g., Remington: The Science and Practice of Pharmacy (D. B. Troy, Editor, 21st Edition, Lippincott, Williams & Wilkins, 2006).

The compounds of Formulas I, II, and III, or pharmaceutically acceptable salts thereof are particularly useful in the treatment methods of the invention, but certain groups, substituents, and configurations are preferred for compounds of Formulas I, II, and III. The following paragraphs describe such preferred groups, substituents, and configurations. It will be understood that these preferences are applicable both to the treatment methods and to the new compounds of the invention.

Thus, for compounds of Formula I, or pharmaceutically acceptable salts thereof:

It is preferred that A is:

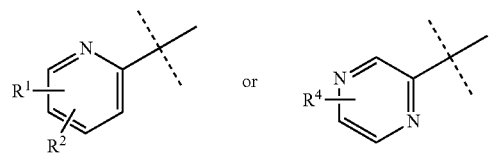

It is further preferred that A is:

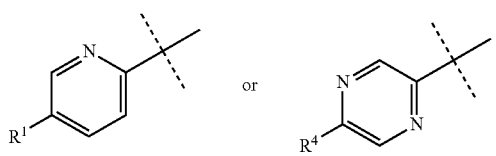

It is especially preferred that A is:

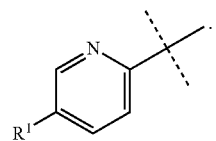

It is preferred that $R^1$ is CN or F, with CN being especially preferred.

It is preferred that $R^2$ is H.

It is especially preferred that when $R^1$ is CN or F, $R^2$ is H.

It is further especially preferred that when $R^1$ is CN, $R^2$ is H.

In addition, it is preferred that $R^3$ is Cl.

It is also preferred that $R^4$ is $OCH_3$.

One of ordinary skill in the art will appreciate that compounds of Formula I are comprised of a core that contains two chiral centers as shown below in Scheme A:

Scheme A

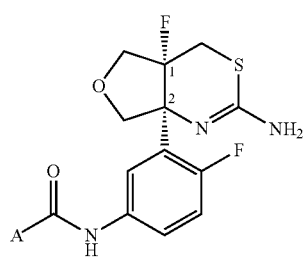

Although the present invention contemplates all individual enantiomers and diastereomers, as well as mixtures of the enantiomers of said compounds, including racemates, the compounds with the absolute configuration at the carbon atoms labeled 1 and 2 as illustrated in Scheme A are preferred compounds of the invention.

For compounds of Formula II, or pharmaceutically acceptable salts thereof:

It is preferred that $R^1$ is CN.

It is preferred that $R^2$ is H.

It preferred that $R^3$ is $OCH_3$.

It further preferred that A is:

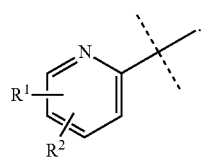

It especially preferred that when $R^1$ is CN, $R^2$ is H.

It is further especially preferred that A is:

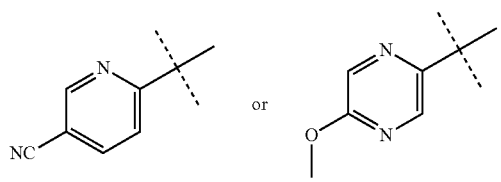

It is further especially preferred that A is:

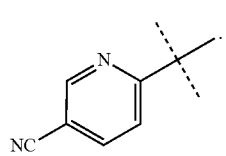

One of ordinary skill in the art will appreciate that compounds of Formula II are comprised of a core that contains two chiral centers as shown below in Scheme B:

Scheme B

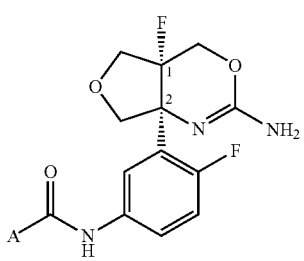

Although the present invention contemplates all individual enantiomers and diastereomers, as well as mixtures of the enantiomers of said compounds, including racemates, the compounds with the absolute configuration at the carbon atoms labeled 1 and 2 as illustrated in Scheme B are preferred compounds of the invention.

and pharmaceutically acceptable salts thereof.

For compounds of Formula III, or pharmaceutically acceptable salts thereof:

It is preferred that A is:

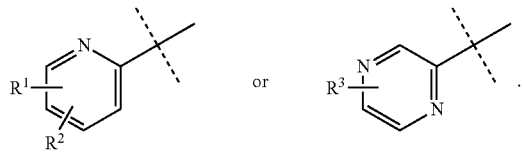

It is further preferred that A is:

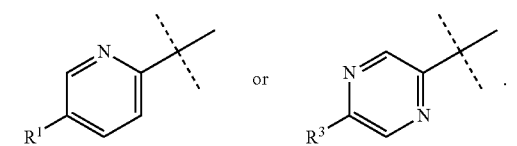

It is especially preferred that A is:

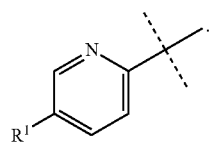

It is most especially preferred that A is:

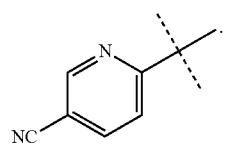

It is preferred that $R^1$ is CN.

It is preferred that $R^2$ is H.

It is further preferred that when $R^1$ is CN, $R^2$ is H.

It is preferred that $R^3$ is $OCH_3$, $CH_2CF_3$,

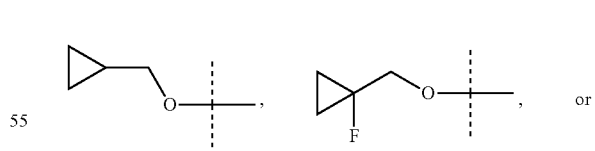

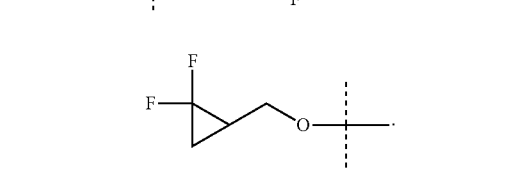

It is especially preferred that $R^3$ is $OCH_3$.

It is preferred that compounds of Formula III are in the (cis)-configuration about the fused rings as shown below:

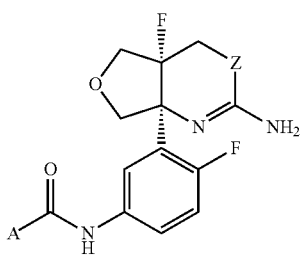

In addition, one of ordinary skill in the art will appreciate that compounds of Formula III are comprised of a core that contains two chiral centers as shown below in Scheme C:

Scheme C

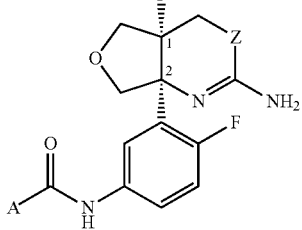

Although the present invention contemplates all individual enantiomers and diasteromers, as well as mixtures of the enantiomers of said compounds, including racemates, the compounds with the absolute configuration at the carbon atoms labeled 1 and 2 as illustrated in Scheme C are preferred compounds of the invention.

Preferred compounds are:

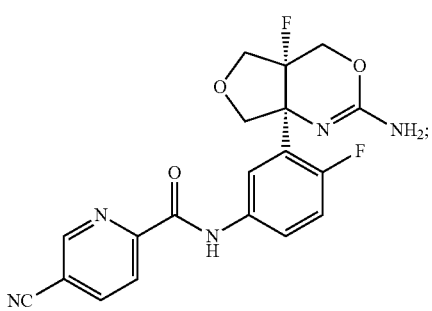

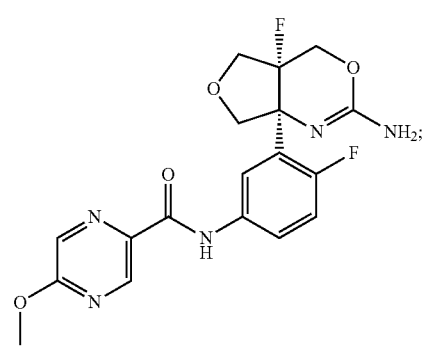

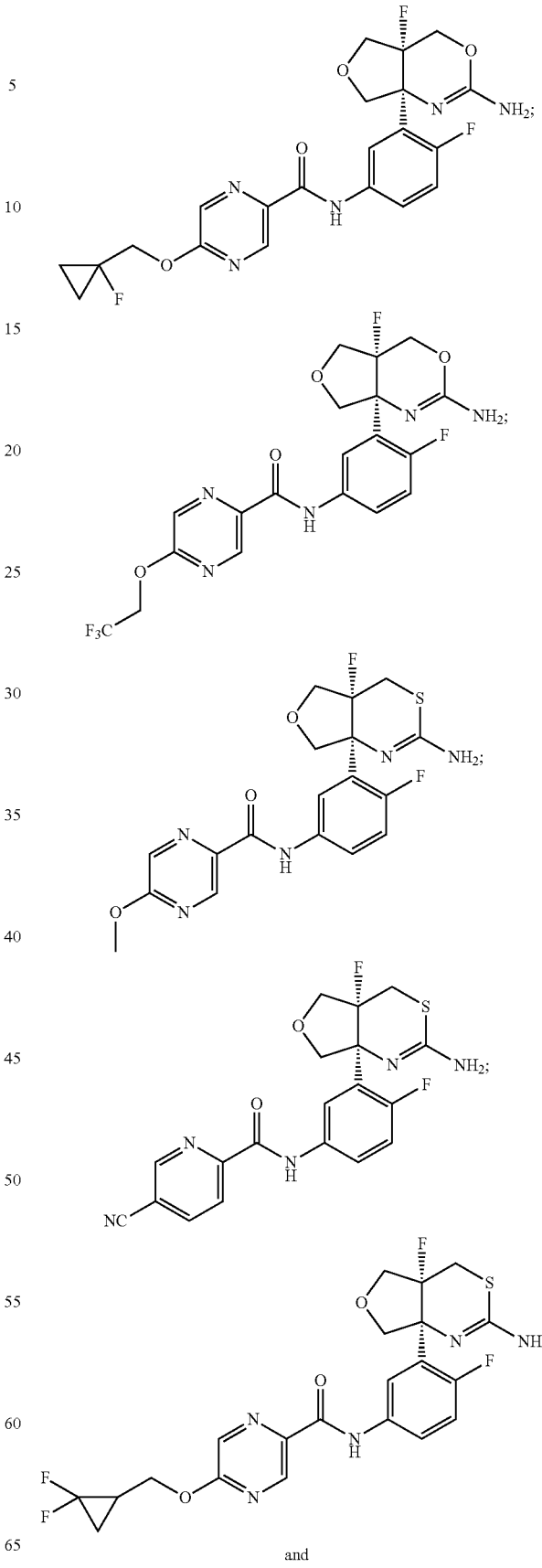

and

-continued

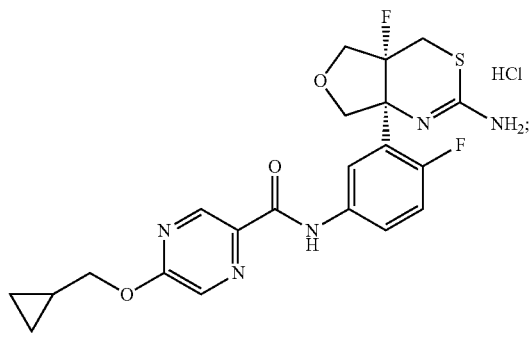

and pharmaceutically acceptable salts thereof.

Most preferred compounds are:

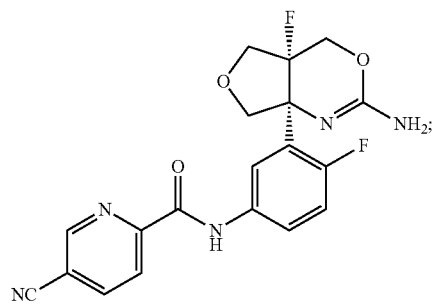

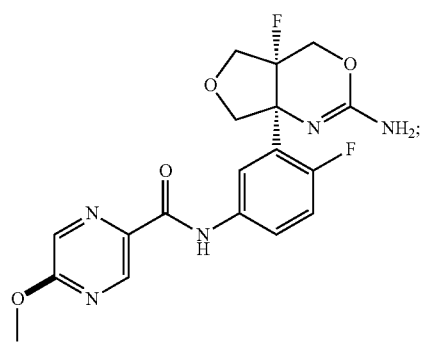

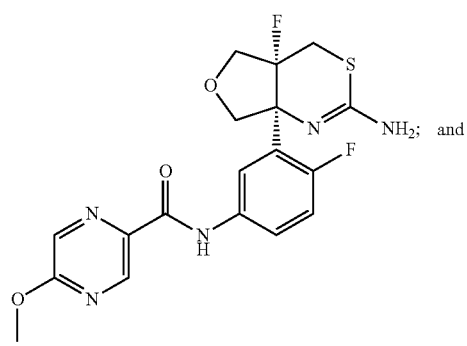

-continued

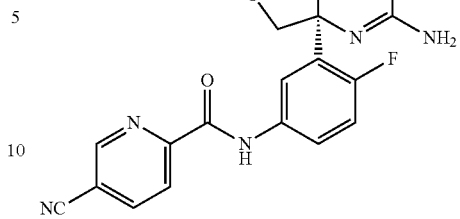

and pharmaceutically acceptable salts thereof.
Especially preferred is:

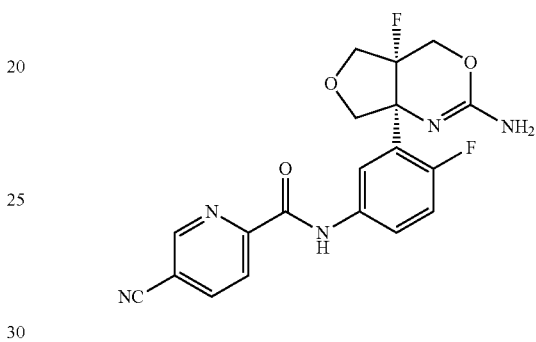

and pharmaceutically acceptable salts thereof.
More particularly, the following compounds are preferred:
N-[3-[(4aR,7aS)-2-amino-4a-fluoro-5,7-dihydro-4H-furo[3,4-d][1,3]oxazin-7a-yl]-4-fluoro-phenyl]-5-cyano-pyridine-2-carboxamide;
N-[3-[(4aR,7aS)-2-amino-4a-fluoro-5,7-dihydro-4H-furo[3,4-d][1,3]oxazin-7a-yl]-4-fluoro-phenyl]-5-methoxy-pyrazine-2-carboxamide;
N-[3-[(4aR,7aS)-2-amino-4a-fluoro-5,7-dihydro-4H-furo[3,4-d][1,3]oxazin-7a-yl]-4-fluoro-phenyl]-5-[(1-fluorocyclopropyl)methoxy]pyrazine-2-carboxamide;
N-[3-[(4aR,7aS)-2-amino-4a-fluoro-5,7-dihydro-4H-furo[3,4-d][1,3]oxazin-7a-yl]-4-fluoro-phenyl]-5-(2,2,2-trifluoroethoxy)pyrazine-2-carboxamide;
N-[3-[(4aR,7aS)-2-amino-4a-fluoro-5,7-dihydro-4H-furo[3,4-d][1,3]thiazin-7a-yl]-4-fluoro-phenyl]-5-methoxy-pyrazine-2-carboxamide;
N-[3-[(4 aR,7aS)-2-amino-4a-fluoro-5,7-dihydro-4H-furo[3,4-d][1,3]thiazin-7a-yl]-4-fluoro-phenyl]-5-cyano-pyridine-2-carboxamide;
N-[3-[(4aR,7aS)-2-amino-4a-fluoro-5,7-dihydro-4H-furo[3,4-d][1,3]thiazin-7a-yl]-4-fluoro-phenyl]-5-[(2,2-difluorocyclopropyl)methoxy]pyrazine-2-carboxamide; and
N-[3-[(4aR,7aS)-2-amino-4a-fluoro-5,7-dihydro-4H-furo[3,4-d][1,3]thiazin-7a-yl]-4-fluoro-phenyl]-5-(cyclopropylmethoxy)pyrazine-2-carboxamide;
and pharmaceutically acceptable salts thereof.
More preferred compounds are
N-[3-[(4aR,7aS)-2-amino-4a-fluoro-5,7-dihydro-4H-furo[3,4-d][1,3]oxazin-7a-yl]-4-fluoro-phenyl]-5-cyano-pyridine-2-carboxamide;
N-[3-[(4aR,7aS)-2-amino-4a-fluoro-5,7-dihydro-4H-furo[3,4-d][1,3]oxazin-7a-yl]-4-fluoro-phenyl]-5-methoxy-pyrazine-2-carboxamide;
N-[3-[(4aR,7aS)-2-amino-4a-fluoro-5,7-dihydro-4H-furo[3,4-d][1,3]thiazin-7a-yl]-4-fluoro-phenyl]-5-methoxy-pyrazine-2-carboxamide; and N-[3-[(4aR,7aS)-2-amino-4a-fluoro-5,7-dihydro-4H-furo[3,4-d][1,3]thiazin-7a-yl]-4-fluoro-phenyl]-5-cyano-pyridine-2-carboxamide;
and pharmaceutically acceptable salts thereof.

An especially preferred compound is N-[3-[(4aR,7aS)-2-amino-4a-fluoro-5,7-dihydro-4H-furo[3,4-d][1,3]oxazin-7a-yl]-4-fluoro-phenyl]-5-cyano-pyridine-2-carboxamide, and pharmaceutically acceptable salts thereof.

One of ordinary skill in the art will appreciate that compounds of the invention can exist in tautomeric forms, as depicted in Scheme D. When any reference in this application to one of the specific tautomers of the compounds of the invention is given, it is understood to encompass both tautomeric forms and all mixtures thereof.

Scheme D

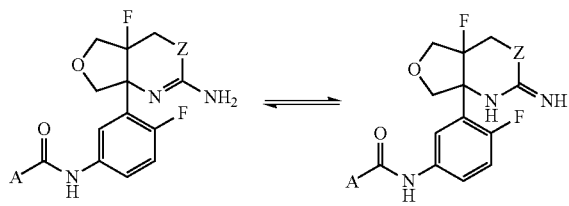

Certain stereochemical centers have been left unspecified and certain substituents have been eliminated in the following schemes for the sake of clarity and are not intended to limit the teaching of the schemes in any way. Furthermore, individual isomers, enantiomers, and diastereomers may be separated or resolved by one of ordinary skill in the art at any convenient point in the synthesis of compounds of Formulas I, II, and III, by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994). The designations "isomer 1" and "isomer 2" refer to the compounds that elute from chiral chromatography first and second, respectively, and if chiral chromatography is initiated early in the synthesis, the same designation is applied to subsequent intermediates and examples.

Additionally, certain intermediates described in the following schemes may contain one or more nitrogen protecting groups. The variable protecting group may be the same or different in each occurrence depending on the particular reaction conditions and the particular transformations to be performed. The protection and deprotection conditions are well known to the skilled artisan and are described in the literature (See for example "*Greene's Protective Groups in Organic Synthesis*", Fourth Edition, by Peter G. M. Wuts and Theodora W. Greene, John Wiley and Sons, Inc. 2007).

Certain abbreviations are defined as follows: "APP" refers to amyloid precursor protein; "CSF" refers to cerebrospinal fluid; "DCC" refers to 1,3-dicyclohexylcarbodiimide; "DIC" refers to diisopropylcarbodiimide; "DIPEA" refers to diisopropylethylamine or N-ethyl-N-isopropyl-propan-2-amine; "ACN" refers to acetonitrile; "DMAP" refers to dimethylaminopyridine; "DMEM" refers to Dulbecco's Modified Eagle's Medium; "DMF" refers to dimethylformamide; "DMSO" refers to dimethyl sulfoxide; "EDCI" refers to 1-(3-dimethylaminopropyl)-3-ethylcarbodiimide hydrochloride; "ee" refers to enantiomeric excess; "Ex" refers to example; "F12" refers to Ham's F12 medium; "FBS" refers to Fetal Bovine Serum; "FRET" refers to fluorescence resonance energy transfer; "HATU" refers to (dimethylamino)-N,N-dimethyl (3H-[1,2,3]-triazolo[4,5-b]pyridin-3-yloxy)methaniminium hexafluorophosphate; "HEK" refers to human embryonic kidney; "HOAc" refers to acetic acid; "HOAt" refers to 1-hydroxy-7-azobenzotriazole; "HOBt" refers to 1-hydroxylbenzotriazole hydrate; "HBTU" refers to refers to 2-(1H-benzotriazole-1-yl)-1,1,3,3-tetramethyluronium hexafluorophosphate; "HPLC" refers to high-performance liquid chromatography; "IC$_{50}$" refers to the concentration of an agent that produces 50% of the maximal inhibitory response possible for that agent; "min" refers to minute or minutes; "MeOH" refers to methanol or methyl alcohol; "MTBE" refers to methyl tert-butyl ether; "PDAPP" refers to platelet derived amyloid precursor protein; "PG" refers to protecting group; "Prep" refers to preparation; "PyBOP" refers to benzotriazol-1-yloxytripyrrolidino-phosphonium hexafluorophosphate; "PyBrop" refers to bromo-tris-pyrrolidino phosphoniumhexafluoro phosphate; "RFU" refers to relative fluorescence unit; "SCX" refers to strong cation exchange; "SFC" refers to supercritical fluid chromatography; and "THF" refers to tetrahydrofuran.

The compounds of the present invention, or salts thereof, may be prepared by a variety of procedures known in the art, some of which are illustrated in the Schemes, Preparations, and Examples below. The specific synthetic steps for each of the routes described may be combined in different ways, or in conjunction with steps from different schemes, to prepare compounds of Formulas I, II, and III, or salts thereof. The products of each step in the schemes below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art.

Scheme 1

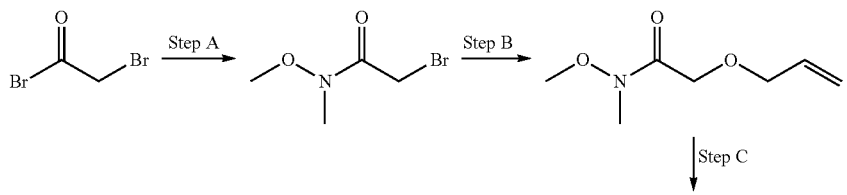

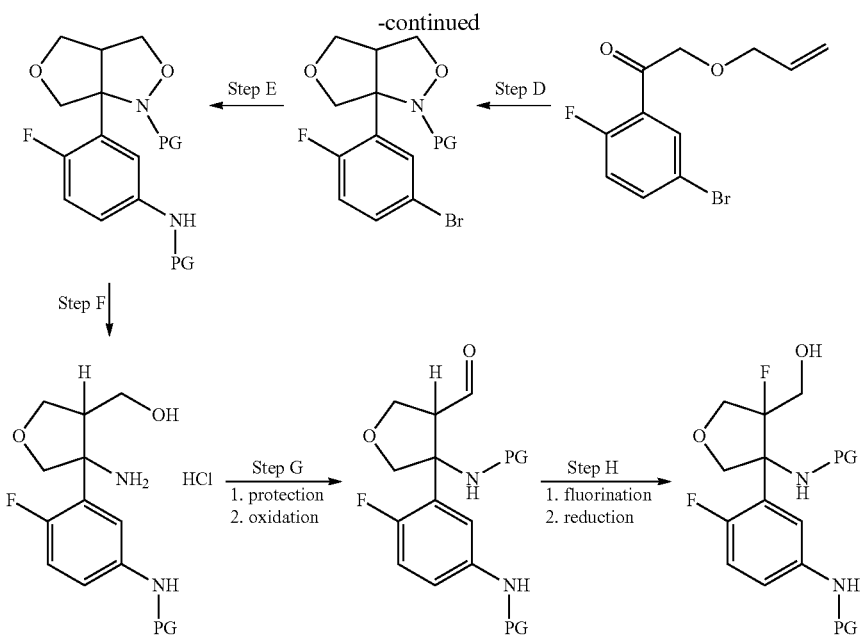

In Scheme 1, step A, bromoacetyl bromide is treated with N,O-dimethylhydroxylamide hydrochloride under conditions well known in the art, using an inorganic base, such as potassium carbonate or an organic base, such as diisopropylethylamine, to provide the Weinreb amide.

In Scheme 1, step B, the Weinreb amide is treated with allyl alcohol and an inorganic base, such as potassium carbonate, under conditions well known in the art to provide the allyl ether. For example, the Weinreb amide is added to about 6-7 equivalents of allyl alcohol and about 2 equivalents of a suitable base, such as potassium carbonate over about 3 hours at about 30° C. The reaction mixture is allowed to stir for about 2 hours at about 30° C., and a suitable organic solvent is added, such as toluene. The mixture is then cooled to about 0° C. and filtered. The filter cake is washed with cold (about 0° C.) toluene, and the organic filtrates combined and rinsed with aqueous potassium bisulfate. The organic phase is then concentrated with additional toluene added to remove water and excess allyl alcohol. The organic is again washed with water and then concentrated to remove most of the toluene. The organic residue is finally distilled to provide the allyl ether.

In Scheme 1, step C, 4-bromo-1-fluoro-2-iodobenzene is reacted with the allyl ether using a Grignard reagent such as isopropylmagnesium chloride to provide the substituted allyloxy ethanone. For example, about 1 equivalent of a suitable Grignard reagent, such as isopropylmagnesium chloride in THF, is add to about 0.95 equivalents of 4-bromo-1-fluoro-2-iodobenzene in a suitable organic solvent, such as THF, at about 0° C. with stirring. After about 60 minutes at about 0° C., about 1 equivalent of the allyl ether in a suitable organic solvent, such as THF is added over about 60 minutes. The reaction is then quenched with excess aqueous ammonium chloride at about 0° C. A suitable organic solvent, such as heptanes, is added to the quenched reaction mixture with stirring as the mixture is warmed to room temperature. The layers are then separated and the organic layer is washed with water, and concentrated with addition of heptanes to remove water and THF, providing the allyloxy ethanone.

In Scheme 1, step D, the bicyclic isoxazole can be formed from the allyloxy ethanone by several methods, such as using a 2-step procedure where an oxime is formed in situ using hydroxylamine, and then cyclized to the bicyclic isoxazolidine (PG=H). Alternatively, a substituted hydroxylamine, such as 1-phenylpropyl hydroxylamine p-toluenesulfonic acid salt is treated with potassium bicarbonate followed by heating with titanium tetraisopropoxide to give a nitrone intermediate in situ that cyclizes to the nitrogen protected bicyclic isoxazole. For example, a suitable 1-phenylpropyl hydroxylamine p-toluenesulfonic acid salt, such as (R)—N-(1-phenylpropyl)hydroxylamine p-toluenesulfonic acid salt (see Patel, I.; Smith, N. A.; Tyler, S, N. G. *Organic Process Research & Development* 2009, 13, 49-53) is treated with about 2.75 equivalents of potassium bicarbonate, water, and a suitable organic solvent, such as MTBE. The layers are separated and the organic layer is washed with aqueous sodium chloride. A suitable organic solvent is added to the organic layer, and most of the MTBE and water are removed by distillation at about 50° C. About 1 equivalent of about a 20-25% weight % solution of the allyloxy ethanone in heptanes is added to the 1-phenylpropyl hydroxylamine in heptanes at about 50° C. About 1.5 equivalents of titanium tetraisopropoxide is then added and the mixture is heated at about 55-60° C. for about 10 hours (Titanium (IV) ethoxide can also be used). The nitrogen protected bicyclic isoxazole is then isolated under conditions well known in the art, such as concentration, cooling, and collection by filtration.

In Scheme 1, step E, the bicyclic isoxazole is converted to the nitrogen protected aniline bicyclic isoxazolidine. For example, about 1 equivalent of the bicyclic isoxazolidine is combined with about 4 equivalents of acetamide, about 0.2 equivalents of a suitable catalyst, such as copper (I) iodide, about 0.7 equivalents of potassium iodide, about 2 equivalents of tripotassium phosphate, and about 0.8 equivalents of N,N-dimethylethylenediamine in a suitable organic solvent, such as DMF. The reaction mixture is then heated at about 110° C. for about 4 hours. The nitrogen protected aniline bicyclic isoxazolidine is isolated using techniques and conditions well known in the art. For example, the reaction mixture is cooled to about 30° C. and portioned between a suitable organic solvent, such as isopropyl acetate and aqueous ammonium chloride. The layers are separated and the aqueous layer is further extracted with isopropyl acetate. The organic extracts are combined, washed with aqueous ammonium chloride, and the organic layer is mixed with a suitable organic solvent, such as xylenes. The organic mixture is then distilled to remove most of the isopropyl acetate and residual DMF. The organic mixture is then cooled to about 0° C. and the resulting solid nitrogen protected aniline bicyclic isoxazolidine is collected by filtration.

In Scheme 1, step F, the nitrogen protected aniline bicyclic isoxazolidine ring can be opened and the isoxazolidine nitrogen also deprotected under standard conditions well known in the art to provide the amino-hydroxymethyl-tetrahydrofuran. For example, about 1 equivalent of the nitrogen protected aniline bicyclic isoxazolidine ring is combined with about 0.2 equivalents zinc chloride and about a 20% weight loading of water wet sulfided 5% palladium on carbon catalyst slurried in a mixture of propanol/water and about 0.9 equivalents HCl. The mixture is heated at about 50° C. under hydrogen at about 300-400 kPa for about 16 hours. The catalyst is then removed by filtration and the filter cake is rinsed with propanol. Most of the water is then removed from the filtrate by azeotropic distillation with additional propanol addition. Additional HCl is added (about 0.1 equivalent) in water and the solid collected to provide the amino-hydroxymethyl-tetrahydrofuran. Alternatively, powdered zinc in HOAc or Raney Ni under hydrogenation conditions can be used to open the isoxazolidine ring.

In Scheme 1, step G, the amino-hydroxymethyl-tetrahydrofuran is first protected with a suitable nitrogen protecting group. The hydroxyl group is subsequently oxidized under conditions well known in the art to provide the aldehyde. For example, the amino-hydroxymethyl-tetrahydrofuran is combined with about 2-3 equivalents of a suitable organic base, such as triethylamine and about 1.2-1.4 equivalents of a suitable nitrogen protecting group reagent, such as di-tert-butyl dicarbonate in a suitable organic solvent, such as THF. The reaction is stirred at about 50° C. for about 15-18 hours and the resulting nitrogen protected intermediate is isolated and purified using techniques well known in the art. For example, the reaction is cooled to room temperature and concentrated. The residue is partitioned between 10% citric acid and ethyl acetate, extracted with ethyl acetate, dried, and concentrated to provide the nitrogen protected intermediate. Alternatively, the reaction is cooled to room temperature, filtered, the solids washed with ethyl acetate, and the filtrate concentrated under reduced pressure. The residue is then purified by chromatography on silica gel, eluting with a suitable eluent, such as methanol:dichloromethane gradient 0:10 to 1:10 to provide the nitrogen protected intermediate of step G, substep 1. The nitrogen protected intermediate is then oxidized to the aldehyde under conditions well known to one of ordinary skill in the art in step G, substep 2. For example, the nitrogen protected intermediate prepared directly above, dissolved in a suitable organic solvent, such as dichloromethane, is added to a stirring mixture of a suitable oxidizing agent, such as about 1.7 equivalents of pyridinium chlorochromate, 4 Å molecular sieves, and about 2.3 equivalents of ammonium acetate in dichloromethane. The suspension is stirred at room temperature for about 35 minutes to about 2 hours. The resulting aldehyde compound of step G, substep 2 is then isolated and purified using techniques well known in the art. For example, the reaction mixture is partially concentrated under reduced pressure, a suitable organic solvent, such as ethyl acetate is added, and the mixture is filtered through silica gel. The silica gel is further rinsed with ethyl acetate, the filtrates are combined, and then concentrated under reduced pressure to provide the aldehyde. Alternatively, to the nitrogen protected intermediate prepared directly above, dissolved in a suitable organic solvent, such as DMSO is added 2-iodoxybenzoic acid (IBX) and the mixture is stirred about 18 hours. The mixture is added to a sodium carbonate aqueous solution, MTBE is added and the mixture is stirred at room temperature for about 15 minutes, filtered through diatomaceous earth and the organic layer is collected, and concentrated to give the aldehyde compound of step G, substep 2.

In Scheme 1, step H, substep 1, the aldehyde of step G is fluorinated using 1-chloromethyl-4-fluoro-1,4-diazoniabicyclo[2.2.2]octane bis(tetrafluoroborate) (also referred to as Selectfluor™) to provide the fluorinated compound, and the aldehyde is then reduced in substep 2 to give the fluorinated primary alcohol. For example, the aldehyde is dissolved in a suitable organic solvent, such as THF and treated with about 1.08 equivalents of a suitable secondary cyclic amine, such as pyrrolidine or D-(+)-proline. The solution is stirred at room temperature for about 5 to 10 minutes and treated with about 1.15 equivalents of Selectfluor™, and the reaction is stirred for about 2 to 3 hours. The reaction is then quenched with saturated aqueous sodium bicarbonate and extracted with suitable organic solvents, such as ethyl acetate and dichloromethane. The organic extracts are combined, dried over a suitable drying agent, such as anhydrous magnesium sulfate or sodium sulfate, filtered, and concentrated under reduced pressure. Alternatively, about 1.1 equivalents of D-(+)-proline is added to a solution of the aldehyde in 2,2,2-trifluoroethanol that is treated with potassium carbonate and 3 Å molecular sieves and filtered prior to use. Other solvents, such as methanol, ethanol, THF, and dichloromethane may also be used, which may produce different diastereoselectivities. 3 Å Molecular sieves (500 mg) are added and the reaction mixture is stirred at room temperature for about 4 hours. About 1.3 equivalents of Selectfluor™ is added to the mixture and it is stirred for about 36 hours. The mixture is concentrated and purified using techniques well known in the art to give the unreduced fluorinated product of step H, substep 1

In step H, substep 2, the residue is dissolved in a suitable organic solvent, such as methanol or ethanol, treated with 1.07-1.4 equivalents of a suitable reducing agent, such as sodium borohydride or sodium tetrahydroborate, and the reaction is then stirred at room temperature for about 30 minutes to 2 hours. The reaction is then quenched with saturated aqueous sodium bicarbonate or evaporated to a residue, and extracted with suitable organic solvents, such as ethyl acetate and dichloromethane. The organic extracts are combined, dried over a suitable drying agent, such as anhydrous magnesium sulfate or sodium sulfate, filtered, and concentrated under reduced pressure to provide the crude fluorinated primary alcohol. This crude material is then purified using techniques well known in the art, such as flash chromatography on silica gel with a suitable eluent, such as a methanol: dichloromethane gradient of 0:10 to 1:10 or ethyl acetate/hexane (1:1) providing the purified fluorinated primary alcohol of step H. Other methods known to one of ordinary skill in the art to accomplish a direct fluorination utilize Selectfluor™, a copper(I) bisimine complex, and anionic phase-transfer catalyst and N-hydroxyphthalimide or N,N-dihydroxypyromellitimide and Selectfluor™. Fluorinating reagents, in addition to Selectfluor™, which may be used, include the following: N-fluoropyridinium trifluoromethanesulfonate and N-fluorobenzenesulfonimide, which may produce different diastereoselectivities.

Scheme 2

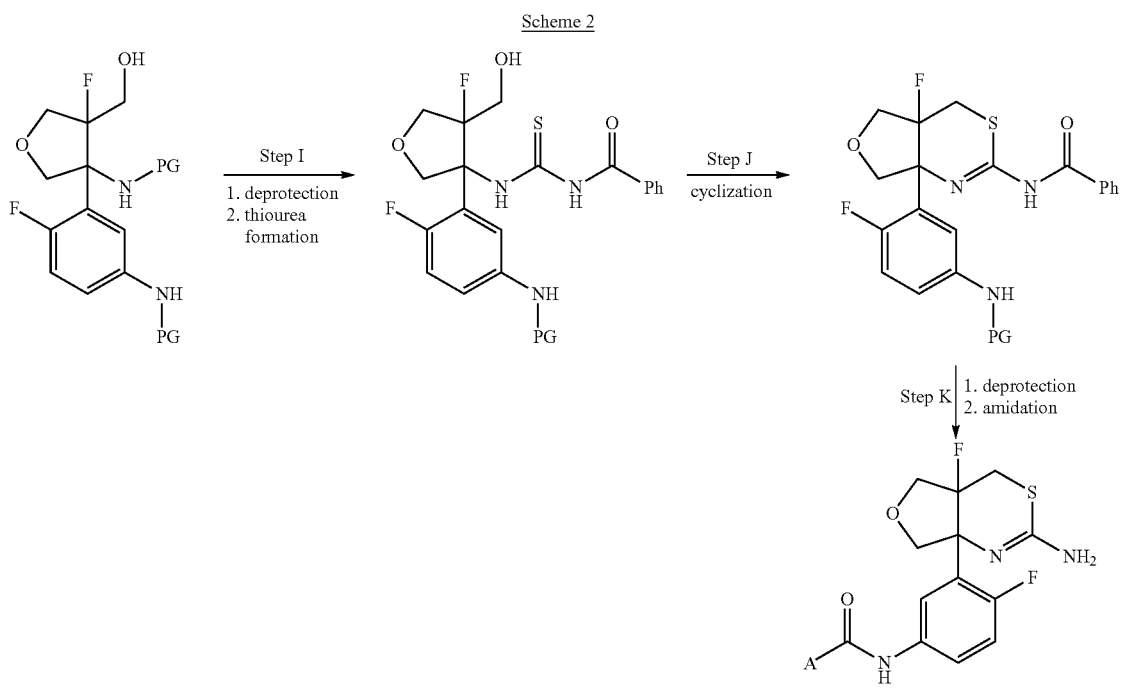

Formula I or Formula IIIa (Z is S)

In Scheme 2, step 1, the fluorinated primary alcohol of step H is deprotected under standard conditions allowing the deprotected amine to then be converted to the thiourea utilizing conditions well known in the art. For example, in substep 1, deprotection, the fluorinated primary alcohol is dissolved in a suitable organic solvent, such as dichloromethane and treated with an excess of a suitable acid such as about 15 equivalents of trifluoroacetic acid. The reaction is stirred at room temperature for about 2 to 3 hours. The reaction is then concentrated under reduced pressure, azeotroping with toluene. In substep 2, thiourea formation, the residue is then dissolved in a suitable organic solvent, such as THF and treated with about 1.1 equivalents of a suitable organic amine, such as triethylamine, and about 1.06 equivalents of benzoyl isothiocyanate. The reaction is then stirred at room temperature for about 16 to 18 hours and then quenched with aqueous saturated sodium bicarbonate. The quenched reaction is then extracted with suitable organic solvents, such as ethyl acetate and dichloromethane. The organic extracts are combined, dried over a suitable drying agent, such as anhydrous magnesium sulfate, filtered, and concentrated under reduced pressure to provide the crude thiourea product of step 1. This crude material is then purified using techniques well known in the art, such as flash chromatography on silica gel with a suitable eluent, such as a methanol:dichloromethane gradient of 0:10 to 1:10 providing the purified thiourea.

In Scheme 2, step J, cyclization, the thiourea of step 1 is cyclized to the protected bicyclic aminothiazine under standard conditions. For example, the thiourea is dissolved in a suitable organic solvent, such as dichloromethane and treated with about 1.44 equivalents of 1-chloro-N,N,2-trimethylpropenylamine. The reaction is then stirred at room temperature for about 3 to 4 hours, and the reaction is quenched with saturated aqueous sodium bicarbonate. The quenched reaction is then extracted with a suitable organic solvent, such as dichloromethane. The organic extracts are combined, dried over a suitable drying agent, such as anhydrous magnesium sulfate, filtered, and concentrated under reduced pressure to provide the crude bicyclic aminothiazine product of step J. The crude material is then purified using techniques well known in the art, such as flash chromatography on silica gel with a suitable eluent, such as an ethyl acetate:hexane gradient of 0:1 to 1:0 providing the purified bicyclic aminothiazine.

In Scheme 2, step K, the bicyclic aminothiazine product of step J is deprotected in substep 1 under conditions well known in the art, and then in substep 2, an amidation is carried out under conditions well known in the art with a suitable aryl acyl chloride (A-(C=O)—Cl), wherein "A" is as defined herein, to provide the compounds of Formula I or Formula IIIa, (Z is S). For example, the bicyclic aminothiazine is combined with about 5.6 equivalents of O-methylhydroxylamine hydrochloride and about 5.9 equivalents of pyridine in a suitable organic solvent, such as ethanol, and heated at about 50° C. for about 16 hours. Then about 25 equivalents of a suitable acid, such as concentrated hydrochloric acid is added and the reaction is heated at about 50° C. for an additional 24 hours. The reaction is then cooled and concentrated under reduced pressure to provide the crude deprotected diamino compound which is then purified by techniques well known in the art, such as flash chromatography on silica gel eluting with a suitable eluent, such as 7 M ammonia in methanol/dichloromethane gradient 0:10 to 1:10 to provide the purified deprotected diamino compound.

Alternatively, the bicyclic aminothiazine product of step J is combined with about 9.4 equivalents of O-methylhydroxylamine hydrochloride and about 9.9 equivalents of pyridine in a suitable organic solvent, such as ethanol, and heated at about 50° C. for about 18 hours. The reaction is then purified directly, for example, by use of an SCX column, utilizing a suitable eluent, such as in methanol followed by 7 M ammonia in methanol. The purified material is then dissolved in a suitable organic solvent, such as ethanol, treated with about 16 equivalents of a suitable acid, such as concentrated hydrochloric acid and heated at 50° C. for about 23 hours. The reaction is then cooled and concentrated under reduced pressure to provide the crude deprotected diamino compound which can be purified by techniques well known in the art, such as flash chromatography or an SCX column utilizing a suitable eluent, such as methanol followed by 7 M ammonia in methanol.

The deprotected diamino can then be amidated in step K, substep 2 under conditions well known in the art, using for example, an aryl acyl chloride to provide compounds of Formula I or Formula IIIa. For example, 2 equivalents of oxalyl chloride is added to 2.2 equivalents DMF in a suitable organic solvent, such as acetonitrile, and the reaction is stirred for about 10 minutes. About 2.05 equivalents of the appropriately substituted aryl carboxylic acid (A-CO$_2$H) is added to the reaction which is allowed to stir for about 30 to 60 minutes producing about 2 equivalents of the corresponding aryl acyl chloride. About 1 to 2 equivalents of the freshly prepared aryl acyl chloride is added drop wise to a solution of the deprotected diamino compound, prepared above, in ethanol:water (about 1:1 vol) at about 50° C. The reaction is heated at 50° C. for about 45 to 90 minutes. The resulting compound of Formula I or Formula IIIa is then isolated and purified using techniques and conditions well known in the art. For example, the reaction mixture is combined with saturated aqueous sodium bicarbonate and extracted with a suitable organic solvent, such as dichloromethane. (The reaction mixture can also be loaded on an SCX column directly, purified, and then further purified by silica gel.) The organic layers are combined, washed with brine, and concentrated under reduced pressure to provide the crude material for Formula I or Formula IIIa. The crude material can then be purified, for example, by flash chromatography on silica gel using a suitable eluent, such as 7 M ammonia in methanol/dichloromethane gradient of 0:10 to 1:10. The purified material can be further purified by reverse phase flash chromatography using a high resolution C18 column eluting with a suitable eluent, such as 5 to 60% gradient of acetonitrile in 10 mM ammonium bicarbonate aqueous solution with 5% methanol. The eluent containing product is then extracted with 4:1 chloroform:isopropanol. The organic extracts are combined, washed with brine, dried over anhydrous magnesium sulfate, filtered, and concentrated under reduced pressure to provide the further purified compounds of Formula I or Formula IIIa as a free base.

Alternatively one skilled in the art will recognize that there are a number of methods and reagents for amide formation resulting from the reaction of carboxylic acids and amines. For example, the reaction of the deprotected diamino compound with an appropriate aryl carboxylic acid (A-CO$_2$H) in the presence of a coupling reagent and an amine base, such as DIPEA or triethylamine, will provide a compound of Formula I or Formula IIIa. Coupling reagents include carbodiimides, such as DCC, DIC, EDCI, and aromatic coupling reagents, such as HOBt and HOAt. Additionally, uronium or phosphonium salts of non-nucleophilic anions, such as HBTU, HATU, PyBOP, and PyBrOP can be used in place of the more traditional coupling reagents. Additives such as DMAP may be used to enhance the reactions and provide compounds of Formula I or Formula IIIa.

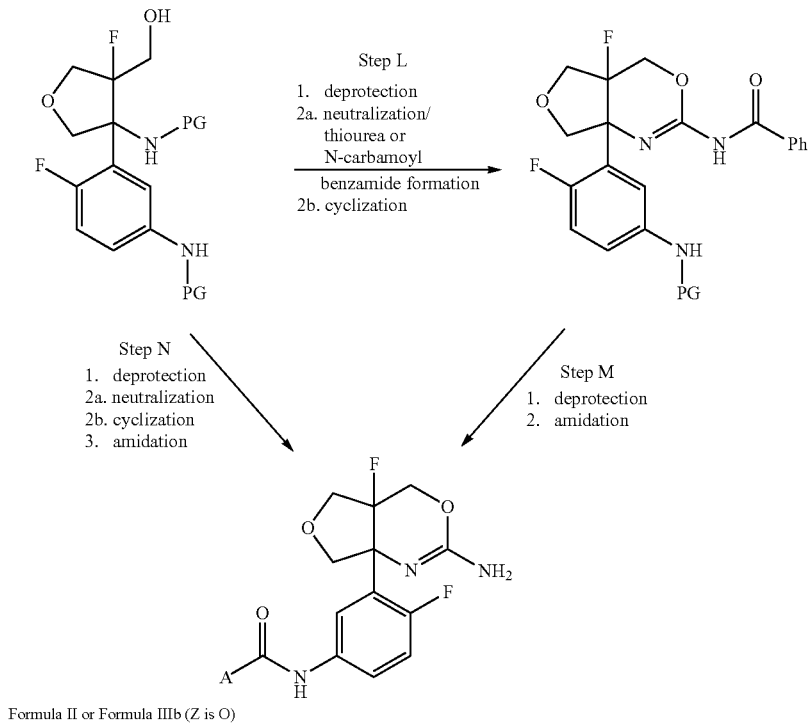

In Scheme 3, step L, substep 1, the fluorinated primary alcohol (prepared in Scheme 1, step H) is deprotected under standard conditions followed by neutralization, thiourea formation and cyclization in substeps 2a and 2b to provide the protected bicyclic aminooxazine. For example, in substep 1, the fluorinated primary alcohol is dissolved in a suitable organic solvent, such as ethyl acetate or dichloromethane and treated with an excess of a suitable acid such as hydrochloric acid (4 M in 1,4-dioxane) or trifluoroacetic acid. The reaction is stirred at room temperature for about 2 hours to overnight. The deprotected amine is then isolated with techniques well known in the art such as filtration as a salt. Alternatively for substep 1, ethanol is added drop wise to a solution of excess acetyl chloride in ethyl acetate at about 0° C. and stirring for about 30 minutes. The fluorinated primary alcohol, (Scheme 1, step H) is added and the reaction is stirred overnight at room temperature. The deprotected amine salt is then isolated with techniques well known in the art such as filtration. Then, for the neutralization and thiourea formation for substep 2a, the deprotected amine salt is dissolved in a suitable organic solvent, such as acetonitrile or tetrahydrofuran and treated with about 1.1 equivalents of a suitable organic amine, such as triethylamine to neutralize the amine, and about 1.05 equivalents of benzoyl isothiocyanate is added to form the intermediate thiourea. The reaction is then stirred at 5° C. for about 1 hour or heated to about 70° for 2 hours. To cyclize and form the protected bicyclic aminooxazine in substep 2b, about 1.1 equivalents of trimethylsilyl chloride and DMSO are added and stirring is continued for about 2 hours. The reaction is quenched with potassium phosphate dibasic (20%) to adjust the pH to 7-8 and the product is isolated using techniques well known in the art to give the protected bicyclic aminooxazine product of step L. Alternatively, the amine salt can be neutralized with triethylamine as described above for step L, step 2a, and treated with benzoylcarbamate to form an N-carbamoyl benzamide intermediated that is then cyclized with diethylaminosulfur trifluoride in an organic solvent such as dichloromethane at about −78° C. and warmed to about room temperature over 1 hour. The product is isolated using techniques well known in the art to give the protected bicyclic aminooxazine product of step L.

In Scheme 3, step M, deprotection of the protected bicyclic aminooxazine is first completed and then the aniline is deprotected under conditions well known in the art, followed by amidation of the aniline in substep 2 with a suitable aryl acyl chloride-A, wherein "A" is as defined herein, to provide compounds of Formula II or Formula IIIb (Z is O). For example, in step M, substep 1, the protected bicyclic aminooxazine is added to a solution of about 1.1 equivalents of lithium hydroxide in methanol and heated to 40° C. for about 18 hours to deprotect the amino group on the bicyclic aminooxazine. The aniline is then deprotected under conditions well known in the art such as acidic conditions using aqueous 1 M hydrogen chloride and heating to 90° C. for about 3 hours. The reaction is then cooled, diluted with ethyl acetate, and the aqueous layer separated and treated with aqueous sodium hydroxide solution to adjust the pH to about 10. This mixture is then extracted with ethyl acetate, and concentrated under reduced pressure to provide the deprotected crude diamino compound. The deprotected crude diamino compound is then purified by techniques well known in the art, such as flash chromatography on silica gel eluting with a suitable eluent, such as 7 M ammonia in methanol/dichloromethane gradient to provide the purified deprotected diamino compound.

Then, in Scheme 3, step M, substep 2, the deprotected diamino compound is amidated at the aniline nitrogen under conditions well known in the art, using for example an aryl acyl chloride to provide compounds of Formula II or Formula IIIb. For example, about 1 equivalent of oxalyl chloride and a catalytic amount of DMF is added to about 1.07 equivalents of the aryl carboxylic acid (A-CO$_2$H) in a suitable organic solvent such as acetonitrile and the mixture is stirred for about 10 minutes. This mixture is then added to a 50° C. solution of the deprotected diamino compound in ethanol and water and is stirred at about 50° C. for about 10 minutes. The resulting compound of Formula II or Formula IIIb is then isolated and purified using techniques and conditions well known in the art. For example, the reaction mixture is combined with saturated aqueous sodium bicarbonate and extracted with a suitable organic solvent, such as ethyl acetate. The crude material can then be purified, for example, by flash chromatography on silica gel using a suitable eluent, such as a gradient of 7 M ammonia in methanol/dichloromethane to provide the compound of Formula II or Formula IIIb as a free base.

Alternatively, in Scheme 3, step N, substep 1, the fluorinated primary alcohol of Scheme 1, step H can be deprotected as described above for step L, substep 1, neutralized and cyclized in substeps 2a and 2b without first protecting the amine, and amidated in substep 3 under conditions well known in the art. For example, the amine can be deprotected in substep 1 under acidic conditions well known in the art using an excess of a suitable acid such as hydrochloric acid (4 M in 1,4-dioxane) or trifluoroacetic acid. The deprotected amine, as an HCl salt, is then isolated with techniques well known in the art such as filtration. The protected aniline, hydroxyl HCl amine is neutralized in substep 2b by dissolving it in a suitable organic solvent such as dichloromethane and treated with about 1.2 equivalents of an organic base such as triethylamine, stirred for about 10 minutes, and concentrated. Ethyl acetate is added and the mixture is heated to 40° C. for about 10 minutes followed by concentration to ensure complete neutralization. Cyclization is completed in substep 2b by adding ethanol and cyanogen bromide to the residue and the mixture is heated to about 120° C. for about 4 hours. Following evaporation of the solvent, the residue is dissolved in water and 1.0 M hydrochloric acid and washed with ethyl acetate. The aqueous extract is treated with concentrated aqueous hydrochloric acid and stirred at 50° C. for about 48 hours. The mixture is cooled, the pH adjusted to basic with aqueous sodium hydroxide and extracted with ethyl acetate. Purification of the crude aniline amino bicyclic oxazine can be accomplished with silica gel flash chromatography eluting with a gradient such as 7 M ammonia in methanol and dichloromethane. In step N, substep 3, this material can be amidated at the aniline amine as described above in step M, substep 2 to give the compound of Formula II or Formula IIIb.

Alternatively one skilled in the art will recognize that there are a number of methods and reagents for amide formation resulting from the reaction of carboxylic acids and amines as described previously under Scheme 2 and can be applied to Scheme 3 also.

A pharmaceutically acceptable salt of a compound of Formulas I, II and III, such as a hydrochloride salt, can be formed by reaction of an appropriate free base of Formulas I, II, or III (including IIIa and IIIb) with an appropriate pharmaceutically acceptable acid in a suitable solvent under standard conditions well known in the art. Additionally, the formation of such salts can occur simultaneously upon deprotection of a nitrogen protecting group. The formation of such salts is well known and appreciated in the art. See, for example, Gould, P. L., "Salt selection for basic drugs," *International Journal of Pharmaceutics,* 33: 201-217 (1986); Bastin, R. J., et al. "Salt Selection and Optimization Procedures for Pharmaceutical New Chemical Entities," *Organic Process Research and Development,* 4: 427-435 (2000); and Berge, S. M., et al., "Pharmaceutical Salts," *Journal of Pharmaceutical Sciences,* 66: 1-19, (1977).

The following preparations and examples further illustrate the invention.

PREPARATION 1

2-(Allyloxy)-N-methoxy-N-methylacetamide

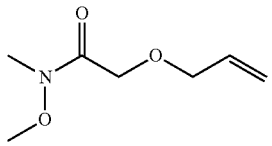

Scheme 1, steps A and B: Bromoacetyl bromide (1.06 equiv.) is added to a solution of N,O-dimethylhydroxylamine hydrochloride (1.0 equiv.) (Volumes are in mL/g of this compound) in a stirring mixture of water (4 mL/g), toluene (4 mL/g), and $K_2CO_3$ (1.15 equiv.) at 0° C. After warming to room temperature over 1 hour, the layers are separated and the aqueous layer is extracted with toluene (2 mL/g). The combined organic layers are concentrated to give the intermediate 2-bromo-N-methoxy-N-methyl-acetamide containing about 20% toluene. 2-Bromo-N-methoxy-N-methyl-acetamide is added to a mixture of allyl alcohol (6.3 equiv) and $K_2CO_3$ (2 equiv.) over 3 hours at 30° C. After 2 hours at 30° C., toluene (4 mL/g) is added, the mixture is cooled to 0° C., and filtered. The filter cake is rinsed with cold (0° C.) toluene (2.7 mL/g) and the combined filtrate is washed with a 3 weight % solution of $KHSO_4$ in water (0.6 mL/g). The toluene solution is concentrated while additional toluene (11 mL/g) is added to remove water and allyl alcohol. The concentrated toluene solution is washed with water (0.5 g/g), further concentrated to remove most of the toluene, and then distilled to give the title compound. LC-MS (m/z): 160 (M+H).

PREPARATION 2

(3aS,6aS)-6a-(5-Bromo-2-fluorophenyl)-1-((R)-1-phenylpropyl)hexahydrofuro[3,4-c]isoxazole

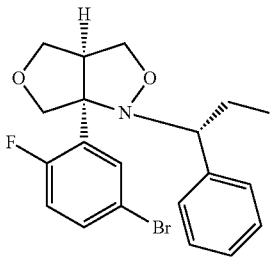 [SMILES: CC[C@H](c1ccccc1)N1OC[C@@H]2COC[C@@]21c1cc(Br)ccc1F]

Scheme 1, steps C and D: To 4-bromo-1-fluoro-2-iodobenzene (0.95 equiv.) in THF (4.6 mL/g) at 0° C. is added isopropylmagnesium chloride (1.0 equiv, 20 weight percent in THF). After about 60 minutes at 0° C., a solution of 2-(allyloxy)-N-methoxy-N-methylacetamide (1.0 equiv.) (Volumes for this stage are in mL/g of this compound) in THF (2.2 mL/g) is added over about 60 minutes. The reaction mixture is quenched into a solution of $NH_4Cl$ (4.3 equiv.) in water (5.8 mL/g) at 0° C. Heptanes (7.2 mL/g) is added as the mixture is warmed to room temperature, and the layers are separated. The organic layer is washed with water (7.2 mL/g). The organic layer is concentrated while additional heptanes (4 mL/g) is added to remove water and THF. The intermediate, 2-allyloxy-1-(5-bromo-2-fluoro-phenyl)ethanone is obtained as a solution in heptanes (approximately 20-25 weight %).

(R)—N-(1-Phenylpropyl)hydroxylamine p-toluenesulfonic acid salt is treated with $KHCO_3$ (2.75 equiv.), water (6.6 mL/g), and methyl tert-butylether (6.8 mL/g). The layers are separated and the organic layer is washed with a 25 weight % solution of NaCl (2.8 mL/g) in water. Heptanes (12 mL/g) is added and most of the MTBE and water are removed by distillation at about 50° C. A 20-25 weight % solution of 2-allyloxy-1-(5-bromo-2-fluoro-phenyl) ethanone (1 equiv., volumes for this stage are in mL/g of this compound) in heptanes is added to the (R)—N-(1-phenylpropyl)hydroxylamine heptanes mixture at 50° C. Titanium tetraisopropoxide (1.5 equiv.) is added and the mixture is heated at about 55-60° C. for about 10 hours. The mixture is concentrated at about 35-50° C. while additional heptanes (6 mL/g) is added. The distillation is stopped when the total volume is about 5 mL/g compared to the expected product yield of 60%. The mixture is cooled to -10° C., the solids are collected by filtration, rinsed twice with cold (-10° C.) heptanes (1 mL/g) and dried to give the title compound. LC-MS (m/z for $^{79}$Br/$^{81}$Br): 406/408 (M+H).

PREPARATION 3

N-(4-Fluoro-3-((3aS,6aS)-1-((R)-1-phenylpropyl)hexahydrofuro[3,4-c]isoxazol-6a-yl)phenyl)acetamide

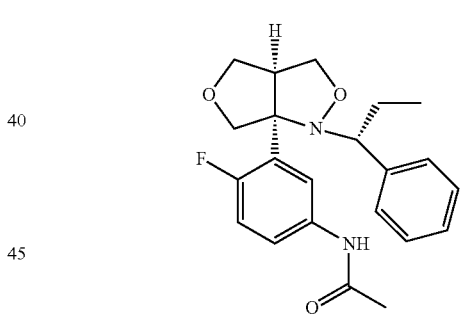

Scheme 1, step E: A mixture of (3aS,6aS)-6a-(5-bromo-2-fluorophenyl)-1-((R)-1-phenylpropyl)hexahydrofuro[3,4-c]isoxazole (1.0 equiv., volumes are in mL/g of this compound), acetamide (4 equiv.), copper (I) iodide (0.2 equiv.), potassium iodide (0.7 equiv.), $K_3PO_4$ (2.0 equiv.), N,N-dimethylethylenediamine (0.8 equiv.) and DMF (4 mL/g) is heated at 110° C. for about 4 hours. After cooling to 30° C., the mixture is partitioned between isopropyl acetate (3.7 mL/g) and 10 weight % $NH_4Cl$ (5.7 mL/g) in water. The layers are separated and the aqueous layer is extracted with isopropyl acetate (2 mL/g). The combined organic layers are washed twice with 10 weight % $NH_4Cl$ (1 mL/g) in water. The organic layer is mixed with xylenes (4.3 mL/g), and the mixture is distilled under vacuum to remove most of the isopropyl acetate and residual DMF. The mixture is cooled to 0° C., the solids are collected by filtration, rinsed twice with xylenes (0.7 mL/g) and dried to give the title compound. LC-MS (m/z): 385 (M+H).

PREPARATION 4

N-(3-((3S,4R)-3-Amino-4-(hydroxymethyl)tetrahydrofuran-3-yl)-4-fluorophenyl)acetamide hydrochloride

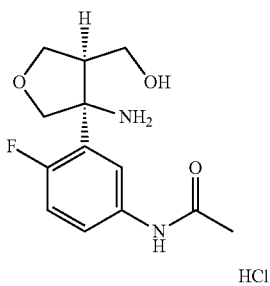 [SMILES: CC(=O)Nc1ccc(F)c([C@]2(N)COC[C@H]2CO)c1 ; Cl]

HCl

Scheme 1, step F: A mixture of N-(4-fluoro-3-((3aS,6aS)-1-((R)-1-phenylpropyl)hexahydrofuro[3,4-c]isoxazol-6a-yl)phenyl)acetamide (1.0 equiv., volumes are in mL/g of this compound), zinc chloride (0.2 equiv), and a 20% weight loading of water wet, sulfided 5% Pd/C catalyst is slurried in a mixture 1-propanol (4 mL/g), water (3.8 mL/g), and HCl (0.9 equiv, 33 weight % in water). The mixture is heated at 50° C. under hydrogen pressure (about 300-400 kPa) for about 16 hours. The catalyst is removed by filtration at about 50° C. and the filter cake is rinsed with 1-propanol (2.9 mL/g). Most of the water is removed from combined filtrates by azeotropic distillation using additional 1-propanol (10.5 mL/g). Additional HCl (0.1 equiv., 33 weight % in water) is added to the mixture and the solids are collected by filtration, rinsed twice with 1-propanol (1 mL/g) and dried to give the title compound. LC-MS (m/z): 269 (M+H).

PREPARATION 5 tert-Butyl N-[(3S,4R)-3-(5-acetamido-2-fluoro-phenyl)-4-(hydroxymethyl)tetrahydrofuran-3-yl]carbamate Method A

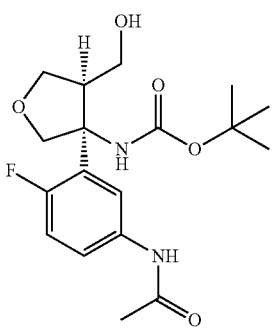

Scheme 1, step G substep 1 (protection): A solution of N-[3-[(3S,4R)-3-amino-4-(hydroxymethyl)tetrahydrofuran-3-yl]-4-fluoro-phenyl]acetamide hydrochloride (60.0 g, 197 mmol), triethylamine (85.0 mL, 610 mmol) and di-tert-butyl dicarbonate (60.0 g, 272 mmol) in tetrahydrofuran at 50° C. is stirred for 15.5 hours. The reaction is cooled to ambient temperature, filtered, washed with ethyl acetate, and concentrated under reduced pressure. The residue is purified by silica gel flash chromatography, eluting with methanol/dichloromethane (0:10) to methanol/dichloromethane (1:10) to give the title compound (71.0 g, 98%). ES/MS (m/e): 269 (M−99).

Method B Preparation 5

Di-tert-butyldicarbonate (130 g, 591 mmol) is added to a solution of N-(3-((3S,4R)-3-amino-4-(hydroxymethyl)tetrahydrofuran-3-yl)-4-fluorophenyl)acetamide hydrochloride (150 g, 492 mmol) and triethylamine (137 mL, 984 mmol) in THF (1.2 L). After stirring at 50° C. under nitrogen for 18 hours, the reaction mixture is gradually cooled to room temperature and the solvent is evaporated. The residue is partitioned between 10% citric acid aqueous solution (500 mL) and ethyl acetate (1 L). The layers are separated and the aqueous layer is extracted with ethyl acetate (2×150 mL). The organic layers are combined, dried over sodium sulfate, filtered and concentrated under reduced pressure to give a residue which is dried under vacuum to constant weight to give the title compound (192 g, 95.3%). ES/MS (m/z): 367 (M+1), 267 (M−99); $^1$H NMR (300.16 MHz, CDCl$_3$) δ 7.85-7.79 (m, 1H), 7.60-7.56 (m, 1H), 7.41-7.36 (m, 1H), 7.26 (d, J=1.0 Hz, 7H), 7.04-6.95 (m, 2H), 4.26-4.11 (m, 2H), 3.80-3.72 (m, 3H), 2.15 (s, 5H), 2.05 (d, J=0.8 Hz, 1H), 1.72-1.67 (m, 1H), 1.36 (s, 13H), 1.31-1.26 (m, 3H).

PREPARATION 6 tert-Butyl N-[(3S,4S)-3-(5-acetamido-2-fluoro-phenyl)-4-formyl-tetrahydrofuran-3-yl]carbamate Method A

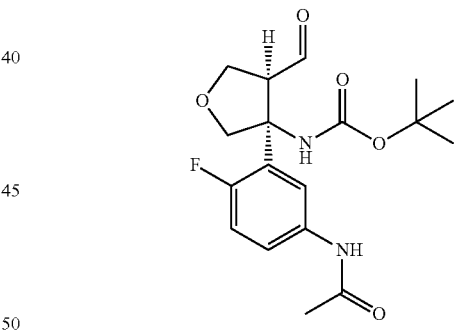

Scheme 1, step G, substep 2 (oxidation): A mixture of pyridinium chlorochromate (10.0 g, 45.5 mmol), 4 Å molecular sieves (20.0 g) and ammonium acetate (5.00 g, 62.3 mmol) are grinded into a fine powder and added to dichloromethane (150 mL). A solution of tert-butyl N-[(3S,4R)-3-(5-acetamido-2-fluoro-phenyl)-4-(hydroxymethyl)tetrahydrofuran-3-yl]carbamate (10.0 g, 27.1 mmol) in dichloromethane (100 mL) is then added. The resulting suspension is stirred at ambient temperature for 35 minutes and is concentrated under reduced pressure to approximate 100 mL volumes of dichloromethane. Ethyl acetate (200 mL) is then added, and the resulting mixture is filtered through a silica gel cake. The cake is washed with ethyl acetate, and the combined filtrate is concentrated under reduced pressure to give the title compound (71.0 g, 98%), which is used without further purification. ES/MS (m/e): 267 (M−99).

Method B Preparation 6

2-Iodosobenzoic acid (45% w/w, 88.3 g, 142 mmol) is added portion wise to a solution of tert-butyl N-[(3S,4R)-3-(5-acetamido-2-fluoro-phenyl)-4-(hydroxymethyl)tetrahydrofuran-3-yl]carbamate (50.0 g, 129 mmol) in DMSO (200 mL) at room temperature. After stirring at 22° C. for 18 hours, the reaction mixture is added to a sodium carbonate aqueous solution (500 mL) keeping the temperature below 25° C. Methyl-t-butyl ether is added (500 mL) and the mixture is stirred at room temperature for 15 minutes. The mixture is filtered through diatomaceous earth and the organic layer is separated. The aqueous layer is extracted with methyl-t-butyl ether (2×100 mL). The organic layers are combined, dried over sodium sulfate, filtered, and concentrated under reduced pressure to give a residue. The residue is dried under vacuum to a constant weight (46.0 g, 93.5%). This material is used without further purification. ES/MS (m/z): 267 (M−99). $^1$H NMR (300.16 MHz, CDCl$_3$) δ 9.87 (d, J=2.8 Hz, 1H), 9.44 (t, J=2.2 Hz, 1H), 7.63-7.55 (m, 3H), 7.43-7.31 (m, 2H), 7.26 (s, 3H), 7.04-6.98 (m, 2H), 5.30 (s, 1H), 4.49-4.28 (m, 5H), 4.12-4.06 (m, 2H), 3.75 (td, J=7.6, 2.6 Hz, 1H), 3.21 (s, 4H), 2.62 (s, 1H), 2.15 (d, J=4.4 Hz, 6H), 1.63 (s, 4H), 1.36-1.31 (m, 18H), 1.19 (s, 11H).

PREPARATION 7 tert-Butyl N-[(3S,4S)-3-(5-acetamido-2-fluoro-phenyl)-4-fluoro-4-(hydroxymethyl)tetrahydrofuran-3-yl]carbamate Method A

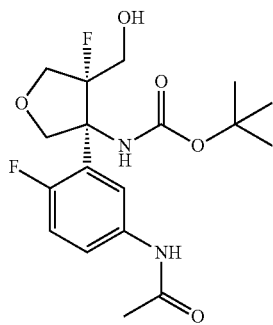 [SMILES: CC(=O)Nc1ccc(F)c([C@]2(NC(=O)OC(C)(C)C)COC[C@@]2(F)CO)c1]

Scheme 1, step H, substeps 1 and 2 (fluorination and reduction): A solution of tert-butyl N-[(3S,4S)-3-(5-acetamido-2-fluoro-phenyl)-4-formyl-tetrahydrofuran-3-yl]carbamate (9.0 g, 24.56) in tetrahydrofuran (100 mL) is treated with pyrrolidine (2.20 mL, 26.4 mmol). The resulting solution is stirred at ambient temperature for 7 minutes and is treated with 1-chloromethyl-4-fluoro-1,4-diazoniabicyclo[2.2.2]octane bis(tetrafluoroborate) (10.0 g, 28.2 mmol). The reaction is stirred at ambient temperature for 160 minutes, then is quenched with a solution of saturated sodium bicarbonate in water, and is extracted with ethyl acetate and dichloromethane consecutively. The organic layers are combined, dried over magnesium sulfate, filtered, and concentrated under reduced pressure to give a residue. The residue is dissolved in methanol (100 mL) and sodium borohydride (1.00 g, 26.2 mmol) is added in a single portion to the solution. The resulting reaction is stirred at ambient temperature for 37 minutes, quenched with a solution of saturated sodium bicarbonate in water, and extracted with dichloromethane and ethyl acetate consecutively. The organic layers are combined, dried, filtered, and concentrated under reduced pressure to give a residue. The residue is purified by silica gel flash chromatography, eluting with methanol/dichloromethane (0:10) to methanol/dichloromethane (1:10) to give the title compound (2.70 g, 28%). ES/MS (m/e): 287 (M−99).

Method B Preparation 7

D-(+)-Proline (691 mg, 6.00 mmol) is added in a single portion to a solution of tert-butyl N-[(3S,4S)-3-(5-acetamido-2-fluoro-phenyl)-4-formyl-tetrahydrofuran-3-yl]carbamate (2.00 g, 5.46 mmol) in 2,2,2-trifluoro-ethanol (16 mL, treated with potassium carbonate and 3 Å molecular sieves, and filtered prior to use). 3 Å Molecular sieves (500 mg) are added and the reaction mixture is stirred at room temperature for 4 hours. To the reaction mixture is added 1-(chloromethyl)-4-fluoro-1,4-diazoniabicyclo[2.2.2]octane bis(tetrafluoroborate) (2.51 g, 7.10 mmol) in a single portion and the mixture is stirred at room temperature for 36 hours. The solvent is concentrated under vacuum and the residue is partitioned between water (25 mL) and ethyl acetate (25 mL). Sodium bicarbonate (7% aqueous solution) is added to adjust pH=8 and the organic layer is separated. The aqueous layer is extracted with ethyl acetate (2×15 mL). The organic layers are combined, dried over sodium sulfate, filtered, and concentrated under reduced pressure. The residue is dissolved in ethanol (25 mL) and sodium tetrahydroborate (289 mg, 7.64 mmol) is added. After stirring at room temperature for 2 hours, the solvent is evaporated under vacuum and the residue is partitioned between water (30 mL) and ethyl acetate (30 mL). The organic layer is separated, dried over sodium sulfate and filtered. The filtrates are evaporated under reduced pressure. The residue is purified by silica gel flash chromatography, eluting with ethyl acetate/hexane (1:1) to ethyl acetate to give the title compound (1.50 g, 70.0%) as a white foam. ES/MS (m/z): 287 (M−99). $^1$H NMR (300.13 MHz, CDCl$_3$) δ 7.99-7.89 (m, 1H), 7.81-7.74 (m, 1H), 7.49-7.46 (m, 1H), 7.26 (s, 2H), 6.98 (dd, J=9.0, 12.0 Hz, 1H), 5.79-5.74 (m, 1H), 4.39-4.34 (m, 1H), 4.32-4.27 (m, 2H), 2.14 (s, 4H), 1.71 (s, 3H).

Method C Preparation 7

D-(+)-Proline (36 g, 313.1 mmol) is added in a single portion to a solution of tert-butyl N-[(3S,4S)-3-(5-acetamido-2-fluoro-phenyl)-4-formyl-tetrahydrofuran-3-yl]carbamate (95.6 g, 260.9 mmol) in methanol (956 mL) and the reaction mixture is stirred at room temperature for 16 hours. To the reaction mixture is added 1-(chloromethyl)-4-fluoro-1,4-diazoniabicyclo[2.2.2]octane bis(tetrafluoroborate) (120.1 g, 339.2 mmol) in a single portion and the mixture is stirred at room temperature for 24 hours. The solvent is concentrated under vacuum and the residue is partitioned between sodium bicarbonate (7% aqueous solution) (800 mL) and ethyl acetate (600 mL). The aqueous layer is extracted with ethyl acetate (2×300 mL). The organic layers are combined, dried over sodium sulfate, filtered, and concentrated under reduced pressure. The residue is dissolved in ethanol (956 mL) and sodium tetrahydroborate (13.80 g, 365.2 mmol) is added. After stirring at room temperature for 2 hours, the solvent is evaporated under vacuum and the residue is partitioned between water (500 mL) and ethyl acetate (500 mL). The organic layer is separated, dried over sodium sulfate, filtered and concentrated to dryness. The residue is purified by silica gel flash chromatography, eluting with ethyl acetate/hexane (1:1) to ethyl acetate to give the title compound (55 g, 54%) as a white foam. ES/MS (m/z): 287 (M–99). $^1$H NMR (300.13 MHz, CDCl$_3$) δ 7.99-7.89 (m, 1H), 7.81-7.74 (m, 1H), 7.49-7.46 (m, 1H), 7.26 (s, 2H), 6.98 (dd, J=9.0, 12.0 Hz, 1H), 5.79-5.74 (m, 1H), 4.39-4.34 (m, 1H), 4.32-4.27 (m, 2H), 2.14 (s, 4H), 1.71 (s, 3H).

PREPARATION 8

N-[[(3S,4S)-3-(5-Acetamido-2-fluoro-phenyl)-4-fluoro-4-(hydroxymethyl)tetrahydrofuran-3-yl]carbamothioyl]benzamide

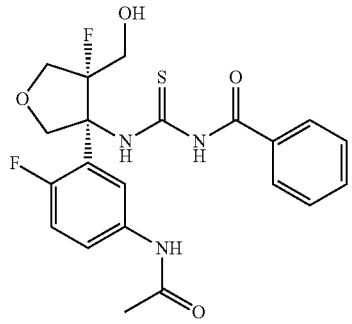 [SMILES: CC(=O)Nc1ccc(F)c([C@]2(NC(=S)NC(=O)c3ccccc3)COC[C@@]2(F)CO)c1]

Scheme 2, step I, (deprotection and thiourea formation): A solution of tert-butyl N-[(3S,4S)-3-(5-acetamido-2-fluoro-phenyl)-4-fluoro-4-(hydroxymethyl)tetrahydrofuran-3-yl]carbamate (2.70 g, 6.99 mmol) in dichloromethane (40 mL) and trifluoroacetic acid (8.00 mL, 106 mmol) is stirred at ambient temperature for 150 minutes. The reaction is concentrated under reduced pressure and azeotroped with toluene. The residue is dissolved in tetrahydrofuran and treated with triethylamine (1.10 mL, 7.89 mmol) and benzoyl isothiocyanate (1.00 mL, 7.41 mmol). The reaction is stirred at ambient temperature for 16.5 hours and is then quenched with a solution of saturated sodium bicarbonate in water, extracted with ethyl acetate and dichloromethane consecutively. The organic layers are combined, dried over magnesium sulfate, filtered, and concentrated under reduced pressure to give a residue. The residue is purified by silica gel flash chromatography, eluting with methanol/dichloromethane (0:10) to methanol/dichloromethane (1:10) to give the title compound (2.60 g, 83%). ES/MS (m/e): 450 (M+1).

PREPARATION 9

N-[3-[(3S,4S)-3-Amino-4-fluoro-4-(hydroxymethyl)tetrahydrofuran-3-yl]-4-fluoro-phenyl]acetamide hydrochloride Method A

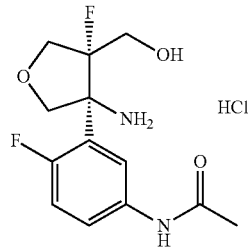 [SMILES: CC(=O)Nc1ccc(F)c([C@]2(N)COC[C@@]2(F)CO)c1 ; Cl]

Scheme 3, step L and step N, substep 1 (deprotection): Ethanol (8.61 mL, 148 mmol) is added drop wise to a solution of acetyl chloride (9.36 mL, 131 mmol) in ethyl acetate (127 mL) at 0° C. After stirring at 0° C. for 30 min, tert-butyl N-[(3S,4S)-3-(5-acetamido-2-fluoro-phenyl)-4-fluoro-4-(hydroxymethyl)tetrahydrofuran-3-yl]carbamate (12.7 g, 32.8 mmol) is added and then the reaction mixture is gradually warmed to room temperature and stirred for another 18 hours. A white solid is collected by filtration and dried under reduced pressure to constant weight to give the titled compound (11.0 g; 99.0%). ES/MS (m/z): 287 (M–35). $^1$H NMR (300.16 MHz, d$_6$-DMSO) δ 10.31 (s, 1H), 9.05 (s, 2H), 7.85-7.83 (m, 1H), 7.75-7.71 (m, 1H), 7.31-7.22 (m, 1H), 5.15-5.07 (m, 3H), 4.48-4.33 (m, 3H), 4.12-3.97 (m, 3H), 2.50 (s, 4H), 2.05 (s, 4H), 1.98 (s, 1H), 1.59 (s, 1H).

Method B Preparation 9

Hydrochloric acid (4 M in 1,4-dioxane, 1.95 mL, 7.80 mmol) is added to a solution of tert-butyl N-[(3S,4S)-3-(5-acetamido-2-fluoro-phenyl)-4-fluoro-4-(hydroxymethyl)tetrahydrofuran-3-yl]carbamate (1.00 g, 2.59 mmol) in ethyl acetate (10 mL) and the mixture is stirred overnight at room temperature. The mixture is filtered and the white precipitate is washed with ethyl acetate (10 ml) to obtain the title compound (800 mg, 96.0%) as a white solid. ES/MS (m/z): 287 (M+1).

Method C Preparation 9

Hydrogen chloride in isopropyl alcohol 6 M (100 ml, 600 mmol) is added drop wise to a solution of tert-butyl N-[(3S,4S)-3-(5-acetamido-2-fluoro-phenyl)-4-fluoro-4-(hydroxymethyl)tetrahydrofuran-3-yl]carbamate (56 g, 144.9 mmol) in isopropyl alcohol (225 mL). After stirring at 22° C. for 16 hours, the reaction is diluted with hexanes (350 mL) and stirred an additional 30 minutes. A white solid is collected by filtration and dried under reduced pressure to constant weight to give the title compound (36.5 g, 78%). ES/MS (m/z): 287 (M–35). $^1$H NMR (300.16 MHz, d$_6$-DMSO) δ 10.31 (s, 1H), 9.05 (s, 2H), 7.85-7.83 (m, 1H), 7.75-7.71 (m, 1H), 7.31-7.22 (m, 1H), 5.15-5.07 (m, 3H), 4.48-4.33 (m, 3H), 4.12-3.97 (m, 3H), 2.50 (s, 4H), 2.05 (s, 4H), 1.98 (s, 1H), 1.59 (s, 1H).

PREPARATION 10

N-[(4aR,7aS)-7a-(5-Acetamido-2-fluoro-phenyl)-4a-fluoro-5,7-dihydro-4H-furo[3,4-d][1,3]thiazin-2-yl]benzamide Method A

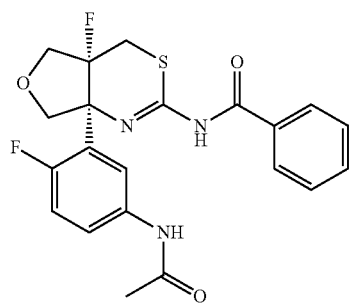 [SMILES: CC(=O)Nc1ccc(F)c([C@]23COC[C@@]2(F)CSC(NC(=O)c2ccccc2)=N3)c1]

Scheme 2, step J (cyclization): A solution of N-[[(3S,4S)-3-(5-acetamido-2-fluoro-phenyl)-4-fluoro-4-(hydroxymethyl)tetrahydrofuran-3-yl]carbamothioyl]benzamide (2.60 g, 5.78 mmol) and 1-chloro-N,N,2-trimethylpropenylamine (1.10 mL, 8.31 mmol) in dichloromethane (50 mL) is stirred at ambient temperature for 190 minutes. The reaction is quenched with a solution of saturated sodium bicarbonate in water, and extracted with dichloromethane. The organic layers are combined, dried over magnesium sulfate, filtered, and concentrated under reduced pressure to give a residue. The residue is purified by silica gel flash chromatography, eluting with ethyl acetate/hexane (0:1) to ethyl acetate/hexane (1:0) to give the title compound (1.36 g, 54%). ES/MS (m/e): 432.0 (M+1).

Method B Preparation 10

A solution of N-[3-[(3S,4S)-3-amino-4-fluoro-4-(hydroxymethyl)tetrahydrofuran-3-yl]-4-fluoro-phenyl]acetamide hydrochloride (14.5 g, 40.44 mmol) in THF (290 mL) is treated with triethylamine (5.64 mL, 40.44 mmol) and the mixture is stirred for 15 minutes and then cooled to 5° C. Benzoyl isothiocyanate (6 mL, 44.48 mmol) is added and the reaction is warmed to room temperature over 3 hours. 1,1'-Carbonyldiimidazole (7.21 g, 44.48 mmol) is added and the reaction mixture is stirred at room temperature for 16 hours, and then refluxed for 72 hours. The reaction mixture is cooled to 22° C. and then poured into water (150 mL) and MTBE (200 mL). The organic layer is separated and the aqueous layer is washed with MTBE (2×100 mL). The organic layers are combined, dried over sodium sulfate, filtered and evaporated to a residue. The residue is purified by silica gel chromatography eluting with methylene chloride/ethyl acetate (1/1) to give the title compound as white foamy solid (10.5 g, 60%). ES/MS (m/e): 328.0 (M+1).

PREPARATION 11

N-[(4aR,7aS)-7a-(5-Acetamido-2-fluoro-phenyl)-4a-fluoro-5,7-dihydro-4H-furo[3,4-d][1,3]oxazin-2-yl]benzamide Method A

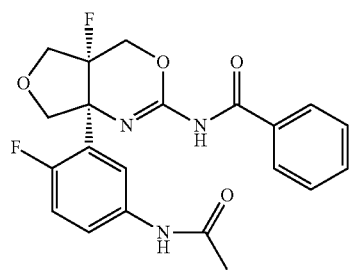 [SMILES: CC(=O)Nc1ccc(F)c([C@]23COC[C@@]2(F)COC(NC(=O)c2ccccc2)=N3)c1]

Scheme 3, step L, substep 2a and b (neutralization, thiourea formation and cyclization): Triethylamine (1.90 mL, 13.6 mmol) is added to a solution of N-[3-[(3S,4S)-3-amino-4-fluoro-4-(hydroxymethyl)tetrahydrofuran-3-yl]-4-fluoro-phenyl]acetamide hydrochloride (4.00 g, 12.4 mmol) in acetonitrile (40 mL) at 5° C. under nitrogen. After stirring for 30 min benzoyl isothiocyanate (1.76 mL, 13.0 mmol) is added drop wise. The resulting mixture is stirred at 5° C. for 1 hour. Trimethylsilyl chloride (1.73 mL, 13.6 mmol) and DMSO (968 µL, 13.6 mmol) are added and the mixture is stirred at 5° C. for 2 hours. The reaction mixture is poured into an aqueous solution of potassium phosphate dibasic (20%, 150 mL) to reach pH 7-8 and stirred for 30 min Ethyl acetate (50 mL) is added and the mixture is filtered through diatomaceous earth. The organic layer is separated, and the aqueous layer is extracted with ethyl acetate (50 mL). The organic layers are combined, washed with brine, dried over magnesium sulfate, and filtered. The filtrates are evaporated under reduced pressure and the residue is purified by silica gel flash chromatography eluting with ethyl acetate/hexane (60%) to ethyl acetate/hexane (90%) to give the title compound (3.50 g, 68.0%) as white solid. ES/MS (m/z): 416 (M+1).

Method B Preparation 11

Scheme 3, step L, substeps 2a and b (neutralization, N-carbamoyl benzamide formation, and cyclization): A mixture of N-[3-[(3S,4S)-3-amino-4-fluoro-4-(hydroxymethyl)tetrahydrofuran-3-yl]-4-fluoro-phenyl]acetamide hydrochloride (12 g, 37.19 mmol), triethylamine (5.7 mL, 41 mmol), and phenyl N-benzoylcarbamate (9.9 g, 41 mmol) are dissolved in THF (240 mL) and the mixture is heated at 70° C. for 2 hours. The mixture is cooled to room temperature and extracted with ethyl acetate (500 mL), washed with water (250 mL), brine (250 mL), dried over Na₂SO₄, filtered, and concentrated to dryness to give the intermediate thiourea. (LCMS (m/z): 434 (M+H). The crude material is dissolved in dichloromethane (240 mL) and cooled to −78° C. Diethylaminosulfur trifluoride (5.9 mL, 45 mmol) is added, the dry ice cooling bath is removed and the mixture is allowed to warm to room temperature and stirred 1 hour. The mixture is diluted with dichloromethane (500 mL) and washed with saturated aqueous sodium bicarbonate (250 mL). The mixture is filtered through diatomaceous earth and washed with brine (250 mL). The organic layer is dried over sodium sulfate, filtered, and concentrated to dryness. The residue is purified with silica gel chromatography eluting with a gradient of dichloromethane and methanol (99:1) to (95:5). The purification is repeated on mixed fractions to give the title compound (13.5 g, 87%). LCMS (m/z): 415.8 (M+H).

PREPARATION 12

(4aR,7aS)-7a-(5-Amino-2-fluoro-phenyl)-4a-fluoro-5,7-dihydro-4H-furo[3,4-d][1,3]thiazin-2-amine

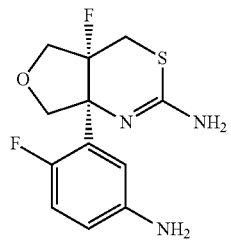 [SMILES: NC1=N[C@@]2(c3cc(N)ccc3F)COC[C@@]2(F)CS1]

Method A

Scheme 2, step K, substep 1 (deprotection): A solution of N-[(4aR,7aS)-7a-(5-acetamido-2-fluoro-phenyl)-4a-fluoro-5,7-dihydro-4H-furo[3,4-d][1,3]thiazin-2-yl]benzamide (2.36 g, 3.15 mmol), O-methylhydroxylamine hydrochloride (1.50 g, 17.6 mmol) and pyridine (1.50 mL, 18.6 mmol) in ethanol (30 mL) is heated to 50° C. for 16 hours. Then concentrated hydrochloric acid (6.00 mL, 79.2 mmol) is added, and the heating is continued for an additional 24 hours. The reaction is cooled to ambient temperature and concentrated under reduced pressure. The residue is purified by silica gel flash chromatography, eluting with 7 M ammonia in methanol/dichloromethane (0/10) to 7 M ammonia in methanol/dichloromethane (1/10) to give the title compound (800 mg, 89%). ES/MS (m/e): 286.0 (M+1).

Method B

Scheme 2, step K, substep 1 (deprotection): A solution of N-[(4aR,7aS)-7a-(5-acetamido-2-fluoro-phenyl)-4a-fluoro-5,7-dihydro-4H-furo[3,4-d][1,3]thiazin-2-yl]benzamide (1.20 g, 2.50 mmol), O-methylhydroxylamine hydrochloride (1.50 g, 23.5 mmol) and pyridine (2.00 mL, 24.7 mmol) in ethanol (25 mL) is heated to 50° C. for 18 hours. The reaction is then purified directly by a SCX column using methanol followed by 7 M ammonia in methanol as the eluent to give a residue. The residue is dissolved in ethanol (15 mL) and hydrochloric acid (3.00 mL, 39.6 mmol), and heated at 50° C. for 23 hours. The reaction is cooled to ambient temperature and concentrated under reduced pressure. The residue is purified by an SCX column in methanol followed by 7 M ammonia in methanol to give the title compound (640 mg, 90%). ES/MS (m/e): 286.0 (M+1).

Method C Preparation 12

A solution of N-[(4aR,7aS)-7a-(5-acetamido-2-fluoro-phenyl)-4a-fluoro-5,7-dihydro-4H-furo[3,4-d][1,3]thiazin-2-yl]benzamide (2.15 g, 2.49 mmol), lithium hydroxide (179 mg, 7.47 mmol) in methanol (25 mL) is heated to 50° C. for 16 hours. Then reaction mixture is cooled to room temperature and the solvent is evaporated. The residue is diluted with ethyl acetate (15 mL) and water (20 mL) and 2 M citric acid aqueous solution is added to adjust the pH to 1. The aqueous layer is separated and neutralized with NaOH 50% w/w aqueous solution until the pH=10. The reaction mixture is washed with ethyl acetate (2×15 mL) and the organic layers are combined, dried over sodium sulfate, and filtered. The filtrate is evaporated to give the title compound (850 mg, 89%). The crude material is used without further purification. ES/MS (m/e): 286.0 (M+1).

PREPARATION 13

N-[3-[(4aR,7aS)-2-Amino-4a-fluoro-5,7-dihydro-4H-furo[3,4-d][1,3]oxazin-7a-yl]-4-fluoro-phenyl]acetamide Method A

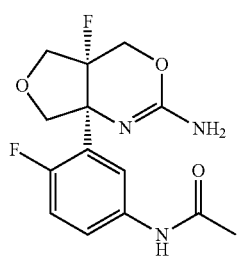 [SMILES: CC(=O)Nc1ccc(F)c([C@]23COC[C@@]2(F)COC(N)=N3)c1]

Scheme 3, step M, substep 1 (deprotection): N-[(4aR,7aS)-7a-(5-acetamido-2-fluoro-phenyl)-4a-fluoro-5,7-dihydro-4H-furo[3,4-d][1,3]oxazin-2-yl]benzamide (3.50 g, 8.43 mmol) is added to a solution of lithium hydroxide (225 mg, 9.27 mmol) in methanol (35 mL) and the mixture is stirred at 40° C. for 18 hours. The solvent is evaporated and the residue is partitioned between ethyl acetate (50 mL) and water (30 mL). The aqueous layer is extracted with ethyl acetate and the organic layers are combined. The organic solution is washed with aqueous hydrochloric acid (0.1 M, 50 mL). The aqueous layer is then treated with aqueous sodium hydroxide solution (2.0 M) until pH=10 and is extracted twice with ethyl acetate (2×50 mL). The organic layers are combined, dried over magnesium sulfate, and filtered. The filtrates are evaporated under reduced pressure to yield the title compound (1.9 g, 72%) as a white foam. ES/MS (m/z): 312 (M+1).

Method B Preparation 13

Scheme 3, step N, substeps 2a and 2b (neutralization and cyclization): A solution of N-[3-[3S,4S)-3-amino-4-fluoro-4-(hydroxymethyl)tetrahydrofuran-3-yl]-4-fluoro-phenyl]acetamide hydrochloride (8 g, 24.8 mmol) in THF (80 mL) is treated with [benzoyl(phenoxycarbonyl)amino]potassium (7.62, 27.3 mmol) and the mixture is heated at reflux for 3 hours. The reaction is cooled and the solvent is evaporated. The residue is partitioned in water (50 mL) and ethyl acetate (100 mL) and the aqueous layer is discarded. The organic layer is washed with brine, dried over magnesium sulfate, and filtered. The filtrate is evaporated and the residue is dried under vacuum to a constant weight. The crude material is dissolved in methylene chloride (120 mL) and then cooled to –35° C. under a nitrogen atmosphere. Diethylaminosulfur trifluoride (3.94 mL, 29.75 mmol) is added keeping the internal temperature at –35° C. The mixture is stirred 1 hour at this temperature and then warmed to 22° C. for 2 hours. The reaction is poured into potassium dibasic phosphate aqueous solution (200 mL) and methylene chloride (50 mL). The organic layer is separated, washed with brine, dried over magnesium sulfate, and filtered. The filtrate is evaporated and dried under vacuum to a constant weight. This crude material is dissolved in methanol (80 mL) and lithium hydroxide (783 mg, 32.2 mmol) is added. The mixture is heated at 50° C. during for 16 hours. The methanol is evaporated and the residue is poured into water (50 mL) and ethyl acetate (100 mL). The organic layer is separated and the aqueous layer washed with additional ethyl acetate (100 mL). The organic layers are combined and washed with hydrochloric acid 0.5 M (2×30 mL). The aqueous layers are combined and sodium hydroxide is added to adjust the pH=10, and the aqueous mixture is extracted with ethyl acetate (2×50 mL). The organic layers are combined, dried over magnesium sulfate, and filtered. The filtrate is evaporated to dryness and the residue is dried under vacuum to a constant weight to give the title compound (5.5 g; 71% overall yield three steps). ES/MS (m/z): 312 (M+1).

PREPARATION 14

(4aR,7aS)-7a-(5-Amino-2-fluoro-phenyl)-4a-fluoro-5,7-dihydro-4H-furo[3,4-d][1,3]oxazin-2-amine Method A

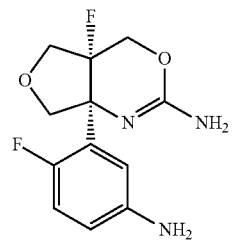

Scheme 3, step M, substep 1 (deprotection): N-[3-[(4aR,7aS)-2-amino-4a-fluoro-5,7-dihydro-4H-furo[3,4-d][1,3]oxazin-7a-yl]-4-fluoro-phenyl]acetamide (800 mg, 2.57 mmol) is added to aqueous hydrogen chloride (1.0 M, 10 ml) and the resulting solution is heated at 90° C. for 3 hours. The reaction is cooled to 22° C. and washed with ethyl acetate (5 mL). The aqueous layer is separated and treated with aqueous sodium hydroxide solution (1.0 M) until pH=10 and is extracted with ethyl acetate (2×5 mL). The organic layers are combined, dried over magnesium sulfate, and filtered. The filtrates are evaporated under reduced pressure to yield the title compound (650 mg, 2.34 mmol). ES/MS (m/z): 270 (M+1).

Method B Preparation 14

Scheme 3, step N, substeps 2a and b (neutralization and cyclization): Triethylamine (0.32 mL, 2.3 mmol) is added to a solution of N-[3-[(3S,4S)-3-amino-4-fluoro-4-(hydroxymethyl)tetrahydrofuran-3-yl]-4-fluoro-phenyl]acetamide hydrochloride (600 mg, 1.85 mmol) in dichloromethane (10 mL). The mixture is stirred at room temperature for 10 minutes and concentrated. Ethyl acetate (10 mL) is added to the residue, and the mixture is heated to 40° C. for 10 minutes. The mixture is filtered and the filtrate is concentrated and added to a 40 mL screw cap vessel. Absolute ethanol (12 mL) and cyanogen bromide (305 mg, 2.79 mmol) are added, and the mixture is heated to 120° C. for 4 hours. The solvent is evaporated to dryness. Water (20 mL) and aqueous hydrochloric acid (1.0 M, 20 mL) are added. The resulting mixture is washed with ethyl acetate (40 mL). The aqueous layer is treated with concentrated aqueous hydrochloric acid (3.2 mL) and stirred at 50° C. for 48 hours. The mixture is cooled to room temperature and the pH is adjusted to basic using aqueous sodium hydroxide solution (2.0 M). The mixture is then extracted with ethyl acetate (200 mL). The organic layer is washed with brine (100 mL) and dried over sodium sulfate, filtered, and concentrated. The residue is purified by silica gel flash chromatography eluting with a gradient of 7 M ammonia in methanol/dichloromethane (98:2) to 7 M ammonia in methanol/dichloromethane (90:10) to give the title compound (175 mg, 35%) as a white solid. ES/MS (m/z): 270 (M+1).

Method C Preparation 14

N-[3-[4aR,7aS)-2-Amino-4a-fluoro-5,7-dihydro-4H-furo[3,4-d][1,3]oxazin-7a-yl]-4-fluoro-phenyl]acetamide (17 g, 54.6 mmol) is added to aqueous hydrogen chloride (1.0 M, 218 ml) and the resulting solution is heated at 90° C. for 3 hours. The reaction is cooled to 5° C. and sodium hydroxide 50% w/w aqueous solution is added to adjust pH=10. The mixture is washed with ethyl acetate (3×100 mL). The organic layers are separated, dried over magnesium sulfate, and filtered. The filtrates are evaporated under reduced pressure to give the title compound as a white solid (13.4 g, 91%). ES/MS (m/z): 270 (M+1).

PREPARATION 15

N-[3[(4aR,7aS)-2-Amino-4a-fluoro-5,7-dihydro-4H-furo[3,4-d][1,3]oxazin-7a-yl]-4-fluoro-phenyl]-5-cyano-pyridine-2-carboxamide Method A

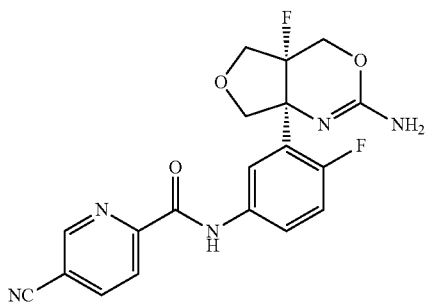 [SMILES: N#Cc1ccc(C(=O)Nc2ccc(F)c([C@]34COC[C@@]3(F)COC(N)=N4)c2)nc1]

Scheme 3, steps M, substep 2 or step N, substep 3 (amidation): Dimethylformamide (20 μL, 0.26 mmol) and oxalyl chloride (162 μL, 1.87 mmol) is added to a slurry of 5-cyanopyridine-2-carboxylic acid (310 mg, 2.00 mmol) in acetonitrile (10 mL) and stirred at room temperature for about 10 minutes. This mixture is then added in a single portion to a 50° C. solution of (4aR,7aS)-7a-(5-amino-2-fluoro-phenyl)-4a-fluoro-5,7-dihydro-4H-furo[3,4-d][1,3]oxazin-2-amine (500 mg, 1.86 mmol) in ethanol (5 mL) and water (5 mL) and the temperature is maintained at 50° C. The reaction mixture is stirred for about 10 minutes and quenched with saturated aqueous sodium bicarbonate solution. The mixture is then extracted with ethyl acetate. The organic layer is dried over sodium sulfate, filtered, and concentrated to give a residue, which is purified by silica gel flash chromatography eluting with a gradient of 0 to 10% MeOH in dichloromethane and further purified twice using a gradient of 7 M ammonia in methanol/dichloromethane (5/95) to give the title compound (470 mg, 63%). ES/MS (m/z): 400 (M+1).

Method B Preparation 15

To a solution of (4aR,7aS)-7a-(5-amino-2-fluoro-phenyl)-4a-fluoro-5,7-dihydro-4H-furo[3,4-d][1,3]oxazin-2-amine (11.6 g, 41.8 mmol) in a mixture of water (81 mL) and ethanol (116 mL), is added hydrogen chloride 1 M in water (41.7 mL, 41.7 mmol). 1-(3-Dimethylaminopropyl)-3-ethylcarbodiimide hydrochloride (8.41 g, 43.8 mmol) and 5-cyanopyridine-2-carboxylic acid (6.5 g, 43.8 mmol) are added in one portion and the reaction is stirred at room temperature for 3 hours. Additional 1-(3-dimethylaminopropyl)-3-ethylcarbodiimide hydrochloride (10 mg, 52.16 μmol) is added and the mixture is stirred for 30 minutes. The reaction mixture is heated at 50° C. and all the solids are dissolved. Sodium hydroxide, 1 M in water (45.97 mL, 45.97 mmol) is added drop wise keeping the temperature at 50° C. and adjusting pH to 11. The reaction is cooled to room temperature and a white solid is collected by filtration and washed with water. The solid is dried under vacuum to a constant weight and then purified by silica gel chromatography eluting with a mixture of methylene chloride/methanol (95:5) to give the title compound (7.5 g, 45%) as white solid. ES/MS (m/z): 400 (M+1).

PREPARATION 16

N-[3-[(4aR,7aS)-2-Amino-4a-fluoro-5,7-dihydro-4H-furo[3,4-d][1,3]oxazin-7a-yl]-4-fluoro-phenyl]-5-chloro-pyrazine-2-carboxamide

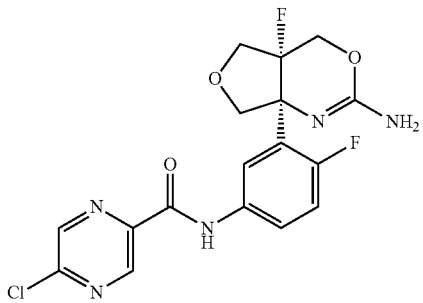 [SMILES: NC1=N[C@@]2(c3cc(NC(=O)c4cnc(Cl)cn4)ccc3F)COC[C@@]2(F)CO1]

Scheme 3, steps M, substep 2 or step N, substep 3 (amidation): A mixture of 5-chloropyrazine-2-carboxylic acid (1.53 g, 9.66 mmol) in acetonitrile (15 mL, 283 mmol) is treated with DMF (115 μL, 1.49 mmol) and oxalyl chloride (970 μL, 11.1 mmol). The mixture is stirred at ambient temperature under nitrogen for 20 minutes. In a separate flask is added (4aR,7aS)-7a-(5-amino-2-fluoro-phenyl)-4a-fluoro-5,7-dihydro-4H-furo[3,4-d][1,3]oxazin-2-amine (2.00 g, 7.43 mmol), ethanol (7.4 mL), water (7.4 mL) and the mixture is heated at 50° C. The acid chloride is added to the solution prepared above and the reaction mixture is stirred at 50° C. for 20 minutes. The reaction is cooled to room temperature, diluted with ethyl acetate (200 mL), and washed with water (40 mL) and saturated aqueous NaHCO₃ (40 mL). The aqueous washes are combined and extracted with ethyl acetate (100 mL). The combined organic layers are dried (Na₂SO₄) and the solvent removed in vacuo to give the crude product. The crude product is purified by silica gel flash chromatography, eluting with ethyl acetate to give the title product (2.85 g, 94%). ES/MS (m/e): 410 (M+1)

PREPARATION 17

5-(Cyclopropylmethoxy)pyrazine-2-carboxylic acid

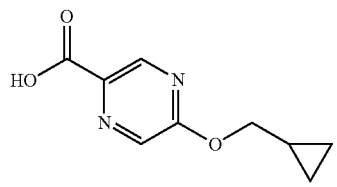 [SMILES: O=C(O)c1cnc(OCC2CC2)cn1]

A solution of 5-chloropyrazine-2-carboxylic acid (1.00 g, 6.31 mmol), cyclopropyl carbinol (1.00 mL, 12.4 mmol) and potassium tert-butoxide (2.00 g, 17.8 mmol) in dimethylformamide (20.0 mL) is heated at 100° C. for 3 hours. The reaction is cooled to room temperature, quenched with 1 M hydrochloric acid. The mixture is extracted with ethyl acetate and isopropyl alcohol/chloroform (1/10), dried over magnesium sulfate, filtered, and concentrated under reduced pressure to give the title compound (1.10 g, 90%) as a grayish solid. This acid is used directly without further purification.

PREPARATION 18

Methyl 5-(cyclopropoxy)pyrazine-2-carboxylate

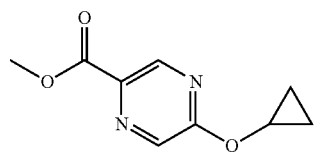

Cyclopropanol (542 μL, 8.69 mmol) is added to a suspension of methyl 5-chloropyrazine-2-carboxylate (1.0 g, 5.79 mmol) and potassium carbonate (1.60 g, 11.59 mmol) in dimethylformamide (11.6 mL). The reaction mixture is stirred for 15 hours at room temperature then for 24 hours at 50° C. The reaction is cooled to ambient temperature, diluted with water, and extracted with ethyl acetate (3 times). The organic layers are combined, dried over sodium sulfate, filtered, and concentrated under reduced pressure to give a brown oil. The crude product is purified by silica gel flash chromatography, eluting with ethyl acetate/hexane (0:100) to ethyl acetate/hexane (35:65) to give the title compound (610 mg, 54%). ES/MS (m/e): 195.0 (M+1).

PREPARATION 19

5-(Cyclopropoxy)pyrazine-2-carboxylic acid

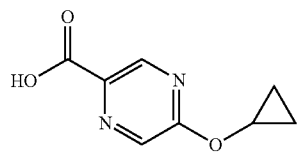 [SMILES: O=C(O)c1cnc(OC2CC2)cn1]

Lithium hydroxide (264 mg, 6.28 mmol) is added to a solution of methyl 5-(cyclopropoxy)pyrazine-2-carboxylate (610 mg, 3.14 mmol) in tetrahydrofuran (10 mL) and water (0.5 mL). The reaction mixture is stirred for 1 hour at 50° C., cooled to ambient temperature, diluted with water, brought to pH=2 by slow addition of 1 M HCl, and extracted with dichloromethane (4 times). The organic layers are combined, dried over sodium sulfate, filtered, and concentrated under reduced pressure to give the title compound (550 mg, 97%). ES/MS (m/e): 181.0 (M+1).

PREPARATION 20

5-(Oxetan-2-ylmethoxy)pyrazine-2-carboxylic acid

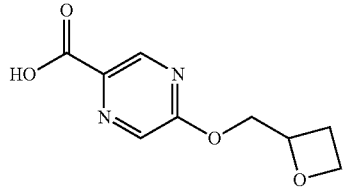 [SMILES: O=C(O)c1cnc(OCC2CCO2)cn1]

In a microwave vial 5-chloropyrazine-2-carboxylic acid (100.0 mg, 0.631 mmol), dimethylformamide (5 mL), oxetan-2-ylmethanol (83.4 mg, 0.946 mmol) and potassium tert-butoxide (176.9 mg, 1.58 mmol) are added. A small exotherm is observed. After 1 minute at room temperature the vial is sealed and the mixture heated at 120° C. for 30 minutes in the microwave. The reaction mixture is then quenched with aqueous NH₄Cl and the solvent evaporated under reduced pressure. The resultant residue is triturated in 2-propanol. The filtrate is concentrated under reduced pressure to give the title compound as a cream solid (0.294 g, 99%) and is used without further purification. ES/MS (m/e): 211.0 (M+1), 208.8 (M−H).

PREPARATION 21

5-(2,2-difluoroethoxy)pyrazine-2-carboxylic acid

Potassium tert-butoxide (4.25 g, 37.84 mmol) is added to a solution of 5-chloropyrazine-2-carboxylic acid (1.00 g, 6.31 mmol) and difluoroethanol (2.59 g, 31.54 mmol) in DMF (20 mL) and the mixture is heated at 100° C. for 2 hours. The reaction is cooled to room temperature and stirred overnight under nitrogen. The reaction is quenched with 1 M HCl (30 mL) and extracted with ethyl acetate (3 times). The combined organic layers are dried over sodium sulfate, filtered, and concentrated to give the crude product. The crude product is purified by silica gel flash chromatography, eluting with a gradient of 0.5% to 10% methanol in dichloromethane and azeotroped with xylenes to remove residual DMF to give the title product (1.18 g, 91%). ES/MS (m/e): 205.0 (M+1).

The following compounds in Table 1 are prepared in a manner essentially analogous to the method set forth in Preparation 21 using the appropriate alcohol.

TABLE 1

| Prep. No. | Chemical Name | Structure | ES/MS (m/z) (M + 1) |
|---|---|---|---|
| 22 | 5-(2-Methoxyethoxy)pyrazine-2-carboxylic acid | 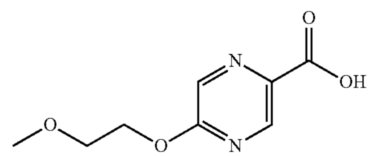 | 199.0 |
| 23 | 5-Ethoxypyrazine-2-carboxylic acid | 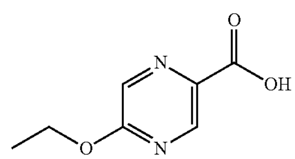 | 169.0 |
| 24 | 5-Propoxypyrazine-2-carboxylic acid | 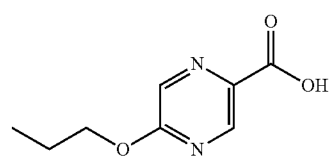 | 183.0 |
| 25 | 5-(2,2,3,3-Tetrafluoropropoxy)pyrazine-2-carboxylic acid | 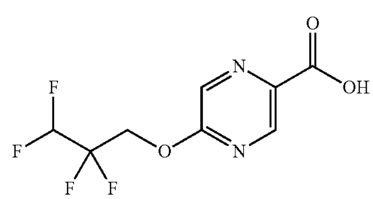 [SMILES: O=C(O)c1cnc(OCC(F)(F)C(F)F)cn1] | 255.0 |
| 26 | 5-(2,2-Difluoropropoxy)pyrazine-2-carboxylic acid | 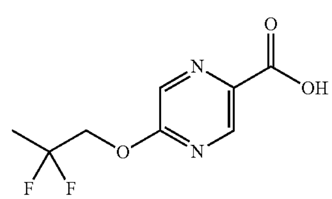 | 219.0 |
| 27 | 5-[(2,2-Difluorocyclopropyl)methoxy]pyrazine-2-carboxylic acid | 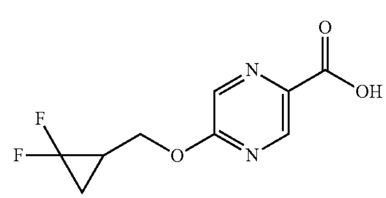 [SMILES: O=C(O)c1cnc(OCC2CC2(F)F)cn1] | 231.0 |

PREPARATION 28

Methyl 5-(2,2,3,3-tetrafluoropropoxy)pyridine-2-carboxylate

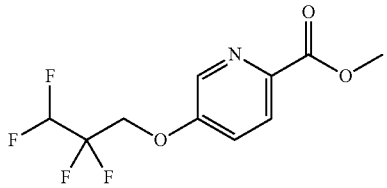 [SMILES: COC(=O)c1ccc(OCC(F)(F)C(F)F)cn1]

Methyl 5-hydroxypyridine-2-carboxylate (0.903 g, 5.90 mmol) is suspended in acetone (7 mL) and DMF (7 mL). 325 Mesh potassium carbonate (2.44 g, 17.69 mmol) is added in one portion and stirred at room temperature for 1.5 hours under nitrogen. 2,2,3,3-Tetrafluoropropyl trifluoromethanesulfonate (2.02 g, 7.67 mmol) is added drop wise and the mixture is stirred for 2 hours. The reaction mixture is diluted with ethyl acetate and saturated NH$_4$Cl and extracted with ethyl acetate (3 times). The combined organic extracts are washed with brine, dried over Na$_2$SO$_4$, filtered, and the solvent removed in vacuo. The crude product is purified by silica gel flash chromatography, eluting with a gradient of 0-20% ethyl acetate in dichloromethane to give the title compound (1.047 g, 66%). ES/MS (m/e): 268.0 (M+1).

PREPARATION 29

5-(2,2,3,3-Tetrafluoropropoxy)pyridine-2-carboxylic acid

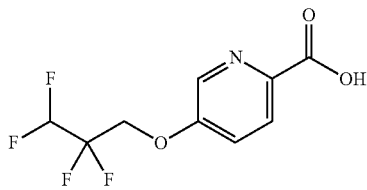 [SMILES: O=C(O)c1ccc(OCC(F)(F)C(F)F)cn1]

Lithium hydroxide (469 mg, 19.6 mmol) is added to a solution of methyl 5-(2,2,3,3-tetrafluoropropoxy)pyridine-2-carboxylate (1.047 mg, 3.92 mmol) in THF (7 mL) and water (7 mL). The reaction mixture is stirred for 1 hour at 60° C., cooled to ambient temperature, quenched with 1 M HCl (20 mL), diluted with brine and extracted with dichloromethane (3 times). The organic layers are combined, dried over MgSO$_4$, filtered, and concentrated under reduced pressure to give the title compound (921 mg, 93%). ES/MS (m/e): 254.0 (M+1).

PREPARATION 30

Ethyl 5-(2,2-difluoroethoxy)-3-fluoro-pyridine-2-carboxylate

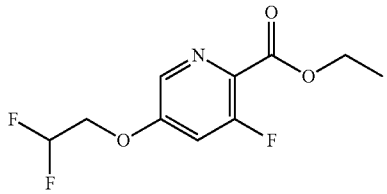 [SMILES: CCOC(=O)c1ncc(OCC(F)F)cc1F]

Ethyl 3,5-difluoropyridine-2-carboxylate (0.98 g, 5.24 mmol) is dissolved in acetonitrile (20 mL). Difluoroethanol (430 µL, 6.81 mmol) is added followed by potassium carbonate (1.83 g, 13.09 mmol). The solution is stirred at room temperature for 2 days then filtered and the filtrate is concentrated. The crude material is purified via silica gel chromatography eluting with a 0-25-50% ethyl acetate/hexanes gradient to give the title compound (242 mg, 18%). ES/MS (m/e): 250.0 (M+1).

PREPARATION 31

5-(2,2-Difluoroethoxy)-3-fluoro-pyridine-2-carboxylic acid

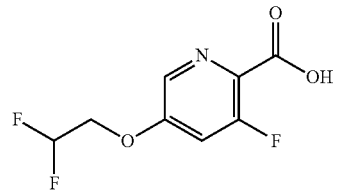

Sodium hydroxide (2 M in water, 2.43 mL, 4.86 mmol) is added to a solution of ethyl 5-(2,2-difluoroethoxy)-3-fluoro-pyridine-2-carboxylate (242 mg, 0.97 mmol) in THF (10 mL). The reaction is stirred at room temperature for 5 days. The reaction is quenched by the addition of 4 M HCl in dioxane (1.25 mL, 5 mmol) and the solution is concentrated to give the crude title compound (493 mg, 229%). ES/MS (m/e): 222.0 (M+1).

PREPARATION 32

2-Chloro-3-fluoro-5-(2,2,3,3-tetrafluoropropoxy)pyridine

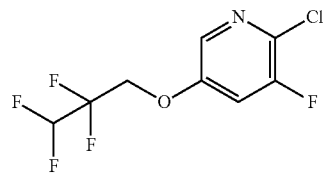 [SMILES: Fc1cc(OCC(F)(F)C(F)F)cnc1Cl]

6-Chloro-5-fluoro-pyridin-3-ol (300 mg, 2.03 mmol) is dissolved in DMF (10 mL). Potassium carbonate (562 mg, 4.07 mmol) is added followed by 2,2,3,3-tetrafluoropropyl trifluoromethanesulfonate (591 mg, 2.24 mmol) (For preparation of this reagent, see US2013/143900, Ex 1). The reaction is stirred at room temperature for 18 hours then allowed to stand at room temperature for 4 days. The reaction is diluted with aqueous NaHCO$_3$ and ethyl acetate. The layers are separated and the aqueous layer is extracted with ethyl acetate (2×). The combined organic layers are washed with brine and concentrated. The crude material is purified via silica gel chromatography using a 0-10% ethyl acetate/hexanes gradient to give the title compound (440 mg, 83%). ES/MS (m/e): 262.0 (M+1).

PREPARATION 33

Methyl 3-fluoro-5-(2,2,3,3-tetrafluoropropoxy)pyridine-2-carboxylate

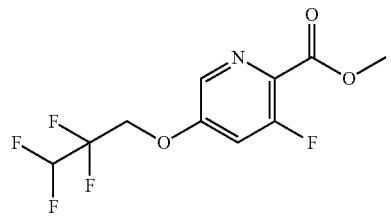 [SMILES: COC(=O)c1ncc(OCC(F)(F)C(F)F)cc1F]

2-Chloro-3-fluoro-5-(2,2,3,3-tetrafluoropropoxy)pyridine (440 mg, 1.68 mmol) is added to a Parr autoclave containing palladium (II) acetate (0.04 g, 0.18 mmol) and 1,1'-bis(diphenylphosphino)ferrocene (0.12 g, 0.21 mmol). Acetonitrile (9 mL) is added followed by methanol (6 mL). Triethylamine (0.6 mL, 4.3 mmol) is added and the autoclave is sealed, purged with $N_2$, purged with CO, and then pressurized with 100 psi CO and heated at 100° C. for 18 hours. The solution is concentrated to give the crude product that is purified via silica gel chromatography using a 0-25% ethyl acetate/hexanes gradient to give the title compound (430 mg, 90%). ES/MS (m/e): 286.0 (M+1).

PREPARATION 34

3-Fluoro-5-(2,2,3,3-tetrafluoropropoxy)pyridine-2-carboxylic acid

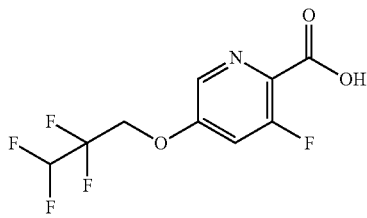 [SMILES: O=C(O)c1ncc(OCC(F)(F)C(F)F)cc1F]

Sodium hydroxide (2 M in water, 2 mL, 4.0 mmol) is added to a solution of methyl 3-fluoro-5-(2,2,3,3-tetrafluoropropoxy)pyridine-2-carboxylate (430 mg, 0.1.51 mmol) in THF (15 mL). The reaction is stirred at room temperature for 18 hours. The reaction is quenched by the addition of 4 M HCl in dioxane (1.25 mL, 5 mmol) and the solution concentrated to give the crude title compound (476 mg, 99%). ES/MS (m/e): 222.0 (M+1).

PREPARATION 35

(1-Fluorocyclopropyl)methanol

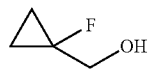

A 0° C. solution of 1-fluoro-cycloproanecarboxylic acid (0.78 g, 7.49 mmol) in THF (8 mL) is treated drop wise with 1 M borane-tetrahydrofuran complex (8.99 mL, 8.99 mmol) over 10 minutes. The reaction is warmed to room temperature and stirred under nitrogen for 18 minutes. Additional 1 M borane-tetrahydrofuran complex (3.75 mL, 3.75 mmol) is added and the reaction is stirred for 2 hours. The reaction is quenched with water (exotherm observed) followed by 1 N HCl (25 mL). The mixture is extracted with ethyl acetate and separated. The aqueous layer is extracted with ethyl acetate (2 times) and the organic layers combined. The combined organic layers are dried ($MgSO_4$), filtered and the solvent is removed in vacuo to give the title product (0.848 g, 100%).

PREPARATION 36

5-(2,2,2-Trifluoroethoxy)pyrazine-2-carboxylic acid

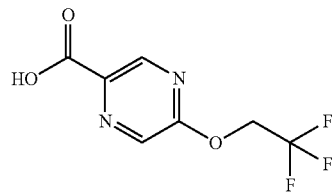 [SMILES: O=C(O)c1cnc(OCC(F)(F)F)cn1]

To a solution of methyl 5-chloropyrazine-2-carboxylate (25 g, 144.87 mmol) in DMF (250 mL) under nitrogen atmosphere is added cesium carbonate (47.2 g, 144.8 mmol) and 2,2,2-trifluoro-ethanol (15.7 mL, 217.3 mmol). The reaction mixture is stirred 72 hours at room temperature. The mixture is poured over water (1 L) and a pale brown solid is collected by filtration. The solid is washed with water and dried under vacuum to a constant weight. The dry crude material is recrystallized twice from a mixture of water (200 mL) and isopropyl alcohol (40 ml) to yield the intermediate methyl 5-(2,2,2-trifluoroethoxy)pyridine-2-carboxylate (15 g, 93%) as a pale cream solid and is used without further purification. A solution of intermediate methyl 5-(2,2,2-trifluoroethoxy)pyridine-2-carboxylate (5 g, 21.17 mmol) in methanol (50 mL) and 1 M sodium hydroxide aqueous solution (42.3 mL, 42.3 mmol) is stirred at room temperature for 2 hours. Hydrochloric acid 35% w/w is added to adjust the ph to 2. Methanol is evaporated and a pale cream solid is isolated by filtration. The solid is washed with water and dried under vacuum to give the title compound (3 g, 51%). ES/MS (m/z): 223.1 (M+1).

PREPARATION 37

5-(2,2,2-trifluoroethoxy)pyridine-2-carboxylic acid

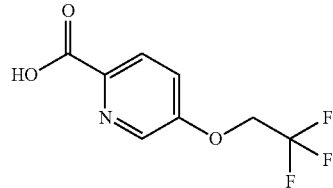 [SMILES: O=C(O)c1ccc(OCC(F)(F)F)cn1]

To a solution of methyl 5-hydroxypyridine-2-carboxylate (10.1 g, 65.95 mmol) and cesium carbonate (42.9 g, 131.9 mmol) in DMF (1 L) is added a solution of 2,2,2-trifluoroethyl trifluoromethanesulfonate (22.96 g, 98.93 mmol) in 20 ml of DMF over 2 hours. The reaction is stirred 4 hours at room temperature and then poured over water (1 L) and stirred for additional 1 hour. A brown solid is collected by filtration and washed with additional water. The solid is dried to a constant weight to give the intermediate compound (10.3 g 66%) of methyl 5-(2,2,2-trifluoroethoxy)pyridine-2-carboxylate which is used without further purification. To a solution of methyl 5-(2,2,2-trifluoroethoxy)pyridine-2-carboxylate (4.5 g, 19.1 mmol) in methanol (45 mL) is added sodium hydroxide 1 M solution (38.2 ml, 38.2 mmol) and the reaction is stirred for 2 hours at room temperature. The pH of the reaction mixture is adjusted with HCl 35% w/w to adjust pH=1 and then the resulting solid is isolated by filtration. The solid is washed with water and then dried under vacuum to give the title compound (3 g, 70%). ES/MS (m/z): 222.1 (M+1).

PREPARATION 38

[Benzoyl(phenoxycarbonyl)amino]potassium

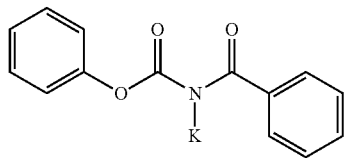

Potassium tert-butoxide 1.5 M solution (113.8 mL, 182 mmol) is added to a solution of benzamide (20.36 g, 168 mmol) di-phenyl carbonate (30 g, 140 mmol) in tetrahydrofuran (450 mL) under a nitrogen atmosphere. The reaction is stirred 16 hours at 20° C. A pale pink solid is collected by filtration and dried under reduced pressure to a constant weight to give the title compound (29 g; 74%). $^1$H NMR (300.16 MHz, d$_6$-DMSO) δ 7.88-7.85 (m, 2H), 7.55-7.40 (m, 3H), 7.15-7.10 (m, 2H), 6.77-6.67 (m, 3H).

Example 1

N-[3-[(4aR,7aS)-2-Amino-4a-fluoro-5,7-dihydro-4H-furo[3,4-d][1,3]thiazin-7a-yl]-4-fluoro-phenyl]-5-fluoro-pyridine-2-carboxamide hydrochloride

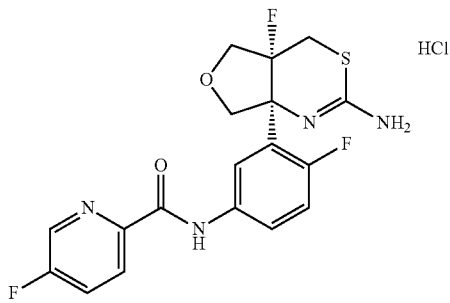 [SMILES: NC1=N[C@@]2(c3cc(NC(=O)c4ccc(F)cn4)ccc3F)COC[C@@]2(F)CS1 ; Cl]

Scheme 2, step K, substep 2 (amidation): Oxalyl chloride (180 μL, 2.07 mmol) is added to a solution of dimethylformamide (180 μL, 2.33 mmol) in acetonitrile (10 mL), and the resulting reaction is stirred for 10 min 5-Fluoropyridine-2-carboxylic acid (300 mg, 2.13 mmol) is added to the resulting solution. The resulting reaction is stirred for an additional 40 minutes, and then 5.0 mL of this solution is removed via syringe and added drop wise to a solution of (4aR,7aS)-7a-(5-amino-2-fluoro-phenyl)-4a-fluoro-5,7-dihydro-4H-furo[3,4-d][1,3]thiazin-2-amine (330 mg, 1.04 mmol) in ethanol (6.0 mL) and water (6.0 mL) at 50° C. The resulting solution is heated at 50° C. for 50 minutes before being purified by SCX columns (methanol, then 7 M ammonia in methanol) to give a residue, which is purified again by silica gel flash chromatography, eluting with 7 M ammonia in methanol/dichloromethane (0/10) to 7 M ammonia in methanol/dichloromethane (1/10) to give a residue, which is further purified by HPLC using a high resolution C18 column (Waters X-Bridge OBD 30×75 mm, 5 μm particle size) eluting with a 15-40% gradient of acetonitrile in (10 mM ammonium bicarbonate aqueous solution with 5% methanol). The eluent containing product is concentrated under reduced pressure to ~100 mL and is then lyophilized to give a white residue as the free base of the desired product. This material is dissolved in 2 mL of dichloromethane/methanol (1/1) and is treated with 1 M HCl in ether (360 μL, 0.36 mmol). The sample is concentrated to give the title compound (177 mg, 38%). ES/MS (m/e): 409.0 (M+1).

Example 2

N-[3-[(4aR,7aS)-2-Amino-4a-fluoro-5,7-dihydro-4H-furo[3,4-d][1,3]thiazin-7a-yl]-4-fluoro-phenyl]-5-methoxy-pyrazine-2-carboxamide hydrochloride

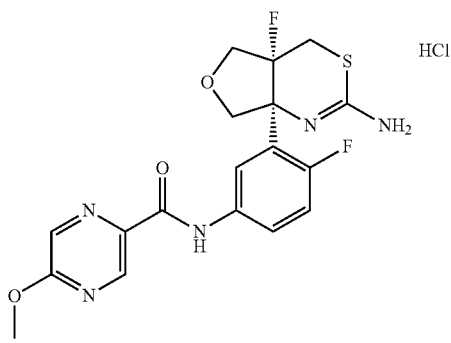 [SMILES: COc1cnc(C(=O)Nc2ccc(F)c([C@]34COC[C@@]3(F)CSC(N)=N4)c2)cn1 ; Cl]

Scheme 2, step K (amide formation): Oxalyl chloride (127 μL, 1.46 mmol) is added to a slurry of 5-methoxypyrazine-2-carboxylic acid (225 mg, 1.46 mmol) and dimethylformamide (113 μL, 1.46 mmol) in acetonitrile (6 mL). The resulting reaction is stirred for 90 min. This solution is added drop wise to a solution of (4aR,7aS)-7a-(5-amino-2-fluoro-phenyl)-4a-fluoro-5,7-dihydro-4H-furo[3,4-d][1,3]thiazin-2-amine (320 mg, 1.12 mmol) in ethanol (5.5 mL) and water (5.5 mL) at 50° C. The resulting solution is heated at 50° C. for 5 hours. The reaction is poured into a separatory funnel containing 200 mL NaHCO$_3$ (aq). The sample is extracted with dichloromethane (3×200 mL). The organic layers are combined, washed with brine, and concentrated. The crude product is purified by silica gel flash chromatography, eluting with 7 M ammonia in methanol/dichloromethane (0/10) to 7 M ammonia in methanol/dichloromethane (1/10). This material is further purified by reverse phase flash chromatography using a 150 g high resolution C18 column and eluting with a 5-60% gradient of ACN in (10 mM ammonium bicarbonate aqueous solution with 5% MeOH). The eluent containing product is isolated and extracted with a 4:1 chloroform:isopropanol solution (3×50 mL). The organic layers are combined, washed with brine, dried over MgSO$_4$, filtered, and concentrated to give the free base of the desired compound. This material is dissolved in dichloromethane (15 mL) and is treated with 4 M HCl in dioxane (900 μL, 3.6 mmol). The sample is concentrated to give the title compound (160 mg, 31.2%). ES/MS (m/e): 422.0 (M+1).

Example 3

N-[3-[(4aR,7aS)-2-Amino-4a-fluoro-5,7-dihydro-4H-furo[3,4-d][1,3]thiazin-7a-yl]-4-fluoro-phenyl]-5-cyano-pyridine-2-carboxamide hydrochloride

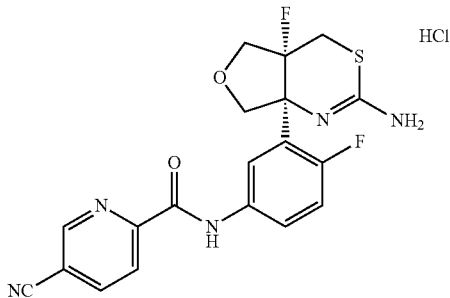 [SMILES: N#Cc1ccc(C(=O)Nc2ccc(F)c([C@]34COC[C@@]3(F)CSC(N)=N4)c2)nc1 ; Cl]

Scheme 2, step K (amide formation): Oxalyl chloride (60.0 µL, 692 mmol) is added to a solution of dimethylformamide (60.0 µL, 776 mmol) in acetonitrile (4.0 mL), and the resulting reaction is stirred for 16 min. 5-Cyanopyridine-2-carboxylic acid (106 mg, 715 mmol) is added to the resulting solution. The reaction is stirred for 33 minutes, and 2.0 mL of this solution is removed via syringe and added drop wise to a solution of (4aR,7aS)-7a-(5-amino-2-fluoro-phenyl)-4a-fluoro-5,7-dihydro-4H-furo[3,4-d][1,3]thiazin-2-amine (110 mg, 347 mmol) in ethanol (2.0 mL) and water (2.0 mL) at 50° C. The resulting solution is heated at 50° C. for 44 minutes followed by purification by SCX columns (methanol to 7 M ammonia in methanol) to give a residue, which is purified again by silica gel flash chromatography, eluting with 7 M ammonia in methanol/dichloromethane (0/10) to 7 M ammonia in methanol/dichloromethane (1/10) to give a residue as the free base of the desired product (120 mg, 83%). This material is dissolved in 5 mL of dichloromethane/methanol (1/1) and is treated with 1 M HCl in ether (300 µL, 0.30 mmol). The sample is concentrated to give the title compound (128 mg, 81.6%). ES/MS (m/e): 416.1 (M+1).

Example 4

N-[3-[(4aR,7aS)-2-Amino-4a-fluoro-5,7-dihydro-4H-furo[3,4-d][1,3]thiazin-7a-yl]-4-fluoro-phenyl]-5-(oxetan-2-ylmethoxy)pyrazine-2-carboxamide

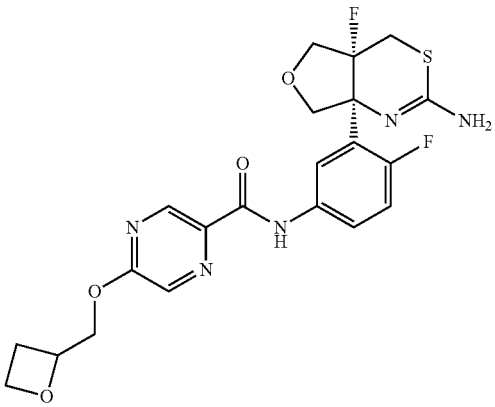 [SMILES: NC1=N[C@@]2(c3cc(NC(=O)c4cnc(OCC5CCO5)cn4)ccc3F)COC[C@@]2(F)CS1]

1-Propanephosphonic acid cyclic anhydride 50 wt % solution in ethyl acetate (8.90 µL, 1.50 mmol) is added to a microwave vial containing a mixture of (4aR,7aS)-7a-(5-amino-2-fluoro-phenyl)-4a-fluoro-5,7-dihydro-4H-furo[3,4-d][1,3]thiazin-2-amine (81.2 mg, 0.285 mmol), 5-(oxetan-2-ylmethoxy)pyrazine-2-carboxylic acid (140 mg, 0.300 mmol) and anhydrous dichloromethane (10 mL). The vial is sealed and the mixture stirred at room temperature overnight. The mixture is then partitioned between water and dichloromethane and the layers separated through a Phase Separating cartridge. Organics are combined and the solvent evaporated under reduced pressure. The resulting oil is dissolved in methanol, filtered, and purified by preparative-HPLC (Phenomenex Gemini 10 µm 50*150 mm C-18) ($CH_3CN$ and water with 10 mM ammonium bicarbonate, 10% to 100% $CH_3CN$ over 10 minutes at 120 ml/min) (1 injection). Fractions bearing product are concentrated to dryness overnight in a centrifugal evaporator to give the title compound as a white solid (40 mg, 28%). ES/MS (m/e): 478.2 (M+1).

The following compounds in Table 2 are prepared in a manner essentially analogous to the method set forth in Examples 1 to 3 utilizing the appropriately substituted carboxylic acid for the amide formation reaction. Each of the examples shown in Examples 1 to 3 and in Table 2 can be prepared as the free base or as a pharmaceutically acceptable salt, such as the HCl salt, as described in Example 3.

Table 2

TABLE 2

| Ex No. | Chemical Name | Structure | ES/MS (m/z) (M + 1) |
|---|---|---|---|
| 5 | N-[3-[(4aR,7aS)-2-Amino-4a-fluoro-5,7-dihydro-4H-furo[3,4-d][1,3]thiazin-7a-yl]-4-fluoro-phenyl]-5-chloro-pyridine-2-carboxamide hydrochloride | 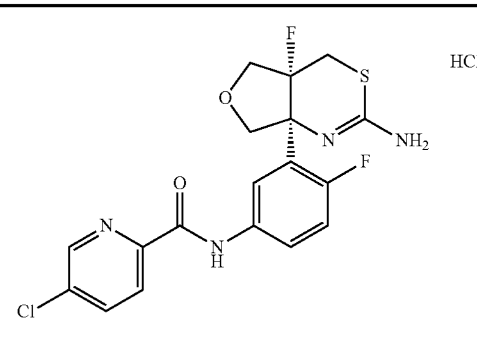 | 425.0 |

TABLE 2-continued

| Ex No. | Chemical Name | Structure | ES/MS (m/z) (M + 1) |
|---|---|---|---|
| 6 | N-[3-[(4aR,7aS)-2-Amino-4a-fluoro-5,7-dihydro-4H-furo[3,4-d][1,3]thiazin-7a-yl]-4-fluoro-phenyl]-3,5-difluoro-pyridine-2-carboxamide hydrochloride | 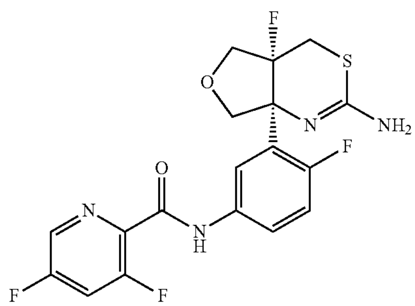 | 427.0 |
| 7 | N-[3-[(4aR,7aS)-2-Amino-4a-fluoro-5,7-dihydro-4H-furo[3,4-d][1,3]thiazin-7a-yl]-4-fluoro-phenyl]-1-(difluoromethyl)pyrazole-3-carboxamide hydrochloride | 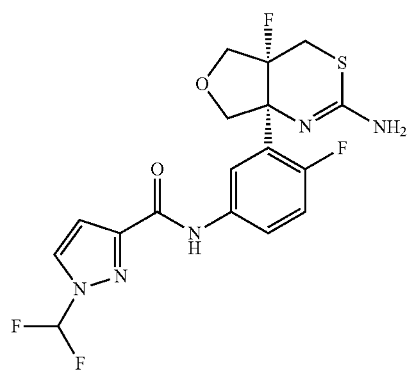 | 430.0 |
| 8 | N-[3-[(4aR,7aS)-2-Amino-4a-fluoro-5,7-dihydro-4H-furo[3,4-d][1,3]thiazin-7a-yl]-4-fluoro-phenyl]-3-chloro-5-cyano-pyridine-2-carboxamide hydrochloride | 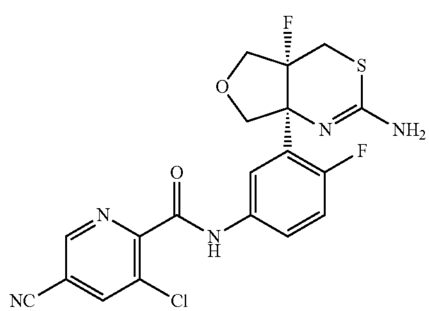 | 450.0 |
| 9 | N-[3-[(4aR,7aS)-2-Amino-4a-fluoro-5,7-dihydro-4H-furo[3,4-d][1,3]thiazin-7a-yl]-4-fluoro-phenyl]-5-methyl-pyrazine-2-carboxamide hydrochloride | 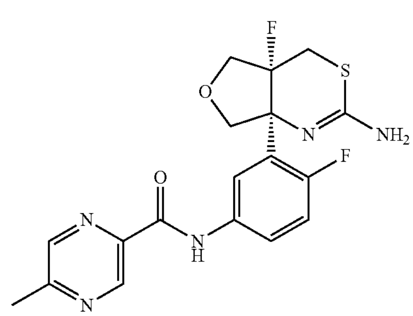 | 406.0 |

TABLE 2-continued

| Ex No. | Chemical Name | Structure | ES/MS (m/z) (M + 1) |
|---|---|---|---|
| 10 | N-[3-[(4aR,7aS)-2-Amino-4a-fluoro-5,7-dihydro-4H-furo[3,4-d][1,3]thiazin-7a-yl]-4-fluoro-phenyl]-5-chloro-pyrimidine-2-carboxamide hydrochloride | 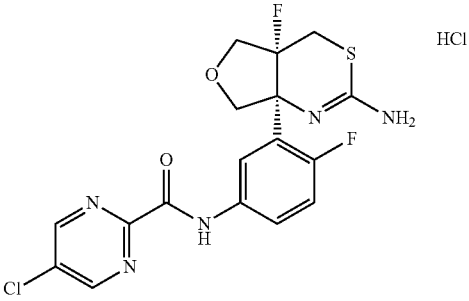 [SMILES: NC1=N[C@@]2(c3cc(NC(=O)c4ncc(Cl)cn4)ccc3F)COC[C@@]2(F)CS1 ; Cl] | 426.0 |
| 11 | N-[3-[(4aR,7aS)-2-Amino-4a-fluoro-5,7-dihydro-4H-furo[3,4-d][1,3]thiazin-7a-yl]-4-fluoro-phenyl]-5-chloro-thiazole-2-carboxamide hydrochloride | 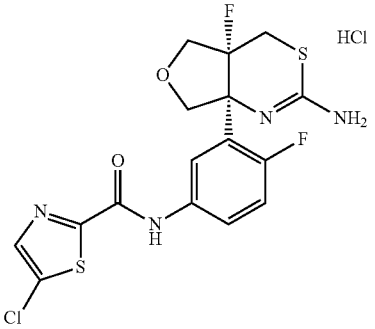 [SMILES: NC1=N[C@@]2(c3cc(NC(=O)c4ncc(Cl)s4)ccc3F)COC[C@@]2(F)CS1 ; Cl] | 431.0 |
| 12 | N-[3-[(4aR,7aS)-2-Amino-4a-fluoro-5,7-dihydro-4H-furo[3,4-d][1,3]thiazin-7a-yl]-4-fluoro-phenyl]-5-(trifluoromethyl)pyrazine-2-carboxamide hydrochloride | 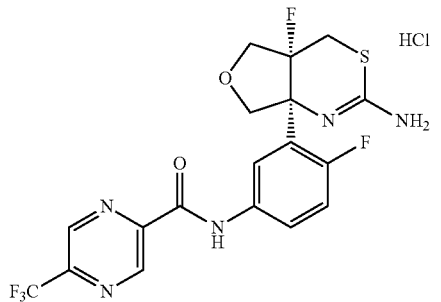 [SMILES: NC1=N[C@@]2(c3cc(NC(=O)c4cnc(C(F)(F)F)cn4)ccc3F)COC[C@@]2(F)CS1 ; Cl] | 460.0 |
| 13 | N-[3-[(4aR,7aS)-2-Amino-4a-fluoro-5,7-dihydro-4H-furo[3,4-d][1,3]thiazin-7a-yl]-4-fluoro-phenyl]-2,5-dimethyl-oxazole-4-carboxamide hydrochloride | 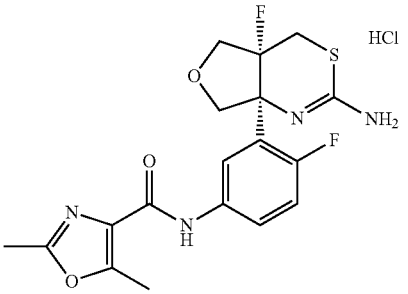 [SMILES: Cc1nc(C(=O)Nc2ccc(F)c([C@]34COC[C@@]3(F)CSC(N)=N4)c2)c(C)o1 ; Cl] | 409.0 |

TABLE 2-continued

| Ex No. | Chemical Name | Structure | ES/MS (m/z) (M + 1) |
|---|---|---|---|
| 14 | N-[3-[(4aR,7aS)-2-Amino-4a-fluoro-5,7-dihydro-4H-furo[3,4-d][1,3]thiazin-7a-yl]-4-fluoro-phenyl]-5-cyclopropyl-pyrazine-2-carboxamide hydrochloride | 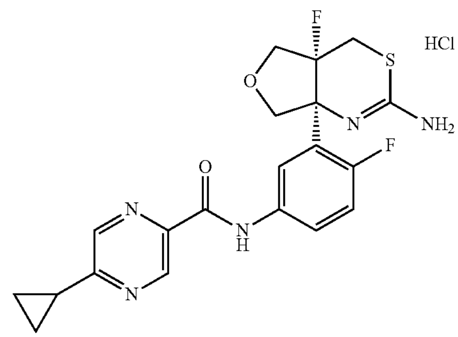 [SMILES: NC1=N[C@@]2(c3cc(NC(=O)c4cnc(C5CC5)cn4)ccc3F)COC[C@@]2(F)CS1 ; Cl] | 433.0 |
| 15 | N-[3-[(4aR,7aS)-2-Amino-4a-fluoro-5,7-dihydro-4H-furo[3,4-d][1,3]thiazin-7a-yl]-4-fluoro-phenyl]-5-(cyclopropylmethoxy)pyrazine-2-carboxamide hydrochloride | 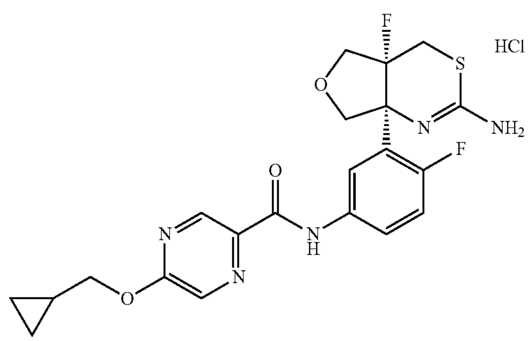 [SMILES: NC1=N[C@@]2(c3cc(NC(=O)c4cnc(OCC5CC5)cn4)ccc3F)COC[C@@]2(F)CS1 ; Cl] | 463.0 |
| 16 | N-[3-[(4aR,7aS)-2-Amino-4a-fluoro-5,7-dihydro-4H-furo[3,4-d][1,3]thiazin-7a-yl]-4-fluoro-phenyl]-5-(2,2,3,3-tetrafluoro-propoxy)pyridine-2-carboxamide hydrochloride | 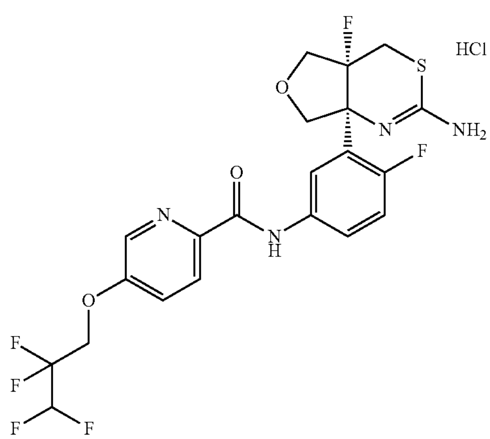 [SMILES: NC1=N[C@@]2(c3cc(NC(=O)c4ccc(OCC(F)(F)C(F)F)cn4)ccc3F)COC[C@@]2(F)CS1 ; Cl] | 521.0 |
| 17 | N-[3-[(4aR,7aS)-2-Amino-4a-fluoro-5,7-dihydro-4H-furo[3,4-d][1,3]thiazin-7a-yl]-4-fluoro-phenyl]-5-cyano-3-fluoro-pyridine-2-carboxamide hydrochloride | 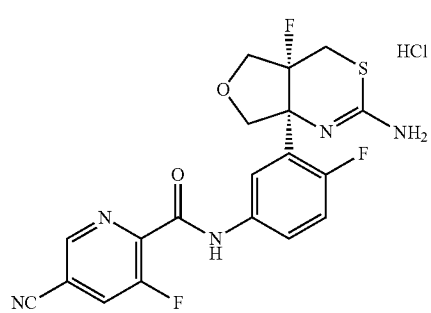 | 434.0 |

TABLE 2-continued

| Ex No. | Chemical Name | Structure | ES/MS (m/z) (M + 1) |
|---|---|---|---|
| 18 | N-[3-[(4aR,7aS)-2-Amino-4a-fluoro-5,7-dihydro-4H-furo[3,4-d][1,3]thiazin-7a-yl]-4-fluoro-phenyl]-5-(cyclopropoxy)pyrazine-2-carboxamide hydrochloride | 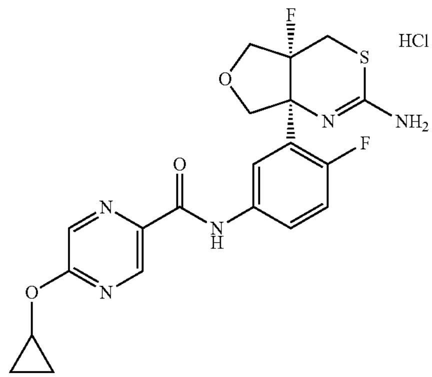 [SMILES: NC1=N[C@@]2(c3cc(NC(=O)c4cnc(OC5CC5)cn4)ccc3F)COC[C@@]2(F)CS1 ; Cl] | 449.0 |
| 19 | N-[3-[(4aR,7aS)-2-Amino-4a-fluoro-5,7-dihydro-4H-furo[3,4-d][1,3]thiazin-7a-yl]-4-fluoro-phenyl]-5-(2,2,2-trifluoroethoxy)pyridine-2-carboxamide hydrochloride | 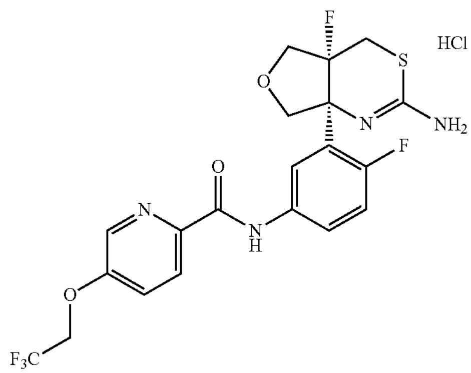 [SMILES: NC1=N[C@@]2(c3cc(NC(=O)c4ccc(OCC(F)(F)F)cn4)ccc3F)COC[C@@]2(F)CS1 ; Cl] | 489.0 |
| 20 | N-[3-[(4aR,7aS)-2-Amino-4a-fluoro-5,7-dihydro-4H-furo[3,4-d][1,3]thiazin-7a-yl]-4-fluoro-phenyl]-5-(2,2,2-trifluoroethoxy)pyrazine-2-carboxamide hydrochloride | 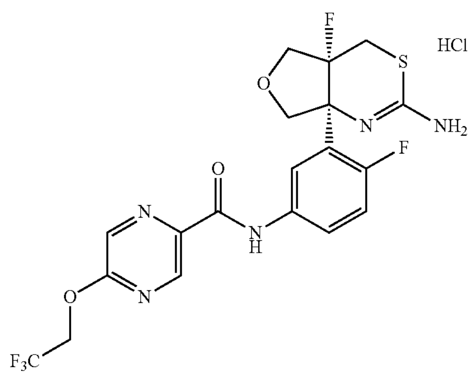 [SMILES: NC1=N[C@@]2(c3cc(NC(=O)c4cnc(OCC(F)(F)F)cn4)ccc3F)COC[C@@]2(F)CS1 ; Cl] | 490.2 |
| 21 | N-[3-[(4aR,7aS)-2-Amino-4a-fluoro-5,7-dihydro-4H-furo[3,4-d][1,3]thiazin-7a-yl]-4-fluoro-phenyl]-5-cyano-3-methyl-pyridine-2-carboxamide hydrochloride | 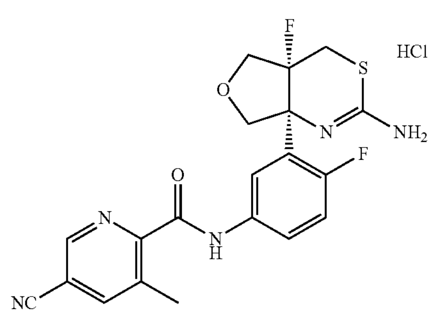 [SMILES: Cc1cc(C#N)cnc1C(=O)Nc1ccc(F)c([C@]23COC[C@@]2(F)CSC(N)=N3)c1 ; Cl] | 430.0 |

TABLE 2-continued

| Ex No. | Chemical Name | Structure | ES/MS (m/z) (M + 1) |
|---|---|---|---|
| 22 | N-[3-[(4aR,7aS)-2-Amino-4a-fluoro-5,7-dihydro-4H-furo[3,4-d][1,3]thiazin-7a-yl]-4-fluoro-phenyl]-5-ethoxy-pyrazine-2-carboxamide hydrochloride | 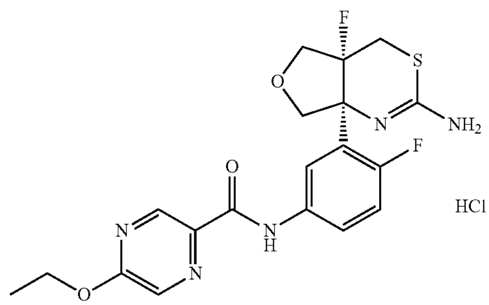 [SMILES: CCOc1cnc(C(=O)Nc2ccc(F)c([C@]34COC[C@@]3(F)CSC(N)=N4)c2)cn1 ; Cl] | 536.0 |
| 23 | N-[3-[(4aR,7aS)-2-Amino-4a-fluoro-5,7-dihydro-4H-furo[3,4-d][1,3]thiazin-7a-yl]-4-fluoro-phenyl]-5-propoxy-pyrazine-2-carboxamide hydrochloride | 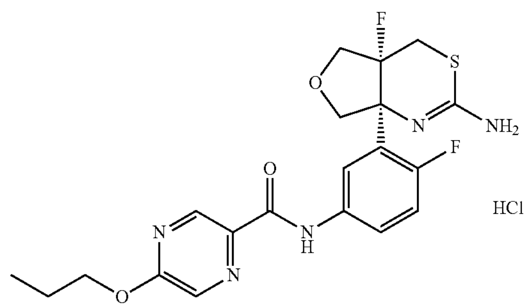 [SMILES: CCCOc1cnc(C(=O)Nc2ccc(F)c([C@]34COC[C@@]3(F)CSC(N)=N4)c2)cn1 ; Cl] | 450.0 |
| 24 | N-[3-[(4aR,7aS)-2-Amino-4a-fluoro-5,7-dihydro-4H-furo[3,4-d][1,3]thiazin-7a-yl]-4-fluoro-phenyl]-5-methoxy-pyrimidine-2-carboxamide hydrochloride | 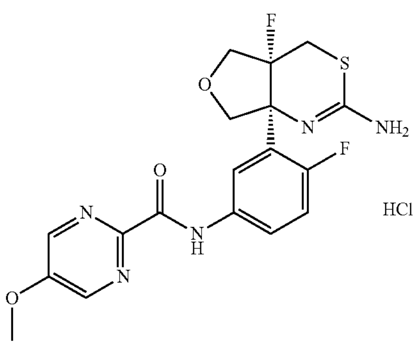 [SMILES: COc1cnc(C(=O)Nc2ccc(F)c([C@]34COC[C@@]3(F)CSC(N)=N4)c2)nc1 ; Cl] | 422.2 |
| 25 | N-[3-[(4aR,7aS)-2-Amino-4a-fluoro-5,7-dihydro-4H-furo[3,4-d][1,3]thiazin-7a-yl]-4-fluorophenyl]-3-fluoro-5-methoxy-pyridine-2-carboxamide hydrochloride | 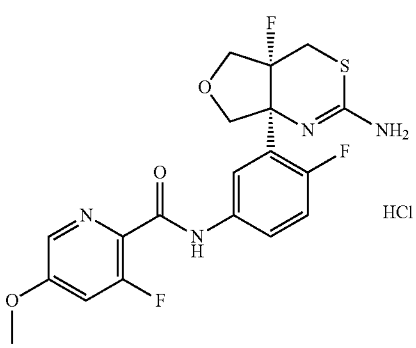 [SMILES: COc1cnc(C(=O)Nc2ccc(F)c([C@]34COC[C@@]3(F)CSC(N)=N4)c2)c(F)c1 ; Cl] | 439.0 |

TABLE 2-continued

| Ex No. | Chemical Name | Structure | ES/MS (m/z) (M + 1) |
|---|---|---|---|
| 26 | N-[3-[(4aR,7aS)-2-Amino-4a-fluoro-5,7-dihydro-4H-furo[3,4-d][1,3]thiazin-7a-yl]-4-fluoro-phenyl]-3-fluoro-5-(2,2,2-trifluoroethoxy)pyridine-2-carboxamide hydrochloride | 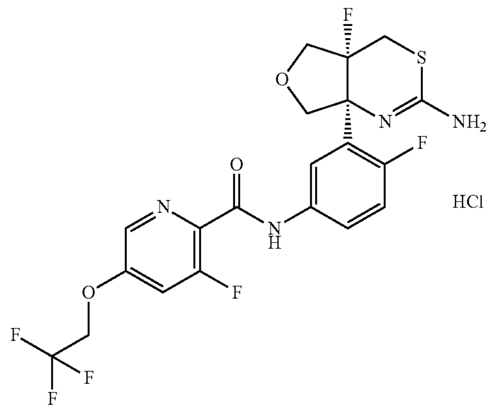 [SMILES: NC1=N[C@@]2(c3cc(NC(=O)c4ncc(OCC(F)(F)F)cc4F)ccc3F)COC[C@@]2(F)CS1 ; Cl] | 507.2 |
| 27 | N-[3-[(4aR,7aS)-2-Amino-4a-fluoro-5,7-dihydro-4H-furo[3,4-d][1,3]thiazin-7a-yl]-4-fluoro-phenyl]-3-fluoro-5-(2,2,3,3-tetrafluoro-propoxy)pyridine-2-carboxamide hydrochloride | 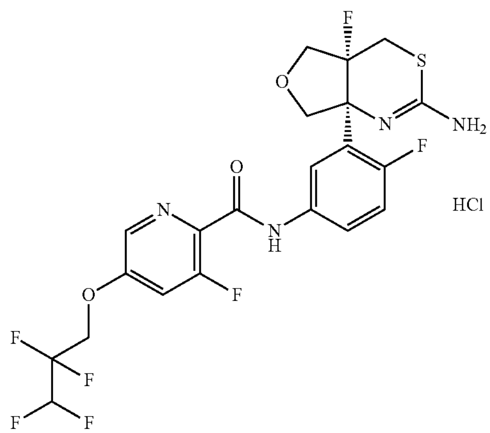 [SMILES: NC1=N[C@@]2(c3cc(NC(=O)c4ncc(OCC(F)(F)C(F)F)cc4F)ccc3F)COC[C@@]2(F)CS1 ; Cl] | 539.0 |
| 28 | N-[3-[(4aR,7aS)-2-Amino-4a-fluoro-5,7-dihydro-4H-furo[3,4-d][1,3]thiazin-7a-yl]-4-fluoro-phenyl]-5-(2,2-difluoroethoxy)pyrazine-2-carboxamide hydrochloride | 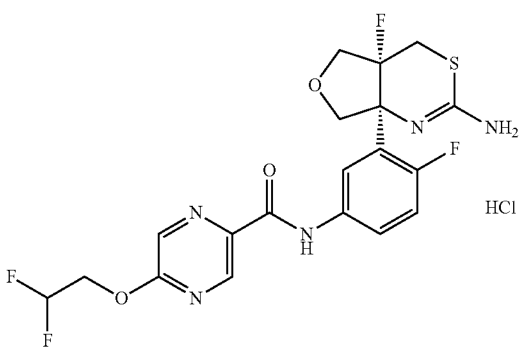 [SMILES: NC1=N[C@@]2(c3cc(NC(=O)c4cnc(OCC(F)F)cn4)ccc3F)COC[C@@]2(F)CS1 ; Cl] | 472.1 |
| 29 | N-[3-[(4aR,7aS)-2-Amino-4a-fluoro-5,7-dihydro-4H-furo[3,4-d][1,3]thiazin-7a-yl]-4-fluoro-phenyl]-5-(2-methoxyethoxy)pyridine-2-carboxamide hydrochloride | 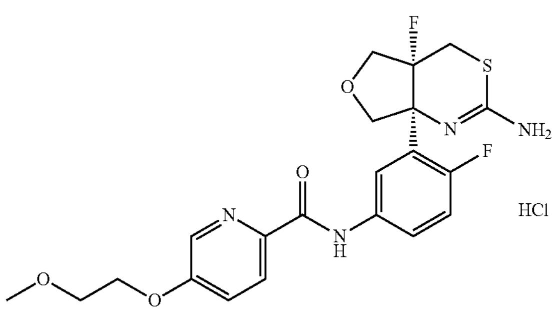 [SMILES: COCCOc1ccc(C(=O)Nc2ccc(F)c([C@]34COC[C@@]3(F)CSC(N)=N4)c2)nc1 ; Cl] | 465.2 |

TABLE 2-continued

| Ex No. | Chemical Name | Structure | ES/MS (m/z) (M + 1) |
|---|---|---|---|
| 30 | N-[3-[(4aR,7aS)-2-Amino-4a-fluoro-5,7-dihydro-4H-furo[3,4-d][1,3]thiazin-7a-yl]-4-fluoro-phenyl]-5-(2-methoxyethoxy)pyrazine-2-carboxamide hydrochloride | 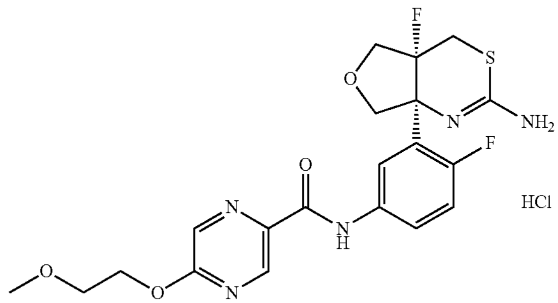 [SMILES: COCCOc1cnc(C(=O)Nc2ccc(F)c([C@]34COC[C@@]3(F)CSC(N)=N4)c2)cn1 ; Cl] | 466.0 |
| 31 | N-[3-[(4aR,7aS)-2-Amino-4a-fluoro-5,7-dihydro-4H-furo[3,4-d][1,3]thiazin-7a-yl]-4-fluoro-phenyl]-5-(2,2,3,3-tetrafluoro-propoxy)pyrazine-2-carboxamide hydrochloride | 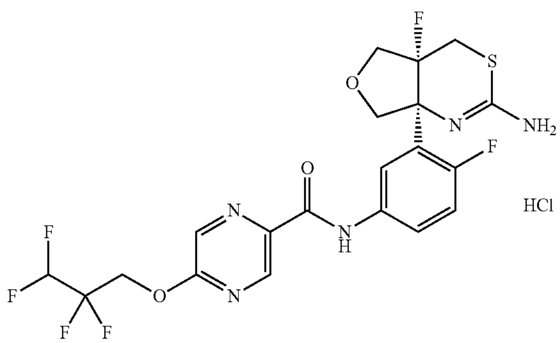 [SMILES: NC1=N[C@@]2(c3cc(NC(=O)c4cnc(OCC(F)(F)C(F)F)cn4)ccc3F)COC[C@@]2(F)CS1 ; Cl] | 522.2 |
| 32 | N-[3-[(4aR,7aS)-2-Amino-4a-fluoro-5,7-dihydro-4H-furo[3,4-d][1,3]thiazin-7a-yl]-4-fluoro-phenyl]-5-[(2,2-difluorocyclo-propyl)methoxy]pyrazine-2-carboxamide hydrochloride | 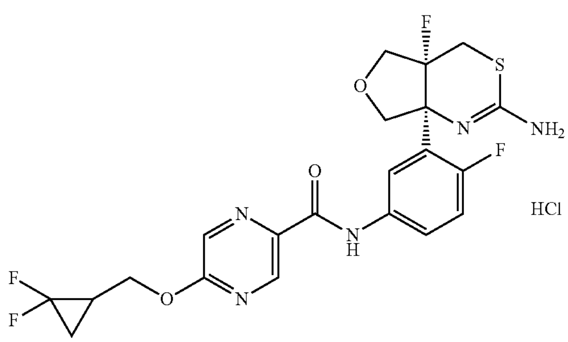 [SMILES: NC1=N[C@@]2(c3cc(NC(=O)c4cnc(OCC5CC5(F)F)cn4)ccc3F)COC[C@@]2(F)CS1 ; Cl] | 498.2 |
| 33 | N-[3-[(4aR,7aS)-2-Amino-4a-fluoro-5,7-dihydro-4H-furo[3,4-d][1,3]thiazin-7a-yl]-4-fluoro-phenyl]-5-(2,2-difluoropropoxy)pyrazine-2-carboxamide hydrochloride | 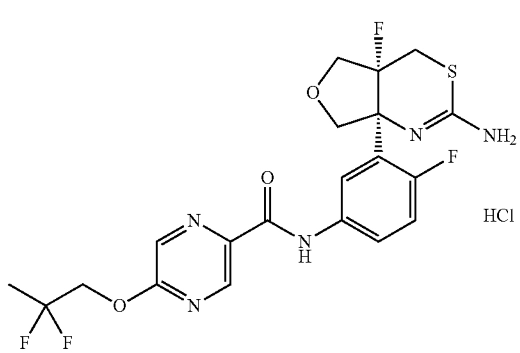 [SMILES: CC(F)(F)COc1cnc(C(=O)Nc2ccc(F)c([C@]34COC[C@@]3(F)CSC(N)=N4)c2)cn1 ; Cl] | 486.2 |

Example 34

N-[3-[(4aR,7aS)-2-Amino-4a-fluoro-5,7-dihydro-4H-furo[3,4-d][1,3]oxazin-7a-yl]-4-fluoro-phenyl]-5-cyano-pyridine-2-carboxamide hydrochloride Method A

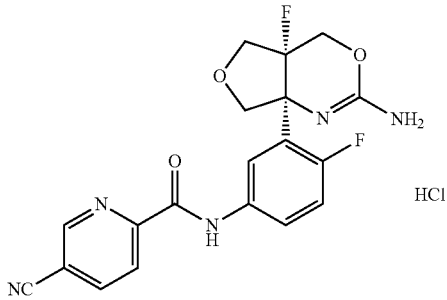 [SMILES: N#Cc1ccc(C(=O)Nc2ccc(F)c([C@]34COC[C@@]3(F)COC(N)=N4)c2)nc1 ; Cl]

The free base N-[3-[(4aR,7aS)-2-amino-4a-fluoro-5,7-dihydro-4H-furo[3,4-d][1,3]oxazin-7a-yl]-4-fluoro-phenyl]-5-cyano-pyridine-2-carboxamide (458 mg, 1.15 mmol, prepared in preparation 15) is dissolved in dichloromethane (3 mL) and methanol (3 mL). Hydrochloric acid (4 M in 1,4-dioxane, 380 µL, 1.52 mmol) is added. The solution is evaporated to dryness to provide the title compound (380 mg, 76%) as a pale yellow solid. ES/MS (m/z): 400 (M+1).

Method B Example 34

To a solution of N-[3-[(4aR,7aS)-2-amino-4a-fluoro-5,7-dihydro-4H-furo[3,4-d][1,3]oxazin-7a-yl]-4-fluoro-phenyl]-5-cyano-pyridine-2-carboxamide (9.1 g, 22.7 mmol) in methanol (182 mL) is added a solution of hydrogen chloride 1.2 M in isopropyl alcohol (18.9 mL, 22.7 mmol). The mixture is stirred for 15 minutes. The solvent is evaporated to give the title compound as white crystalline solid (9.8 g, 99%). ES/MS (m/z): 400 (M+1).

Example 35

N-[3-[(4aR,7aS)-2-Amino-4a-fluoro-5,7-dihydro-4H-furo[3,4-d][1,3]oxazin-7a-yl]-4-fluoro-phenyl]-5-cyano-3-fluoro-pyridine-2-carboxamide hydrochloride

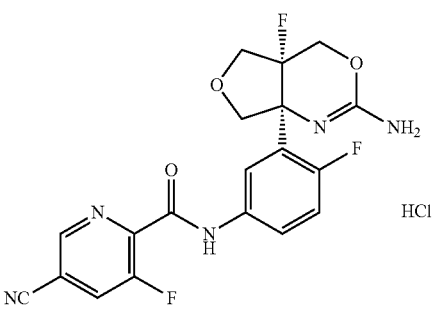 [SMILES: N#Cc1cnc(C(=O)Nc2ccc(F)c([C@]34COC[C@@]3(F)COC(N)=N4)c2)c(F)c1 ; Cl]

Scheme 3, step M, substep 2 (amidation): Dimethylformamide (10 µL, 0.14 mmol) and oxalyl chloride (119 µL, 1.38 mmol) is added to acetonitrile (3.7 mL) and stirred at room temperature for 10 minutes. 5-Cyano-3-fluoro-pyridine-2-carboxylic acid (213 mg, 1.28 mmol) is added and the mixture is stirred for another 10 minutes. This mixture is then added in a single portion to a solution of (4aR,7aS)-7a-(5-amino-2-fluoro-phenyl)-4a-fluoro-5,7-dihydro-4H-furo[3,4-d][1,3]oxazin-2-amine (247 mg, 0.917 mmol) in ethanol (3.7 mL) and water (3.7 mL) heated to 55° C. The reaction mixture is stirred for 1.5 hours and then concentrated under reduced pressure. The residue is diluted with ethyl acetate, washed with ½ saturated sodium bicarbonate solution. The aqueous layer is extracted with ethyl acetate, and the combined organic layers are dried over sodium sulfate, filtered, and concentrated to give a residue, which is purified by silica gel flash chromatography eluting with a gradient of 7 M ammonia in methanol/dichloromethane (1/99) to 7 M ammonia in methanol/dichloromethane (10/90) to give the free base of the title compound (328 mg, 0.786 mmol). The free base is dissolved in dichloromethane (5 mL) and methanol (0.2 mL), and treated with hydrochloric acid (1 M in diethyl ether, 865 µL, 0.865 mmol), and concentrated under reduced pressure. Diethyl ether (3 mL) is added to the residue and concentrated and this is repeated a second time to give the title compound (349 mg, 0.769 mmol, 83.8%). ES/MS (m/z): 418.0 (M+1).

The following compounds listed in Table 3 are prepared in a manner essentially analogous to the method set forth in Example 35 utilizing the appropriately substituted carboxylic acid in the amide formation reaction. In addition, the HCl salt is prepared from the corresponding free base in a manner analogous to the method described in Example 35.

TABLE 3

| Ex No. | Chemical Name | Structure | ES/MS (m/z) (M + 1) |
|---|---|---|---|
| 36 | N-[3-[(4aR,7aS)-2-Amino-4a-fluoro-5,7-dihydro-4H-furo[3,4-d][1,3]oxazin-7a-yl]-4-fluoro-phenyl]-5-chloro-pyridine-2-carboxamide hydrochloride (The corresponding free base is prepared in preparation 16) | 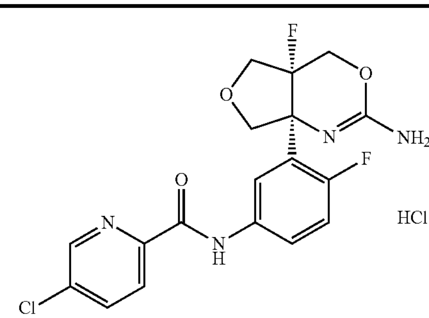 | 409.1 |

TABLE 3-continued

| Ex No. | Chemical Name | Structure | ES/MS (m/z) (M + 1) |
|---|---|---|---|
| 37 | N-[3-[(4aR,7aS)-2-Amino-4a-fluoro-5,7-dihydro-4H-furo[3,4-d][1,3]oxazin-7a-yl]-4-fluoro-phenyl]-5-methoxy-pyrazine-2-carboxamide hydrochloride | 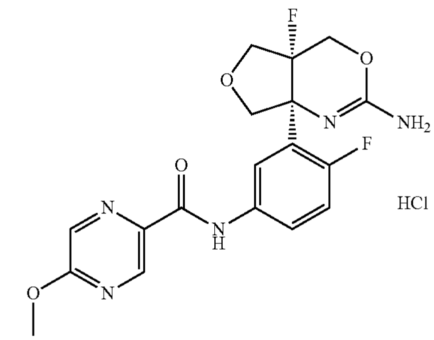 [SMILES: COc1cnc(C(=O)Nc2ccc(F)c([C@]34COC[C@@]3(F)COC(N)=N4)c2)cn1 ; Cl] | 406.0 |
| 38 | N-[3-[(4aR,7aS)-2-Amino-4a-fluoro-5,7-dihydro-4H-furo[3,4-d][1,3]oxazin-7a-yl]-4-fluoro-phenyl]-5-fluoro-pyridine-2-carboxamide hydrochloride | 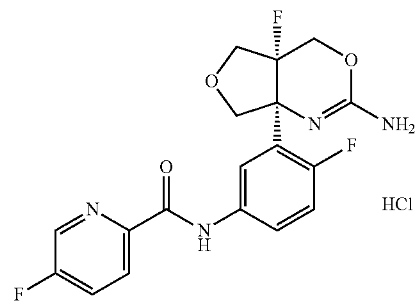 [SMILES: NC1=N[C@@]2(c3cc(NC(=O)c4ccc(F)cn4)ccc3F)COC[C@@]2(F)CO1 ; Cl] | 393.1 |
| 39 | N-[3-[(4aR,7aS)-2-Amino-4a-fluoro-5,7-dihydro-4H-furo[3,4-d][1,3]oxazin-7a-yl]-4-fluoro-phenyl]-5-cyano-3-methyl-pyridine-2-carboxamide hydrochloride | 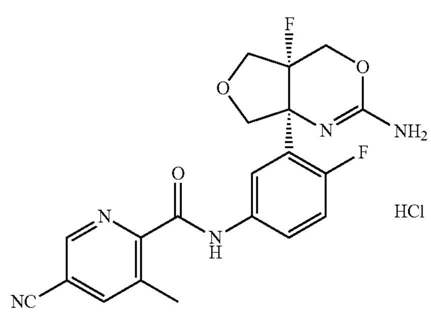 [SMILES: Cc1cc(C#N)cnc1C(=O)Nc1ccc(F)c([C@]23COC[C@@]2(F)COC(N)=N3)c1 ; Cl] | 414.1 |
| 40 | N-[3-[(4aR,7aS)-2-Amino-4a-fluoro-5,7-dihydro-4H-furo[3,4-d][1,3]oxazin-7a-yl]-4-fluoro-phenyl]-5-(2,2,2-trifluoroethoxy)pyridine-2-carboxamide hydrochloride | 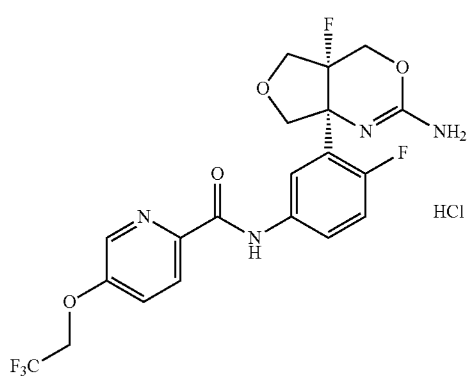 [SMILES: NC1=N[C@@]2(c3cc(NC(=O)c4ccc(OCC(F)(F)F)cn4)ccc3F)COC[C@@]2(F)CO1 ; Cl] | 473.4 |

TABLE 3-continued

| Ex No. | Chemical Name | Structure | ES/MS (m/z) (M + 1) |
|---|---|---|---|
| 41 | N-[3-[(4aR,7aS)-2-Amino-4a-fluoro-5,7-dihydro-4H-furo[3,4-d][1,3]oxazin-7a-yl]-4-fluoro-phenyl]-5-(2,2,2-trifluoro-ethoxy)pyrazine-2-carboxamide hydrochloride | 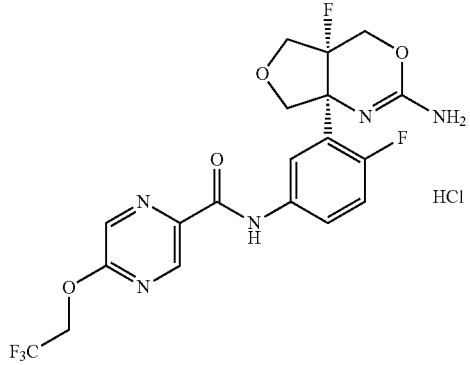 | 474.4 |
| 42 | N-[3-[(4aR,7aS)-2-Amino-4a-fluoro-5,7-dihydro-4H-furo[3,4-d][1,3]oxazin-7a-yl]-4-fluoro-phenyl]-3-chloro-5-cyano-pyridine-2-carboxamide hydrochloride | 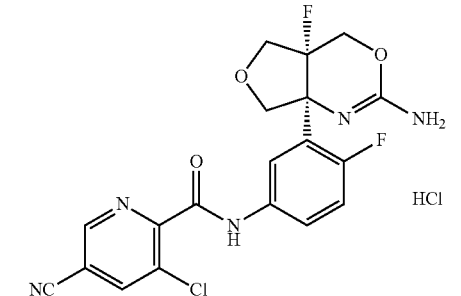 [SMILES: N#Cc1cnc(C(=O)Nc2ccc(F)c([C@]34COC[C@@]3(F)COC(N)=N4)c2)c(Cl)c1 ; Cl] | 434.1 |
| 43 | N-[3-[(4aR,7aS)-2-Amino-4a-fluoro-5,7-dihydro-4H-furo[3,4-d][1,3]oxazin-7a-yl]-4-fluoro-phenyl]-3,5-dichloro-pyridine-2-carboxamide hydrochloride | 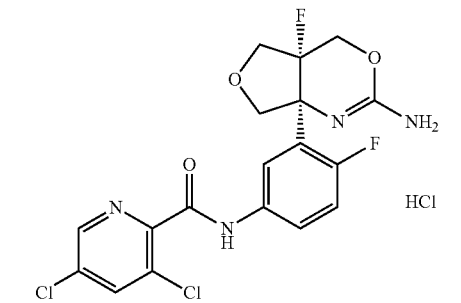 [SMILES: NC1=N[C@@]2(c3cc(NC(=O)c4ncc(Cl)cc4Cl)ccc3F)COC[C@@]2(F)CO1 ; Cl] | 443.0 |
| 44 | N-[3-[(4aR,7aS)-2-Amino-4a-fluoro-5,7-dihydro-4H-furo[3,4-d][1,3]oxazin-7a-yl]-4-fluoro-phenyl]-5-(2,2,3,3-tetrafluoro-propoxy)pyrazine-2-carboxamide hydrochloride | 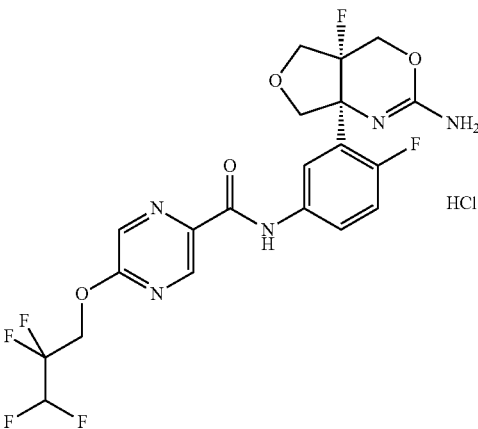 [SMILES: NC1=N[C@@]2(c3cc(NC(=O)c4cnc(OCC(F)(F)C(F)F)cn4)ccc3F)COC[C@@]2(F)CO1 ; Cl] | 506.1 |

TABLE 3-continued

| Ex No. | Chemical Name | Structure | ES/MS (m/z) (M + 1) |
|---|---|---|---|
| 45 | N-[3-[(4aR,7aS)-2-Amino-4a-fluoro-5,7-dihydro-4H-furo[3,4-d][1,3]oxazin-7a-yl]-4-fluoro-phenyl]-5-(2,2,3,3-tetrafluoro-propoxy)pyridine-2-carboxamide hydrochloride | 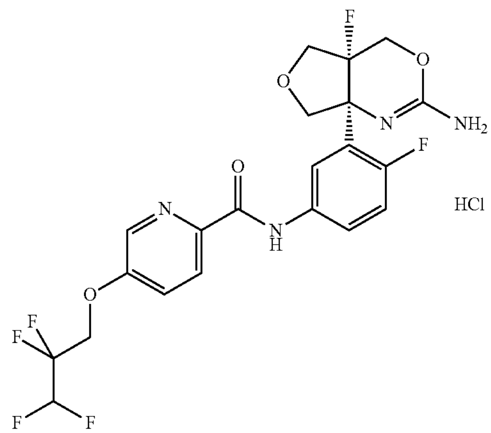 [SMILES: NC1=N[C@@]2(c3cc(NC(=O)c4ccc(OCC(F)(F)C(F)F)cn4)ccc3F)COC[C@@]2(F)CO1 ; Cl] | 505.2 |
| 46 | N-[3-[(4aR,7aS)-2-Amino-4a-fluoro-5,7-dihydro-4H-furo[3,4-d][1,3]oxazin-7a-yl]-4-fluoro-phenyl]-5-(2-methoxyethoxy)pyrazine-2-carboxamide hydrochloride | 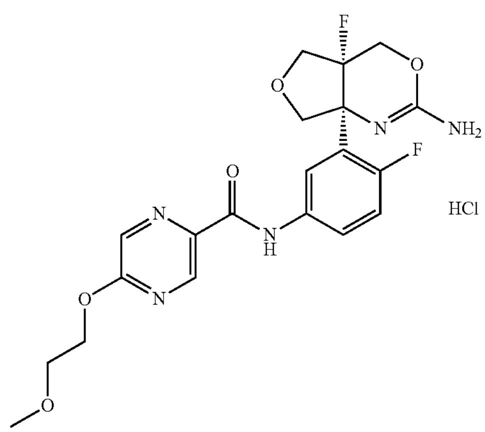 [SMILES: COCCOc1cnc(C(=O)Nc2ccc(F)c([C@]34COC[C@@]3(F)COC(N)=N4)c2)cn1 ; Cl] | 450.2 |
| 47 | N-[3-[(4aR,7aS)-2-Amino-4a-fluoro-5,7-dihydro-4H-furo[3,4-d][1,3]oxazin-7a-yl]-4-fluoro-phenyl]-3-fluoro-5-methoxy-pyridine-2-carboxamide hydrochloride | 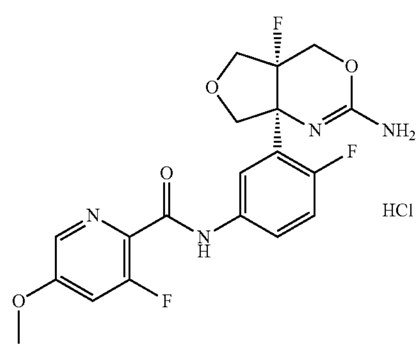 [SMILES: COc1cnc(C(=O)Nc2ccc(F)c([C@]34COC[C@@]3(F)COC(N)=N4)c2)c(F)c1 ; Cl] | 423.0 |

TABLE 3-continued

| Ex No. | Chemical Name | Structure | ES/MS (m/z) (M + 1) |
|---|---|---|---|
| 48 | N-[3-[(4aR,7aS)-2-Amino-4a-fluoro-5,7-dihydro-4H-furo[3,4-d][1,3]oxazin-7a-yl]-4-fluoro-phenyl]-5-propoxy-pyrazine-2-carboxamide hydrochloride | 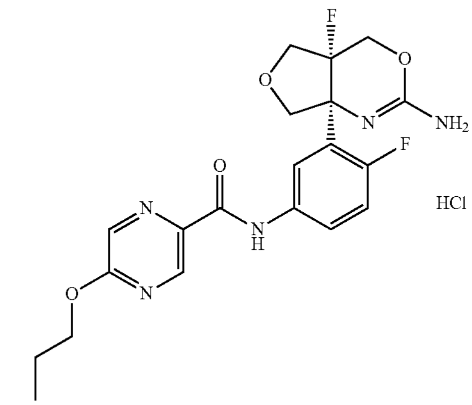 [SMILES: CCCOc1cnc(C(=O)Nc2ccc(F)c([C@]34COC[C@@]3(F)COC(N)=N4)c2)cn1 ; Cl] | 434.2 |
| 49 | N-[3-[(4aR,7aS)-2-Amino-4a-fluoro-5,7-dihydro-4H-furo[3,4-d][1,3]oxazin-7a-yl]-4-fluoro-phenyl]-5-(2-methoxyethoxy)pyridine-2-carboxamide hydrochloride | 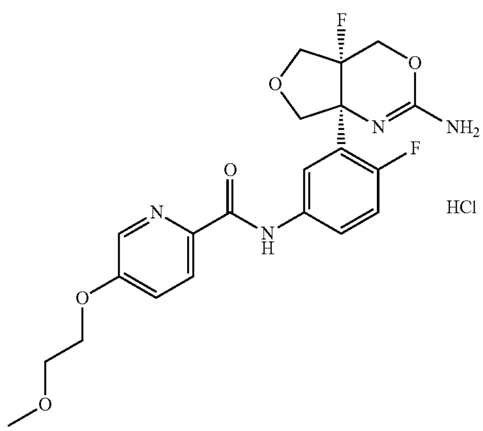 [SMILES: COCCOc1ccc(C(=O)Nc2ccc(F)c([C@]34COC[C@@]3(F)COC(N)=N4)c2)nc1 ; Cl] | 449.0 |
| 50 | N-[3-[(4aR,7aS)-2-Amino-4a-fluoro-5,7-dihydro-4H-furo[3,4-d][1,3]oxazin-7a-yl]-4-fluoro-phenyl]-5-ethoxy-pyrazine-2-carboxamide hydrochloride | 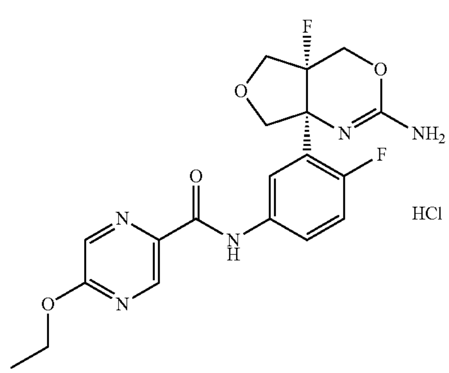 [SMILES: CCOc1cnc(C(=O)Nc2ccc(F)c([C@]34COC[C@@]3(F)COC(N)=N4)c2)cn1 ; Cl] | 420.0 |

TABLE 3-continued

| Ex No. | Chemical Name | Structure | ES/MS (m/z) (M + 1) |
|---|---|---|---|
| 51 | N-[3-[(4aR,7aS)-2-Amino-4a-fluoro-5,7-dihydro-4H-furo[3,4-d][1,3]oxazin-7a-yl]-4-fluoro-phenyl]-3-fluoro-5-(2,2,2-trifluoroethoxy)pyridine-2-carboxamide hydrochloride | 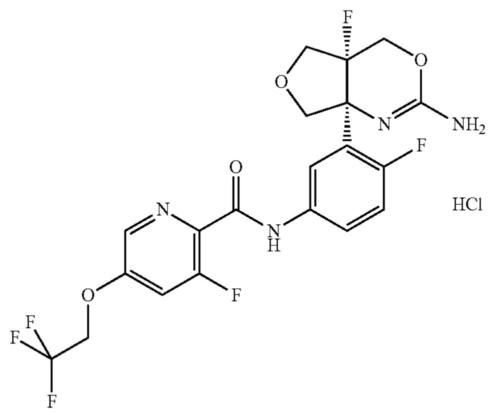 [SMILES: NC1=N[C@@]2(c3cc(NC(=O)c4ncc(OCC(F)(F)F)cc4F)ccc3F)COC[C@@]2(F)CO1 ; Cl] | 491.1 |
| 52 | N-[3-[(4aR,7aS)-2-Amino-4a-fluoro-5,7-dihydro-4H-furo[3,4-d][1,3]oxazin-7a-yl]-4-fluoro-phenyl]-3-fluoro-5-(2,2,3,3-tetrafluoropropoxy)pyridine-2-carboxamide hydrochloride | 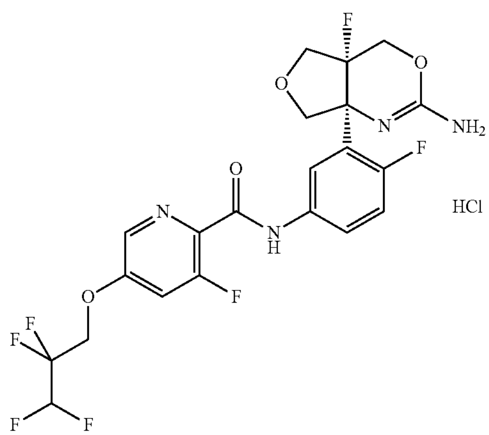 [SMILES: NC1=N[C@@]2(c3cc(NC(=O)c4ncc(OCC(F)(F)C(F)F)cc4F)ccc3F)COC[C@@]2(F)CO1 ; Cl] | 523.0 |
| 53 | N-[3-[(4aR,7aS)-2-Amino-4a-fluoro-5,7-dihydro-4H-furo[3,4-d][1,3]oxazin-7a-yl]-4-fluoro-phenyl]-5-(2,2-difluoroethoxy)pyrazine-2-carboxamide hydrochloride | 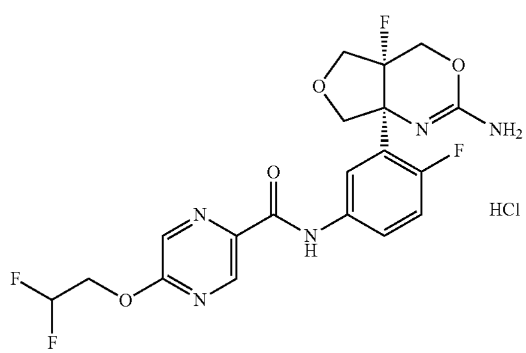 | 456.0 |
| 54 | N-[3-[(4aR,7aS)-2-Amino-4a-fluoro-5,7-dihydro-4H-furo[3,4-d][1,3]oxazin-7a-yl]-4-fluoro-phenyl]-5-[(2,2-difluorocyclopropyl)methoxy]pyrazine-2-carboxamide hydrochloride | 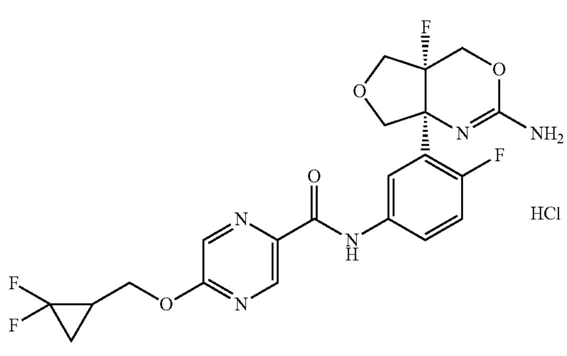 [SMILES: NC1=N[C@@]2(c3cc(NC(=O)c4cnc(OCC5CC5(F)F)cn4)ccc3F)COC[C@@]2(F)CO1 ; Cl] | 482.1 |

TABLE 3-continued

| Ex No. | Chemical Name | Structure | ES/MS (m/z) (M + 1) |
|---|---|---|---|
| 55 | N-[3-[(4aR,7aS)-2-Amino-4a-fluoro-5,7-dihydro-4H-furo[3,4-d][1,3]oxazin-7a-yl]-4-fluoro-phenyl]-5-(2,2-difluoropropoxy)pyrazine-2-carboxamide hydrochloride | 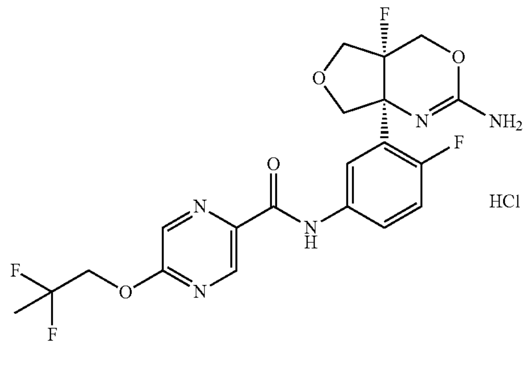 [SMILES: CC(F)(F)COc1cnc(C(=O)Nc2ccc(F)c([C@]34COC[C@@]3(F)COC(N)=N4)c2)cn1 ; Cl] | 470.0 |
| 56 | N-[3-[(4aR,7aS)-2-Amino-4a-fluoro-5,7-dihydro-4H-furo[3,4-d][1,3]oxazin-7a-yl]-4-fluoro-phenyl]-5-(2,2-difluoroethoxy)-3-fluoro-pyridine-2-carboxamide hydrochloride | 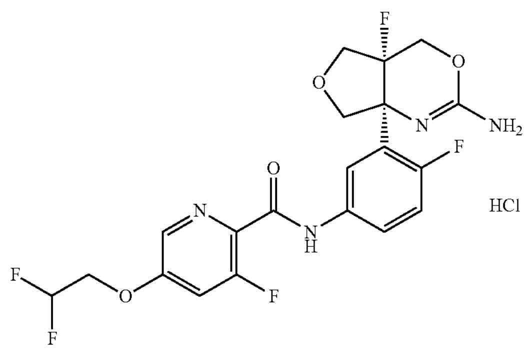 [SMILES: NC1=N[C@@]2(c3cc(NC(=O)c4ncc(OCC(F)F)cc4F)ccc3F)COC[C@@]2(F)CO1 ; Cl] | 473.1 |

Example 57

N-[3-[(4aR,7aS)-2-Amino-4a-fluoro-5,7-dihydro-4H-furo[3,4-d][1,3]oxazin-7a-yl]-4-fluoro-phenyl]-5-[(1-fluorocyclopropyl)methoxy]pyrazine-2-carboxamide hydrochloride

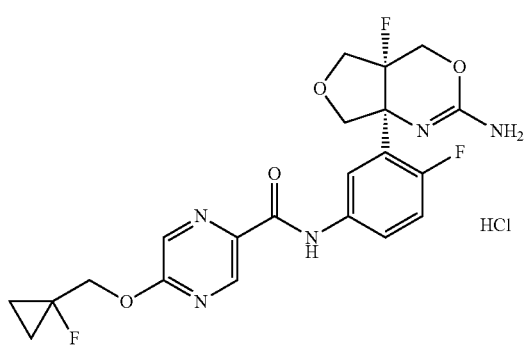 [SMILES: NC1=N[C@@]2(c3cc(NC(=O)c4cnc(OCC5(F)CC5)cn4)ccc3F)COC[C@@]2(F)CO1 ; Cl]

N-[3-[(4aR,7aS)-2-Amino-4a-fluoro-5,7-dihydro-4H-furo[3,4-d][1,3]oxazin-7a-yl]-4-fluoro-phenyl]-5-chloro-pyrazine-2-carboxamide (110 mg, 268. μmol), (1-fluorocyclopropyl)methanol (73 mg, 805 μmol) and potassium carbonate (111 mg, 805.31 μmol) are combined in a microwave vial. Acetonitrile (3 mL) is added and the reaction mixture is heated at 150° C. for 1.5 hours in a microwave reactor. The reaction mixture is diluted with ethyl acetate and the organic layer is washed with saturated aqueous NaHCO$_3$ and water. The combined aqueous layers are extracted twice with ethyl acetate dried with MgSO$_4$ and the solvent removed in vacuo to give the crude product. The crude product is purified by silica gel flash chromatography, eluting with 0-3% (7 N NH$_3$-methanol) in dichloromethane to give the free base of the title product (37 mg, 30%). The free base is dissolved in dichloromethane (2 mL) and treated with hydrochloric acid (1 M in diethyl ether, 80 μL, 80 μmol), and concentrated under reduced pressure to give the title product (39 mg, 29%). ES/MS (m/e): 464 (M+1)

The following compound shown in Table 4 is prepared in a manner essentially analogous to the method set forth in Example 57 utilizing 2-fluoroprop-2-en-1-ol. In addition, the HCl salt is prepared from the corresponding free base in a manner analogous to the method described in Example 35.

TABLE 4

| Ex No. | Chemical Name | Structure | ES/MS (m/z) (M + 1) |
|---|---|---|---|
| 58 | N-[3-[(4aR,7aS)-2-Amino-4a-fluoro-5,7-dihydro-4H-furo[3,4-d][1,3]oxazin-7a-yl]-4-fluorophenyl]-5-(2-fluoroallyloxy)pyrazine-2-carboxamide hydrochloride | 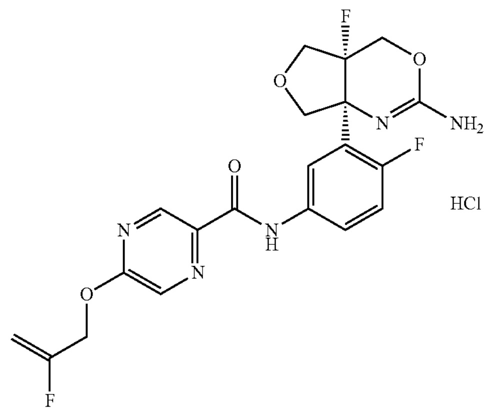 [SMILES: C=C(F)COc1cnc(C(=O)Nc2ccc(F)c([C@]34COC[C@@]3(F)COC(N)=N4)c2)cn1 ; Cl] | 450.0 |

In Vitro Assay Procedures:

For in vitro enzymatic and cellular assays, test compounds are prepared in DMSO to make up a 10 mM stock solution. The stock solution is serially diluted in DMSO to obtain a ten-point dilution curve with final compound concentrations ranging from 10 µM to 0.05 nM in a 96-well round-bottom plate before conducting the in vitro enzymatic and whole cell assays.

In Vitro Protease Inhibition Assays:

Expression and Purification of huBACE1:Fc

Human BACE1 (accession number: AF190725) is cloned from total brain cDNA by RT-PCR. The nucleotide sequences corresponding to amino acid sequences #1 to 460 are inserted into the cDNA encoding human $IgG_1$ (Fc) polypeptide (Vassar et al., Science, 286, 735-742 (1999)). This fusion protein of BACE1 (1-460) and human Fc, named huBACE1:Fc, is constructed into the pJB02 vector. Human BACE1 (1-460):Fc (huBACE1:Fc) is transiently expressed in HEK293 cells. 250 µg cDNA of each construct is mixed with Fugene 6 and added to 1 liter HEK293 cells. Four days after the transfection, conditioned media are harvested for purification. huBACE1:Fc is purified by Protein A chromatography. The enzyme is stored at −80° C. in small aliquots. (See Yang, et. al., J. Neurochemistry, 91(6) 1249-59 (2004)

BACE1 FRET Assay

Serial dilutions of test compounds are prepared as described above. Compounds are further diluted 20× in $KH_2PO_4$ buffer. Ten µL of each dilution is added to each well on row A to H of a corresponding low protein binding black plate containing the reaction mixture (25 µL of 50 mM $KH_2PO_4$, pH 4.6, 1 mM TRITON® X-100, 1 mg/mL Bovine Serum Albumin, and 15 µM of FRET substrate) (See Yang, et. al., J. Neurochemistry, 91(6) 1249-59 (2004)). The content is mixed well on a plate shaker for 10 minutes. Fifteen µL of two hundred pM human BACE1 (1-460):Fc (See Vasser, et al., Science, 286, 735-741 (1999)) in the $KH_2PO_4$ buffer is added to the plate containing substrate and test compounds to initiate the reaction. The RFU of the mixture at time 0 is recorded at excitation wavelength 355 nm and emission wavelength 460 nm, after brief mixing on a plate shaker. The reaction plate is covered with aluminum foil and kept in a dark humidified oven at room temperature for 16 to 24 h. The RFU at the end of incubation is recorded with the same excitation and emission settings used at time 0. The difference of the RFU at time 0 and the end of incubation is representative of the activity of BACE1 under the compound treatment. RFU differences are plotted versus inhibitor concentration and a curve is fitted with a four-parameter logistic equation to obtain the $IC_{50}$ values. (May, et al., Journal of Neuroscience, 31, 16507-16516 (2011)).

The compounds of Examples 1-58 herein are tested essentially as described above and exhibit an $IC_{50}$ for BACE1 of lower than about 1 µM, with the compounds of Examples 1, 2, 3, 34, and 57 exhibiting the following activity as shown in Table 5.

TABLE 5

| Example # | BACE1 $IC_{50}$ (nM) |
|---|---|
| 1 | 15.6 (±3.78, n = 14) |
| 2 | 13.2 (±2.70, n = 7) |
| 3 | 6.66 (±0.538, n = 4) |
| 34 | 45.0 (±13.0, n = 5) |
| 57 | 25.7 (±2.12, n = 2) |

Mean ± SEM; SEM = standard error of the mean

This data demonstrates that the compounds of Examples 1 to 58 inhibit purified recombinant BACE1 enzyme activity in vitro.

PDAPP Primary Neuronal Assay

A confirmatory whole cell assay is also run in primary neuronal cultures generated from PDAPP transgenic embryonic mice (May, et al., Journal of Neuroscience, 31, 16507-16516 (2011)). Primary cortical neurons are prepared from Embryonic Day 16 PDAPP embryos and cultured in 96 well plates ($15 \times 10^4$ cells/well in DMEM/F12 (1:1) plus 10% FBS). After 2 days in vitro, culture media is replaced with serum free DMEM/F12 (1:1) containing B27 supplement and 2 µM (final) of Ara-C (Sigma, C1768). At day 5 in vitro, neurons are incubated at 37° C. for 24 h in the presence/absence of inhibitors (diluted in DMSO) at the desired concentration. At the end of the incubation, conditioned media are analyzed for evidence of beta-secretase activity, for example, by analysis of Abeta peptides 1-40 and 1-42 by specific sandwich ELISAs. To measure these specific isoforms of Abeta, monoclonal 2G3 is used as a capture antibody for Abeta 1-40, and monoclonal 21F12 as a capture antibody for Abeta 1-42. Both Abeta 1-40 and Abeta 1-42 ELISAs use biotinylated 3D6 as the reporting antibody (for description of antibodies, see Johnson-Wood, et al., *Proc. Natl. Acad. Sci. USA* 94, 1550-1555 (1997)). The concentration of Abeta released in the conditioned media following the compound treatment corresponds to the activity of BACE1 under such conditions. The 10-point inhibition curve is plotted and fitted with the four-parameter logistic equation to obtain the $IC_{50}$ values for the Abeta-lowering effect. The following exemplified compounds are tested essentially as described above and exhibit the following activity for Abeta-lowering effect:

TABLE 6

| Example | PDAPP Neuron A-beta (1-40) ELISA $IC_{50}$ (nM) | PDAPP Neuron A-beta (1-42) ELISA $IC_{50}$ (nM) |
|---|---|---|
| 1 | 83.3 (±36.3, n = 4) | 76.8 (±44.8, n = 4) |
| 2 | 29.5 (±18.4, n = 3) | 21.9 (±11.7, n = 2) |
| 3 | 20.2 (±2.32, n = 4) | 16.3 (±11.3, n = 4) |
| 34 | 49.9 (±5.61, n = 3) | 36.5 (±7.41, n = 3) |
| 57 | 186 | 182 |

Mean ± SEM; SEM = standard error of the mean

This data demonstrates that the compounds of Table 6 inhibit Abeta production in whole cells In vivo Inhibition of Beta-Secretase Several animal models, including mouse, guinea pig, dog, and monkey, may be used to screen for inhibition of beta-secretase activity in vivo following compound treatment Animals used in this invention can be wild type, transgenic, or gene knockout animals. For example, the PDAPP mouse model, prepared as described in Games et al., *Nature* 373, 523-527 (1995), and other non-transgenic or gene knockout animals are useful to analyze in vivo inhibition of Abeta and sAPPbeta production in the presence of inhibitory compounds. Generally, 2 month old PDAPP mice, gene knockout mice or non-transgenic animals are administered compound formulated in vehicles, such as corn oil, beta-cyclodextran, phosphate buffers, PHARMASOLVE®, or other suitable vehicles via oral, subcutaneous, intra-venous, feeding or other route of administration. One to twenty-four hours following the administration of compound, animals are sacrificed, and brains are removed for analysis of Abeta 1-x. "Abeta 1-x" as used herein refers to the sum of Abeta species that begin with residue 1 and end with a C-terminus greater than residue 28. This detects the majority of Abeta species and is often called "total Abeta". Total Abeta peptides (Abeta 1-x) levels are measured by a sandwich ELISA, using monoclonal 266 as a capture antibody and biotinylated 3D6 as reporting antibody. (See May, et al., *Journal of Neuroscience*, 31, 16507-16516 (2011)).

For acute studies, compound or appropriate vehicle is administered and animals are sacrificed at about 3 hours after dosing. Brain tissue, is obtained from selected animals and analyzed for the presence of Abeta 1-x. After chronic dosing brain tissues of older APP transgenic animals may also be analyzed for the amount of beta-amyloid plaques following compound treatment.

Animals (PDAPP or other APP transgenic or non-transgenic mice) administered an inhibitory compound may demonstrate the reduction of Abeta in brain tissues, as compared with vehicle-treated controls or time zero controls. For example, three hours following a 30 mg/kg oral dose of the compound of Example 1 to young female PDAPP mice, Abeta 1-x peptide levels are reduced approximately 37% in brain hippocampus, and approximately 48% in brain cortex, p<0.01, compared to vehicle-treated mice. For Example 2, a 10 mg/kg oral dose to young female PDAPP mice, Abeta 1-x peptide levels are reduced approximately 40% in brain hippocampus and approximately 45% in brain cortex, p<0.01, compared to vehicle-treated mice three hours after dosing. For a 30 mg/kg oral dose of Example 2 to young female PDAPP mice, Abeta 1-x peptide levels are reduced approximately 52% in brain hippocampus, and approximately 54% in brain cortex, p<0.01, compared to vehicle-treated mice three hours after dosing. For Example 3, a 10 mg/kg oral dose to young female PDAPP mice, Abeta 1-x peptide levels are reduced approximately 34% in brain hippocampus and approximately 46% in brain cortex, p<0.01, compared to vehicle-treated mice three hours after dosing. For Example 34, three hours following a 10 mg/kg oral dose of the compound of Example 34 to young female PDAPP mice, Abeta 1-x peptide levels are reduced approximately 26%, p<0.05, in brain hippocampus, and approximately 36% and 24% in brain cortex for n=2 and p<0.01, compared to vehicle-treated mice.

Given the activity of Examples 1, 2, 3, and 34 against the BACE enzyme in vitro, these Abeta-lowering effects are consistent with BACE inhibition in vivo, and further demonstrate CNS penetration of Examples 1, 2, 3, and 34.

These studies show that compounds of the present invention inhibit BACE and are, therefore, useful in reducing Abeta levels.

We claim:
1. A compound of the formula:

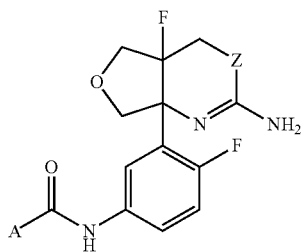

wherein A is:

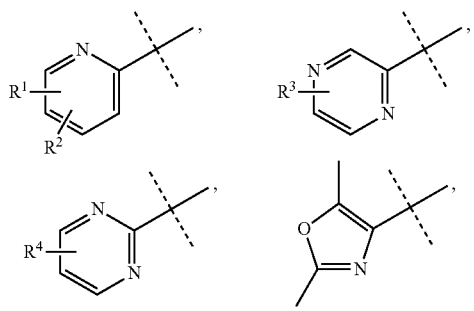

-continued

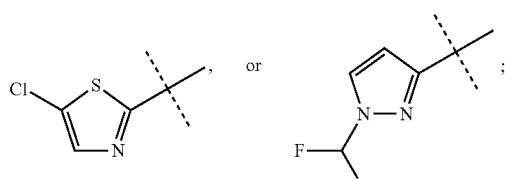

Z is O;
R¹ is H, F, Cl, CN, OCH₃, OCH₂CH₂OCH₃,

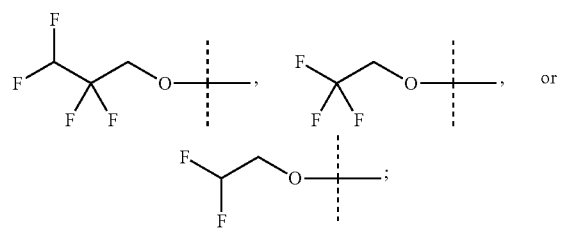

R² is H, F, Cl, or CH₃;
R³ is H, F, Cl, CH₃, CF₃, C1-C3 alkoxy, OCH₂CH₂OCH₃,

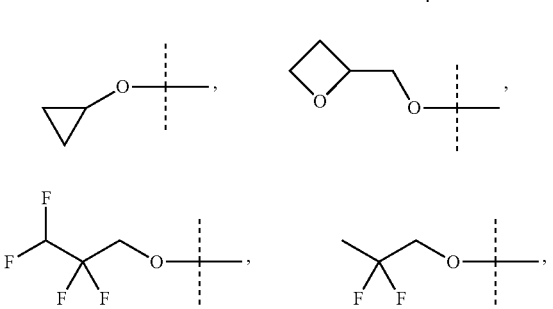

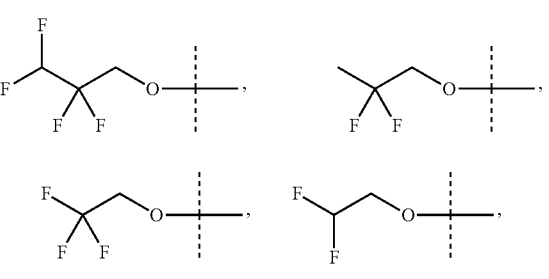

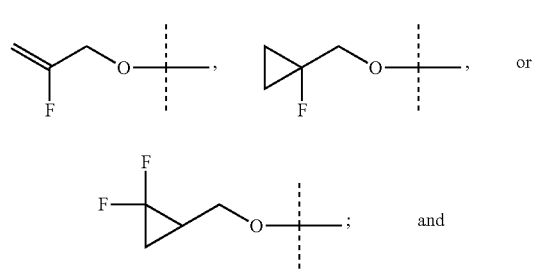

R⁴ is H, F, Cl, or OCH₃;
or a pharmaceutically acceptable salt thereof.

2. The compound or salt according to claim 1 in the (cis)-configuration:

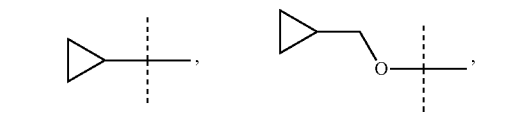

3. The compound or salt according to claim 2 wherein A is:

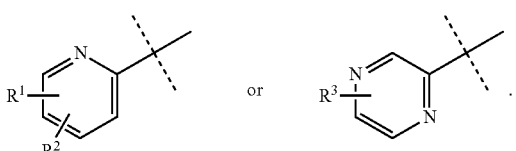

4. The compound or salt according to claim 3 wherein A is:

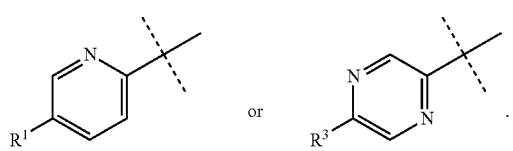

5. The compound or salt according to claim 4 wherein A is:

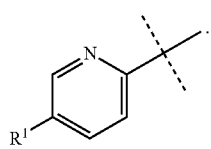

6. The compound or salt according to 5 wherein A is:

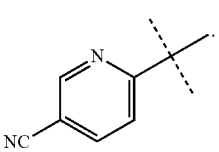

7. The compound or salt according to claim 4 wherein R³ is OCH₃, CH₂CF₃,

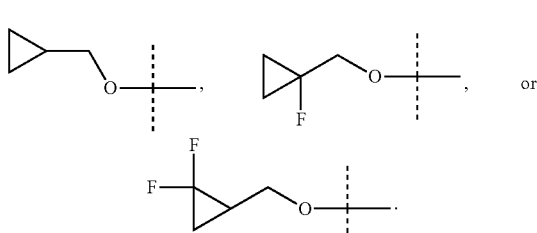

8. The compound or salt according to claim 7 wherein R³ is OCH₃.

9. The compound or salt according to claim 1 wherein Z is O.

10. The compound or salt according to claim 4 wherein Z is O.

11. The compound or salt according to claim 7 wherein Z is O.

12. The compound or salt according to claim 1 which is N-[3-[(4aR,7aS)-2-amino-4a-fluoro-5,7-dihydro-4H-furo[3,4-d][1,3]oxazin-7a-yl]-4-fluoro-phenyl]-5-cyano-pyridine-2-carboxamide.

13. The compound according to claim 12 which is N-[3-[(4aR,7aS)-2-amino-4a-fluoro-5,7-dihydro-4H-furo[3,4-d][1,3]oxazin-7a-yl]-4-fluoro-phenyl]-5-cyano-pyridine-2-carboxamide.

14. A method of treating Alzheimer's disease in a patient, comprising administering to a patient in need of such treatment an effective amount of a compound according to claim 1, or a pharmaceutically acceptable salt thereof.

15. A pharmaceutical composition, comprising a compound or a pharmaceutically acceptable salt thereof according to claim 1 with one or more pharmaceutically acceptable carriers, diluents, or excipients.

\* \* \* \* \*